US006867189B2

(12) United States Patent
Lucas et al.

(10) Patent No.: US 6,867,189 B2
(45) Date of Patent: Mar. 15, 2005

(54) USE OF ADIPSIN/COMPLEMENT FACTOR D IN THE TREATMENT OF METABOLIC RELATED DISORDERS

(75) Inventors: John Lucas, San Diego, CA (US); Kristen Briggs, Del Mar, CA (US)

(73) Assignee: Genset S.A. (FR)

(*) Notice: Subject to any disclaimer, the term of this patent is extended or adjusted under 35 U.S.C. 154(b) by 90 days.

(21) Appl. No.: 10/202,676

(22) Filed: Jul. 22, 2002

(65) Prior Publication Data

US 2003/0092620 A1 May 15, 2003

Related U.S. Application Data

(60) Provisional application No. 60/308,147, filed on Jul. 26, 2001.

(51) Int. Cl.[7] .............................................. A61K 38/17
(52) U.S. Cl. .................... 514/12; 435/69.1; 435/320.1; 530/324
(58) Field of Search ........................ 514/12; 435/69.1, 435/320.1

(56) References Cited

U.S. PATENT DOCUMENTS

| | | |
|---|---|---|
| 4,179,337 A | 12/1979 | Davis et al. |
| 4,444,887 A | 4/1984 | Hoffmann |
| 4,474,893 A | 10/1984 | Reading |
| 4,631,211 A | 12/1986 | Houghten |
| 4,714,681 A | 12/1987 | Reading |
| 4,716,111 A | 12/1987 | Osband et al. |
| 4,736,866 A | 4/1988 | Leder et al. |
| 4,925,648 A | 5/1990 | Hansen et al. |
| 4,946,778 A | 8/1990 | Ladner et al. |
| 5,073,627 A | 12/1991 | Curtis et al. |
| 5,082,767 A | 1/1992 | Hatfield et al. |
| 5,112,946 A | 5/1992 | Maione |
| 5,223,409 A | 6/1993 | Ladner et al. |
| 5,223,425 A * | 6/1993 | Flier et al. .................. 435/358 |
| 5,258,498 A | 11/1993 | Huston et al. |
| 5,283,173 A | 2/1994 | Fields et al. |
| 5,314,995 A | 5/1994 | Fell, Jr. et al. |
| 5,336,603 A | 8/1994 | Capon et al. |
| 5,359,046 A | 10/1994 | Capon et al. |
| 5,403,484 A | 4/1995 | Ladner et al. |
| 5,427,908 A | 6/1995 | Dower et al. |
| 5,447,851 A | 9/1995 | Beutler et al. |
| 5,474,981 A | 12/1995 | Leder et al. |
| 5,478,925 A | 12/1995 | Wallach et al. |
| 5,516,637 A | 5/1996 | Huang et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,571,698 A | 11/1996 | Ladner et al. |
| 5,573,920 A | 11/1996 | Randle |
| 5,580,717 A | 12/1996 | Dower et al. |
| 5,580,734 A | 12/1996 | Treco et al. |
| 5,585,089 A | 12/1996 | Queen et al. |
| 5,601,819 A | 2/1997 | Wong et al. |
| 5,605,793 A | 2/1997 | Stemmer |
| 5,608,426 A | 3/1997 | Hester |
| 5,622,929 A | 4/1997 | Willner et al. |

(List continued on next page.)

FOREIGN PATENT DOCUMENTS

| | | |
|---|---|---|
| EP | 0 036 776 A2 | 9/1981 |
| EP | 0 239 400 A2 | 9/1987 |
| EP | 0 307 434 | 3/1989 |
| EP | 0 367 166 A1 | 5/1990 |
| EP | 0 394 827 A1 | 10/1990 |
| EP | 0 396 387 B1 | 11/1990 |
| EP | 0 401 384 B1 | 12/1990 |
| EP | 0 439 095 A2 | 7/1991 |
| EP | 0 519 596 A1 | 12/1992 |
| EP | 0 572 287 A2 | 12/1993 |
| EP | 0 592 106 A1 | 4/1994 |
| WO | WO 84/03506 A1 | 9/1984 |
| WO | WO 84/03564 A1 | 9/1984 |
| WO | WO 89/12624 A2 | 12/1989 |
| WO | WO 90/02809 A1 | 3/1990 |
| WO | WO 90/11092 A1 | 10/1990 |
| WO | WO 91/00360 A1 | 1/1991 |
| WO | WO 91/06570 A1 | 5/1991 |
| WO | WO 91/08216 A1 | 6/1991 |
| WO | WO 91/09967 A1 | 7/1991 |

(List continued on next page.)

OTHER PUBLICATIONS

Friedman, "Obesity in the new millenium", *Nature* (2000), 404(6778):632–634.

Kopelman, "Obesity as a medical problem", *Nature* (2000), 404(6778):635–643.

Barsh, et al., "Genetics of body–weight regulation", *Nature* (2000), 404(6778):644–651.

Kim, S.J., "Crystal structure of a complement factor D mutant expressing enhanced catalytic activity", *J. Biol. Chem.* (1995), 270(41):24399–24405.

Volanakis, J.E., "Complement factor D, a novel serine protease", *Protein Science* (1996), 5:553–564.

Smith and Johnson, "Single–step purification of polypeptides expressed in *Escherichia coli* as fusions with glutathione S–transferase", *Gene* (1988), 67(1):31–40.

(List continued on next page.)

*Primary Examiner*—Karen Cochrane Carlson
*Assistant Examiner*—Anand U Desai
(74) *Attorney, Agent, or Firm*—Saliwanchik, Lloyd & Saliwanchik

(57) ABSTRACT

The present invention relates to the field of metabolic research. Metabolic disorders, such as obesity, are a public health problem that is serious and widespread. Adipsin polypeptides have been identified that are believed to be beneficial in the treatment of metabolic disorders. These compounds should be effective for reducing body mass and for treating metabolic-related diseases and disorders. These metabolic-related diseases and disorders include hyperlipidemias, atherosclerosis, insulin resistance, diabetes, and hypertension.

54 Claims, No Drawings

U.S. PATENT DOCUMENTS

| | | |
|---|---|---|
| 5,641,670 A | 6/1997 | Treco et al. |
| 5,641,870 A | 6/1997 | Treco et al. |
| 5,658,727 A | 8/1997 | Barbas et al. |
| 5,667,973 A | 9/1997 | Fields et al. |
| 5,733,734 A | 3/1998 | Trojanowski et al. |
| 5,733,761 A | 3/1998 | Treco et al. |
| 5,750,753 A | 5/1998 | Kimae et al. |
| 5,780,225 A | 7/1998 | Wigler et al. |
| 5,783,385 A | 7/1998 | Treco et al. |
| 5,807,715 A | 9/1998 | Morrison et al. |
| 5,811,097 A | 9/1998 | Allison et al. |
| 5,811,238 A | 9/1998 | Stemmer et al. |
| 5,814,318 A | 9/1998 | Lonberg et al. |
| 5,817,789 A | 10/1998 | Heartlein et al. |
| 5,821,047 A | 10/1998 | Garrard et al. |
| 5,834,252 A | 11/1998 | Stemmer et al. |
| 5,837,458 A | 11/1998 | Minshull et al. |
| 5,869,239 A | 2/1999 | Treco et al. |
| 5,869,330 A | 2/1999 | Scherer et al. |
| 5,965,125 A | 10/1999 | Mineau-Hanschke |
| 5,968,502 A | 10/1999 | Treco et al. |
| 5,994,127 A | 11/1999 | Selden et al. |
| 5,994,616 A | 11/1999 | Rosen |
| 6,013,857 A | 1/2000 | Deboer et al. |
| 6,048,524 A | 4/2000 | Selden et al. |
| 6,048,724 A | 4/2000 | Selden et al. |
| 6,048,729 A | 4/2000 | Selden et al. |
| 6,054,288 A | 4/2000 | Selden et al. |
| 6,140,552 A | 10/2000 | Deboer et al. |
| 2003/0170630 A1 * | 1/2003 | Alsobrook, II et al. |
| 2003/0212256 A1 * | 2/2003 | Ediger et al. |

FOREIGN PATENT DOCUMENTS

| | | |
|---|---|---|
| WO | WO 91/10737 A1 | 7/1991 |
| WO | WO 91/10741 A1 | 7/1991 |
| WO | WO 91/14438 A1 | 10/1991 |
| WO | WO 92/01047 A1 | 1/1992 |
| WO | WO 92/05793 A1 | 4/1992 |
| WO | WO 92/08495 A1 | 5/1992 |
| WO | WO 92/08802 A1 | 5/1992 |
| WO | WO 92/18522 A1 | 10/1992 |
| WO | WO 92/18619 A1 | 10/1992 |
| WO | WO 92/22324 A1 | 12/1992 |
| WO | WO 93/11236 A1 | 6/1993 |
| WO | WO 93/17717 A1 | 9/1993 |
| WO | WO 93/21232 A1 | 10/1993 |
| WO | WO 93/25234 A1 | 12/1993 |
| WO | WO 94/06920 A1 | 3/1994 |
| WO | WO 94/10308 A1 | 5/1994 |
| WO | WO 94/12650 A2 | 6/1994 |
| WO | WO 94/23026 A1 | 10/1994 |
| WO | WO 95/04141 A1 | 2/1995 |
| WO | WO 95/11307 A1 | 4/1995 |
| WO | WO 95/15982 A2 | 6/1995 |
| WO | WO 95/20401 A1 | 8/1995 |
| WO | WO 96/04388 A1 | 2/1996 |
| WO | WO 96/29411 A1 | 9/1996 |
| WO | WO 96/31523 A1 | 10/1996 |
| WO | WO 96/33735 A1 | 10/1996 |
| WO | WO 96/34096 A1 | 10/1996 |
| WO | WO 96/40281 A2 | 12/1996 |
| WO | WO 98/24893 A2 | 6/1998 |
| WO | WO 98/45438 A1 | 10/1998 |
| WO | WO 98/46645 A2 | 10/1998 |
| WO | WO 98/49305 A1 | 11/1998 |
| WO | WO 98/50433 A2 | 11/1998 |

OTHER PUBLICATIONS

Bowie et al., "Deciphering the message in protein sequences: tolerance to amino acid substitutions", *Science* (1990), 247:1306–1310.

Vaitukaitis, et al., "A method for producing specific antisera with small doses of immunogen", *J. Clin. Endocrinol. Metab.* (1971), 33:988–991.

Zoller, et al., "Oligonucleotide–directed mutagenesis using M13–derived vectors: an efficient and general procedure for the production of point mutations in any fragment of DNA", *Nucl. Acids. Res.* (1987), 10:6487.

Wells, et al. "Cassette mutagenesis: an efficient method for generation of mutations at defined sites", *Gene* (1985), 34:315.

Wells, et al., "Importance of hydrogen–bond formation in stabilizing the transition state of subtilisin", *Philos Trans. R. Soc. London SerA* (1986), 317:415.

Cunningham, et al., "High–resolution epitope mapping of hGH–recptor interactions by alanine–scanning mutagenesis", *Science* (1989), 244:1081–1085.

Creighton. *Proteins: Structures and Molecule Principles,* W.H. Freeman Co., ($2^{nd}$ ed. 1983), T.E., NY.

Davis, et al., *Method in Molecular Biology,* (ed. 1986); Elsevier Press, NY.

Pinckard, et al., "Factors influencing the immune response", *Clin. Exp. Immunol.* (1967), 2:331–340.

Robbins et al., "Antibodies to covalent aggregates of insulin in blood of insulin–using diabetic patients", *Diabetes* (1987), 36:838–845.

Engvall, "Enzyme Immunoassay ELISA and EMIT", *Meth. Enzymol.* (1980), 70:491–439.

Pearson, et al., "Improved tools for biological sequence comparison", *Proc. Natl. Acad. Sci. USA* (1988), 85(8):2444–8.

Altschul, S.F. et al., "Basic local alignment search tool", *J. Mol. Biol.* (1990), 5:215(3):403–10; PMID: 223712.

Thompson, et al., "Clustal W: improving the sensitivity of progressive multiple sequence alignment through sequence weighting, position–specific gap penalties and weight matrix choice", *Nucleic Acids Res.* (1994), 22(22):4673–4680.

Higgins, D.G. et al., "Using CLUSTAL for multiple sequence alignments", *Methods Enzymol.* (1996), 266:383–402; PMID:8743695.

Altschul, et al., "Gapped BLAST and PSI–BLAST: a new generation of protein database search programs", *Nucleic Acids Res.* (1997), 25(17):3389–402; PMID: 9254694.

Ol, et al., "Chimeric antibodies", *Biotechniques* (1986), 4:214–221.

Karlin, S. and Altschul, S. "Methods for assessing the statistical significance of molecular sequence featurews by using general scoring schemes", *Proc. Natl. Acad. Sci. USA* (1990), 87(6):2264–8; PMID:2315319.

Gonnet et al., "Exhaustive matching of the entire protein sequence database", *Science* (1992), 256:1443–1445.

Henikoff et al., "Performance evaluation of amino acid substitution matrices", *Proteins* (1993), 17(1):49–61; PMID:8234244.

Greenspan and Bona, "Idiotypes; structure and immunogenicity", *FASEB J.* (1993), 7(5):437–444.

Nisonoff, "Idiotypes: Concepts and Applications", *J. Immunol.* (1991), 147(8):2429–2438.

Kohler, G. and Milstein, C. "Continuous cultures of fused cells secreting antibody of predefinied specificity", *Nature* (1975), 256:495.

Shimabukuro, et al., "Direct antidiabetic effect of leptin through triglyceride depletion of tissues", Proc. Natl. Acad. Sic. USA (1997), 94:4637–4641.

Wilkins and Velander, "Isolation of Recombinant Proteins From Milk", *J. Cell. Biochem.* (1992), 49:333–8.

Bartunek, P. et al., "Avian stem cell factor (SCF): production and characterization of the recombinant his–tagged SCF of chicken and its neutralizing antibody", *Cytokine* (1996), 8(1):14–20.

Harris, et al., "The application of aqueous two–phase systems to the purification of pharmaceutical proteins from transgenic sheep milk", *Bioseparation* (1997), 7:31–7.

Degener, et al., "$Zn^{2+}$–selective purification of recombinant proteins from the milk of transgenic animals", *J. Chromatog* (1998), 799:125–37.

Wilkins, "Purification of Proteins from Milk of Transgenic Animals", *J. Cell Biochem. Suppl.* (1993), (17 part A):39.

Davis, et al. *Basic Methods in Molecular Biology,* (ed. 1986); Elsevier Press, NY.

Koller, et al., "Inactivating the B2–microglobulin locus in mouse embryonic stem cells by homologous recombination", *Proc. Natl. Acad. Sic. USA* (1989), 86(22):8932–5.

Koller, et al., "Germ–line transmission of a planned alteration made in a hypoxanthine phosphorlbosyltransferase gene by homolgous recombination in embryonic stem cells", *Proc. Natl. Acad. Sic. USA* (1989), 86(22):8927–31.

Zijlstra, et al., "Germ–line transmission of a disrupted $\beta_2$–microglobulin gene produced by homologous recombination in embryonic stem cells", *Nature* (1989), 342(6248):435–8.

Hunkapiller, et al., "A microchemical facility for the analysis and synthesis of genes and proteins", *Nature* (1984), 310(5973):105–111.

Malik, et al., "Polyethylene Glycol (PEG)–modified Granulocyte–Macrophage Colony–stimulating Factor (GM–CSF) with Conserved Biological Activity", *Exp. Hematol.* (1992), 20(8):1028–35.

Muller, et al., "VEGF and the fab fragment of a humanized neutralizing antibody:crystal structure of the complex at 2.4 A resolution and mutational analysis of the interface", *Structure* (1998), 6(9):1153–1167.

Hoppe, et al., "A parallel three stranded α–helical bundle at the nucleation site of collagen triple–helix formation", *FEBS Letters* (1994) 344:191–195.

Carlson, et al., "Identification of amino acids in the glutamate receptor, GluR3, important for antibody–binding and receptor–specific activation", *J. Biol. Chem.* (1997), 272(17):11295–11301.

Gentz, R. et al., "Bioassay for trans–activation using purified human immunodeficiency virus tat–encoded protein: trans–activation requires mRNA synthesis," *Proc. Natl. Acad. Sci. USA* (1989), 86(3):821–4; PMID:2536934.

Wilson, I.A. et al., "The structure of an antigenic determinant in a protein", *Cell* (1984), 37(3):767–778.

Smith, et al., "Production of human beta interferon in insect cells infected with a baculovirus expression vector", *Mol. Cell. Biol.* (1983), 3(12):2156–2165.

Liautard, et al., "Specific inhibition of IL–6 signalling with monoclonal antibodies against the gp130 receptor", *Cytokine* (1997), 9(4):233–241.

Sambrook, et al. *Molecular Cloning: A Laboratory Manual* ($2^{nd}$ ed., 1989) Cold Spring Harbor Laboratory, Cold Spring Harbor, New York.

Pitard, et al., "Production and characterization of monoclonal antibodies against the leukemia inhibitory factor low affinity receptor gp190", *J. Immunol. Methods* (1997), 205(2):177–190.

Chai, et al., "Glycosylation and high–level secretion of human tumour necrosis factor–β in recombinant baculovirus–infected insect cells", *Biotechnol. Appl. Biochem.* (1993), 18:259–273.

Vlasak, et al., "Nucleotide sequence of cloned cDNA coding for honeybee prepromelittin", *Eur. J. Biochem.* (1983), 135:123–126.

Lenhard, et al., "A new set of versatile vectors for the heterologous expression of foreign genes using the baculovirus system", *Gene* (1996), 169:187–190.

Yoon, et al., "Antibodies to domains II and III of the IL–1 receptor accessory protein inhibit IL–1β activity but not binding: regulation of IL–1 responses is via type I receptor, not the accessory protein[1]", *J. Immunol.* (1998), 160(7):3170–3179.

Ohno, et al., "Gene therapy for vascular smooth muscle cell proliferation after arterial injury", *Science* (1994), 265:781–784.

Roux, et al., "A versatile and potentially general approach to the targeting of specific cell types by retroviruses: application to the infection of human cells by means of major histocompatibility complex class I and class II antigens by mouse ecotropic murine leukemia virus–derived viruses", *Proc. Natl. Acad. Sci. USA* (1989), 86:9079–0–83.

Etienne–Julan, et al., "The efficiency of cell targeting by recombinant retroviruses depends on the nature of the receptor and the composition of the artificial cell–virus linker", *J. Gen. Virol:* (1992), 73:3251–3255.

Neda, et al., "Chemical modification of an ecotropic murine leukemia virus results in redirection of its target cell specificity", *J. Biol. Chem.* (1991), 266:14143–14146.

Muzyczka, et al., "Use of adeno–associated virus as a general transduction vector for mammalian cells", *Current Topics in Micro. And Immunol.* (1992), 158:97–129.

Flotte, et al., "Gene expression from adeno–associated virus vectors in airway epithelial cells", *Am. J. Respir. Cell Mol. Biol.* (1992), 7:349–356.

Samulski, et al., "Helper–free stocks of recombinant adeno–associated viruses: normal integration does not require viral gene expression", *J. Virol.* (1989), 63:3822–3828.

McLaughlin, et al., "Adeno–associated virus general transduction vectors; analysis of proviral structures", *J. Virol.* (1988), 62(6):1963–1973.

Graham, et al., "Transformation of Rat Cells by DNA of Human Adenovirus 5", *Virology* (1973), 54(2):536–9.

Chen et al., "High–efficiency transformation and ammmalian cells by plasmid DNA", *Mol. Cell. Biol.* (1987), 7(8):2745–2752.

Gopal, "Gene transfer method for transient gene expression, stable transformation, and cotransformation of suspension cell cultures", *Mol. Cell. Biol.* (1985), 5(5):1188–1190.

Tur–Kaspa, et al., "Use of electroporation to introduce biologically active foreign genes into primary rat hepatocytes", *Mol. Cell. Biol.* (1986), 6(2):716–718.

Potter, et al., "Enhancer–dependent expression of human κ Immunoglobulin genes introduced into mouse pre–B lymphocytes by electroporation", *Proc. Natl. Acad. Sci. USA* (1984), 81(22):7161–7165.

Harland, et al., "Translation of mRNA Injected into *Xenopus Oocytes* Is Specifically Inhibited by Antisense RNA", *J. Cell. Biol.* (1985), 101:1094–1095.

Nicolau, et al., "Liposome–mediated DNA transfer in eukaryotic cells", *Biochim. Biophys. Acta.* (1982), 721:185–190.

Fraley, et al., "Entrapment of a bacterial plasmid in phospholipid vesicles: potential for gene transfer", *Proc. Natl. Acad. Sci. USA* (1979), 76:3348–3352.

Wu and Wu, "Receptor–mediated in Vitro gene transformation by a soluble DNA carrier system", *J. Biol. Chem.* (1987), 262:4429–4432.

Wu and Wu, "Evidence for Targeted Gene Delivery to Hep G2 Heptoma Cells in Vitro", *Biochemistry* (1988), 27:887–892.

Tascon, et al., "Vaccination against tuberculosis by DNA injection", *Nature Medicine* (1996), 2(8):888–892.

Huygen, et al., "Immunogenicity and protective efficacy of a tuberculosis DNA vaccine", *Nature Medicine* (1996), 2(8):893–898.

Klein, et al., "High–velocity microprojectiles for delivering nucleic acids into living cells", *Nature* (1987), 327:70–73.

Prat, et al., "Agonistic monoclonal antibodies against the Met receptor dissect the biological responses to HGF", *J. Cell Sci.* (1998), 111(Pt2):237–247.

Wong, et al., "Appearance of β–lactamase activity in animal cells upon liposome–mediated gene transfer", *Gene* (1980), 10:87–94.

Nicolau, et al., "Liposomes as Carriers for in Vivo Gene Transfer and Expression", *Methods Enzymol.* (1987), 149:157–76.

Zhu et al., "Inhibition of vascular endothelial growth factor–induced receptor activation with anti–kinase insert domain–containing receptor single–chain antibodies from a phage display library", *Cancer Res.* (1998).

Fried and Crothers, "Equilibria and kinetics of lac repressor–operator interations by polyacrylamide gel electrophoresis", *Nucl. Acids Res.* (1981), 9:6505–6525.

Garner and Revzin, "A gel electrophoresis method for quantifying the binding of proteins to specific DNA regions: application to components of the *Escherichia coli* lactose operon regulatory system", *Nucl. Acids Res.* (1981), 9:3047–3060.

Latchman, D.S. "The DNA mobility shift assay" in: *Transcription Factors: A Practical Approach* (Latchman, D.S., ed. 1993) pp. 1–26, Oxford: ILR Press.

Harrop, et al., "Antibodies to TR2 (Herpesvirus entry mediator), a new member of the TNF receptor superfamily, block T cell proliferation, expression of activation markers, and production of cytokines", *J. Immunol.* (1988), 161(4):1786–1794.

Parmley and Smith, "Antibody–selectable filamentous fd phage vectors: affinity purification of target genes", *Gene* (1988), 73:305–318.

Oldenburg, et al., "Peptide ligands for a sugar–binding protein isolated from a random peptide library", *Proc. Natl. Acad. Sci. USA* (1992), 89:5393–5397.

Valadon, et al., "Peptide libraries define the fine specificity of anti–polysaccharide antibodies to *Cryptococcus neoformans*", *J. Mol. Biol.* (1996), 261:11–22.

Deng, et al., "An agonist murine monoclonal antibody to the Human c–Mpl receptor stimulates megakaryocytopoiesis", *Blood* (1998), 92(6):1981–1988.

Gavrilova, et al., "Leptin and diabetes in lipoatrophic mice", *Nature* (2000), 403:850.

Felici, "Selection of antibody ligands from a large library of oligopeptides expressed on a multivalent exposition vector", *J. Mol. Biol.* (1991), 222:301–310.

Rasmussen, et al., "Two–dimensional electrophoretic analysis of human breast carcinoma proteins: mapping of proteins that bind to the SH3 domain of mixed lineage kinase MLK2", *Electrophoresis* (1997), 18:588–598.

Edwards and Letherbarrow, "Determination of association rate constants by an optical biosensor using initial rate analysis", *Analytical Biochemistry* (1997), 246:1–6.

Szabo, et al., "Surface plasmon resonance and its use in biomolecular interaction analysis (BIA)", *Curr. Opin. Struct. Biol.* (1995), 5:699–705.

Harper, et al., "The p21 Cdk–interacting protein Clp1 is a potent inhibitor of G1 cyclin–dependent kinases", *Cell* (1993), 75:805–816.

Cho, et al., "Parallel analysis of genetic selections using whole genome olignucleotide arrays", *Proc. Natl. Acad. Sci. USA* (1998), 95(7):3752–3757.

Fromont–Racine, et al., "Toward a functional analysis of the yeast genome through exhaustive two–hybrid screens", *Nature Genetics* (1997), 16(3):277–282.

Vie, et al., "Human fusion proteins between interleukin 2 and IgM heavy chain are cytotoxic for cells expressing the interleukin 2 receptor", *Proc. Natl. Acad. Sci. USA* (1992), 89:11337–11341.

Green, et al., "The role of antisense RNA in gene regulation", *Ann. Rev. Biochem* (1986), 55:569–597.

Izant and Weintraub, "Inhibition of thymidine kinase gene expression by anti–sense RNA: a molecular approach to genetic analysis", *Cell* (1984), 36(4):1007–1015.

Rossi, et al., "The potential use of catalytic RNAs in therapy of HIV infection and other diseases", *Pharacol. Ther.* (1991), 50:245–254.

Sczakiel, et al., "The potential of ribozymes as antiviral agents", *Trends Microbiol.* (1995), 3(6):213–217.

Griffin, et al., "Recognition of thymine adenine base pairs by guanine in a pyrimidine triple helix motif", *Science* (1989), 245:967–971.

Koller, B. "Altering Genes in Animals by Gene Targeting", *Annu. Rev. Immunol.* (1992), 10:705–30.

Schedl, et al., "A yeast artificial chromosome covering the tyrosinase gene confers copy number–dependent expression in transgenic mice", *Nature* (1993), 362:258–261.

Abbondanzo, et al., "Derivation of Embryonic Stem Cell Lines", *Methods Enzymol.* (1993), 225:803–23.

Robertson, "Embryo–derived stem cell lines", IN: E.J. Robertson ed. "Teratocarcinomas and embryonic stem cells: a practical approach"; (1987), pp. 71, IRL Press, Oxford.

Pease and Williams, "Formation of germ–line chimeras from embryonic stem cells maintained with recombinant leukemia inhibitory factor", *Exp. Cell Res.* (1990), 190:209–211.

Jaenisch, R., "Germ line integration and Mendalian transmission of the exogenous Moloney leukemia virus", *Proc. Natl. Acad. Sic. USA* (1976), 73:1260–1264.

Wall, et al., "Making Transgenic Livestock: Genetic Engineering on a Large Scale", *J. Cell Biochm* (1992), 49(2):113–20.

Zheng, X.X. et al., "Administration of noncytolytic IL–10–Fc in murine models of lipopolysaccharide–induced septic shock and allogeneic islet transplantation[1]", *J. Immunol.* (1995), 154:5590–5600.

Gordon, et al., "Gene transfer into mouse embryos: production of transgenic mice by pronuclear injection", *Methods in Enzymology* (1984), 101:411–433.

Hammer, et al., "Production of transgenic rabbits, sheep and pigs by microinjection", *Nature* (1985). 315:680–683.

Gandolfi, et al., "Stimulation of early embryonic development in the sheep by co–culture with oviduct epithelial cells", *J. Reprod. Fert.* (1987), 81, 23–28.

Rexroad, et al., "Co–culture of ovine ova with oviductal cells in medium 199", *J. Anim. Sci.* (1988), 66:947–953.

Eyestone, et al., "Co–culture of early cattle embryos to the blastocyst stage with oviducal tissue or in conditioned medium", *J. Reprod. Fert.* (1989), 85:715–720.

Camous, et al., "Cleavage beyond the block stage and survival after transfer of early bovine embryos cultured with trophoblastic vesicles", *J. Reprod. Fert.* (1984), 72:479–485.

Heyman, et al., "In vitro cleavage of bovine and ovine early embryos: improved development using coculture with trophoblastic vesicles", *Theriogenology* (1987) 27(1):59–68.

Clark, "The mammary gland as a bioreactor: expression, processing, and production of recombinant proteins", *J. Mammary Gland Biol. Neoplasia* (1998), 3(3):337–50.

Jost, et al., "Production of low–lactose milk by ectopic expression of intestinal lactase in the mouse mammary gland", *Nat. Biotechnol.* (1999), 17:160–4.

Sohn, et al., "Expression and characterization of bioactive human thrombopoietin in the milk of transgenic mice". *DNA Cell Biol.* (1999), 18:845–52.

Kim, et al., "High–Level Expression of Human Lactoferrin in Milk of Transgenic Mice Using Geonmic Lactoferrin Sequence", *J. Biochem.* (Japan) (1999), 126:320–5.

Soulier, et al., "Use of doxycycline–controlled gene expression to reversible alter milk–protein composition in transgenic mice", *Euro. J. Biochem.* (1999), 260:533–9.

Ashkenazi, et al., "Protection against endotoxic shock by a tumor necrosis factor receptor immunoadhesin", *Proc. Natl. Acad. Sci. USA* (1991), 88:10535–10539.

Rjinkels, et al., "High–level expression of bovine $\alpha_{s1}$–casein in milk of transgenic mice", *Transgen. Res.* (1998), 7:5–14.

Korhonen, et al., "Expression of bovine β–lactoglobulin/human erythropoietin fusion protein in the milk of transgenic mice and rabbits", *Euro. J. Biochem.* (1997), 245:482–489.

Uusi–Oukari, et al., "Bovine $\alpha_{s1}$–casein gene sequences direct high level expression of human granulocyte–macrophage colony–stimulating factor in the mild of transgenic mice", *Transgen Res.* (1997), 6:75–84.

Hitchin, et al. "Bovine β–casein expressed in transgenic mouse milk is phosphorylated and incorporated into micelles", *Prot. Expr. Purif.* (1996), 7:247–52.

Gilles, S.O., et al., "Antibody–Targeted Interleukin 2 Stimulates T–Cell Killing of Autologus Tumor Cells", *Proc. Natl. Acad. Sci. USA* (1992), 89(4):1428–1432.

Fell, et al., "Genetic construction and characterization of a fusion protein consisting of a chimeric F(ab') with specificity for carcinomas and human IL–2", *J. Immunol.* (1991), 146:2446–2452.

Christa, et al. "High expression of the human hepatocarcinoma–intestine–pancreas/pancreatic–associated protein (HIP/PAP) gene in the mammary gland of lactating transgenic mice", *Euro. J. Biochem.* (2000), 267:1665–71.

Hens, et al., "Introduction of the human growth hormone gene into the guinea pig mammary gland by in vivo promotes sustained expression of human growth hormone in the milk throughout lactation", *Biochim. Biophys. Acta.* (2000), 1523:161–171.

Sobolev, et al., "Receptor–mediated transfection of murine and ovine mammary glands in vivo", *J. Biol. Chem.* (1998), 273:7928–33.

Archer, et al., "Human growth hormone (hGH) secretion in milk of goals after direct transfer of the hGH gene into the mammary gland by using replication–defective retroviruses vectors", *PNAS* (1994), 91:6840–6844.

Naramura, et al., "Mechanisms of cellular cytotoxicity mediated by a recombinant antibody–IL–2 fusion protein against human melanoma cells", *Immunol. Lett.* (1994), 39:91–99.

Roguska, et al., "Humanization of murine monoclonal antibodies through variable domain resurfacing", *Proc. Natl. Acad. Sci. USA* (1994), 91:969–973.

Geysen, et al., "Use of peptide synthesis to probe viral antigens for epitopes to a resolution of a single amino acid", *Proc. Natl. Acad. Sci. USA* (1984), 81:3998–4002.

Houghton, "General method for the rapid solid–phase synthesis of large numbers of peptides: specificity of antigen–antibody interaction at the level of individual amino acids", *Proc. Natl. Acad. Sci. USA* (1985), 82:5131–5135.

Studnicka, et al., "Human–engineered monoclonal antibodies retain full specific binding activity by preserving non–CDR complementarity–modulating residues", *Protein Engineering* (1994), 7(6):805–814.

Sutcliffe, et al., "Antibodies that react with predetermined sites on proteins", *Science* (1983), 219:660–666.

Chow, et al., "Synthetic peptides from four separate regions of the poliovirus type 1 capsid protein VP1 induce neutralizing antibodies", *Proc. Natl. Acad. Sci. USA* (1985), B2:910–914.

Francis, et al., "Immunological priming with synthetic peptides of foot–and–mouth disease virus", *J. Gen. Virol* (1985), 66(11):2347–2354.

Traunecker, et al., "Soluble CD4 molecules neutralize human immunodeficiency virus type 1", *Nature* (1988), 331:84–86.

Fountoulakis, et al., "Interferon γ receptor extracellular domain expressed as IgG fusion protein in Chinese hamster ovary cells", *J. Biol. Chem.*, (1995), 270 (8):3958–3964.

Padlan, "A possible procedure for reducing the immunogenicity of antibody variable domains while preserving their ligand–binding properties", *Molec. Immunol.* (1991), 28(4/5):489–498.

Harayama, "Artificial evolution by DNA shuffling", *Trends Biotechnol.* (1998), 16(2):76–82.

Hansson, et al., "Evolution of differential substrate specificities in Mu class glutathione transferases probed by DNA shuffling", *J. Mol. Biotechnol.* (1999), 287:265–276.

Lorenzo and Blasco, "PCR–based method for the introduction of mutations in genes cloned and expressed in vaccinia virus", *Biotechniques* (1998), 24(2):308–313.

Tutt, et al., "Trispecific F(ab')₃ derivatives that use cooperative signaling via the tcr/cd3 complex and cd2 to activate and redirect resting cytotoxix T cells", *J. Immunol.* (1991), 147:60–69.

Kostelny, et al., "Formation of a bispecific antibody by the use of leucine zippers", *J. Immunol.* (1992), 148:1547–1553.

Harlow and Lane. *Antibodies A Laboratory Manual,* (1988) Cold Spring Harbor Laboratory, pp. 53–242.

Gillies, et al., "High–level expression of chimeric antibodies using adapted cDNA variable region cassettes", *J. Immunol. Methods.* (1989), 125:191–202.

Brinkmann, U. et al., "Phage Display of Disulfide–stabilized Fv Fragments", *J. Immunol. Methods* (1995), 182:41–50.

Ames, et al., "Conversion of murine Fabs isolated from a combinatorial phage display library to full length immunoglobulins", *J. Immunol. Methods* (1995), 184:177–186.

Kettleborough, et al., "Isolation of tumor cell–specific single–chain Fv from immunized mice using phage–antibody libraries and the re–construction of whole antibodies from these antibody fragments", *Eur. L. Immunol.* (1994), 24:952–958.

Persic et al., "An integrated vector system for the eukaryotic expression of antibodies for their fragments after selection from phage display libraries", *Gene* (1997), 187:9–18.

Burton and Barbas, "Human antibodies from combinatorial libraries", *Adv. Immunol.* (1994), 57:191–280.

Mullinax, et al., "Expression of a heterodimeric fab antibody protein in one cloning step", *Biotechniques* (1992), 12(6):864–869.

Gavrilova, et al., "Lack of Responses to a $\beta_3$–Adrenergic Agonist in Lipoatrophic A–ZIP/F–1 mice", *Diabetes* (2000), 49(11):1910–8.

Sawai, et al., "Direct production of the Fab fragment derived from the sperm immobilizing antibody using polymerase chain reaction and cDNA expression vectors", *AJRI* (1995), 34:26–34.

Better, et al., "*Escherichia coli* secretion of an active chimeric antibody fragment", *Science* (1988), 240:1041–1043.

Huston, et al., "Protein engineering of single–chain Fv analogs and fusion proteins", *Meth. Enzymol.* (1991), 203:46–88.

Shu, et al., "Secretion of a single–gene encoded immunoglobulin from myeloma cells", *Proc. Natl. Acad. Sci. USA* (1993), 90:7995–7999.

Skerra, et al., "Assembly of a Functional Immunoglobulin Fv Fragment in *Escherichia coli*", *Science* (1988), 240:1038–1040.

\* cited by examiner

USE OF ADIPSIN/COMPLEMENT FACTOR D IN THE TREATMENT OF METABOLIC RELATED DISORDERS

RELATED APPLICATIONS

This application claims priority from U.S. Provisional Patent Application Ser. No. 60/308,147, filed Jul. 26, 2001, which disclosure is hereby incorporated by reference in its entirety.

FIELD OF THE INVENTION

The present invention relates to the field of metabolic research, in particular the discovery of compounds effective for reducing body mass and useful for treating metabolic-related diseases and disorders. The metabolic-related diseases or disorders envisioned to be treated by the methods of the invention include, but are not limited to, hyperlipidemia, atherosclerosis, insulin resistance, diabetes, and hypertension.

BACKGROUND OF THE INVENTION

The following discussion is intended to facilitate the understanding of the invention, but is not intended nor admitted to be prior art to the invention.

Obesity is a public health problem that is serious, widespread, and increasing. In the United States, 20 percent of the population is obese; in Europe, a slightly lower percentage is obese (Friedman (2000) Nature 404:632–634). Obesity is associated with increased risk of hypertension, cardiovascular disease, diabetes, and cancer as well as respiratory complications and osteoarthritis (Kopelman (2000) Nature 404:635–643). Even modest weight loss ameliorates these associated conditions.

While still acknowledging that lifestyle factors including environment, diet, age and exercise play a role in obesity, twin studies, analyses of familial aggregation, and adoption studies all indicate that obesity is largely the result of genetic factors (Barsh et al (2000) Nature 404:644–651). In agreement with these studies, is the fact that an increasing number of metabolic-related genes are being identified. Some of the more extensively studied genes include those encoding leptin (ob) and its receptor (db), pro-opiomelanocortin (Pomc), melanocortin-4-receptor (Mc4r), agouti protein ($A^y$), carboxypeptidase E (fat), 5-hydroxytryptamine receptor 2C (Htr2c), nescient basic helix-loop-helix 2 (Nhlh2), prohormone convertase 1 (PCSK1), and tubby protein (tubby) (rev'd in Barsh et al (2000) Nature 404:644–651).

SUMMARY OF THE INVENTION

The instant invention is based on Adipsin (also known as complement factor D) polypeptides, which include both the full length polynucleotide sequence and polypeptide fragments thereof, preferably said fragments comprise the active proteolytic domain. More specifically, the biological activities of the Adipsin polypeptides, including fragments, include reduction of elevated free fatty acid levels caused by administration of epinephrine, i.v. injection of "intralipid", or administration of a high fat test meal, as well as increased fatty acid oxidation in muscle cells, reduction in glucose levels, modulation of energy expenditure, decreased resistance to insulin and weight reduction in mammals consuming a high fat/high sucrose diet.

Thus, the invention is drawn to Adipsin polypeptides, polynucleotides encoding said Adipsin polypeptides, vectors comprising said Adipsin polynucleotides, and cells recombinant for said Adipsin polynucleotides, as well as to pharmaceutical and physiologically acceptable compositions comprising said Adipsin polypeptides and methods of administering said Adipsin pharmaceutical and physiologically acceptable compositions in order to reduce body weight or to treat metabolic-related diseases and disorders. Assays for identifying agonists and antagonists of metabolic-related activity are also part of the invention.

In other preferred embodiments, a first aspect, the invention features a purified, isolated, or recombinant Adipsin polypeptides that have lipid partitioning, lipid metabolism, and insulin-like activities. Preferred Adipsin polypeptide fragments have the same or greater activity than a full-length Adipsin polypeptide, wherein said activity is also selected from the group consisting of lipid partitioning, lipid metabolism, and insulin-like activity. In preferred embodiments, said polypeptide fragment comprises, consists essentially of, or consists of, at least 6 consecutive amino acids of the full length polypeptide sequences identified in SEQ ID NOs: 2, 4 or 6. In further preferred embodiments, said polypeptide fragment comprises, consists essentially of, or consists of, amino acids 21–253 or 26–253 of SEQ ID NO: 2 where amino acid 21 of SEQ ID NO: 2 is predicted to be the N-terminal amino acid of the mature Adipsin polypeptide absent the putative signal peptide and amino acid 26 of SEQ ID NO: 2 is predicted to be the N-terminal amino acid of the mature Adipsin polypeptide absent both the putative signal peptide and the putative activation peptide, amino acids 20–253 or 26–253 of SEQ ID NO: 4 where amino acid 20 of SEQ ID NO: 4 is predicted to be the N-terminal amino acid of the mature Adipsin polypeptide absent the putative signal peptide and amino acid 26 of SEQ ID NO: 4 is predicted to be the N-terminal amino acid of the mature Adipsin polypeptide absent both the putative signal peptide and the putative activation peptide, or amino acids 1–228 or 2–228 of SEQ ID NO: 6. In other preferred embodiments, said polypeptide fragment comprises an amino acid sequence at least 80%, 85%, 90%, 91%, 92%, 93%, 94%, 95%, 96%, 97%, 98%, or 99% identical to the corresponding consecutive amino acids of the polypeptide sequences identified in SEQ ID NOs: 2, 4 or 6.

In yet other preferred embodiments, the invention features a purified, isolated, or recombinant Adipsin polypeptides that have activity for reducing smooth muscle cell proliferation and reducing atherosclerosis. Preferred Adipsin polypeptide fragments have the same or greater activity than a full-length Adipsin polypeptide, wherein said activity is also reduction of smooth muscle cell proliferation and reduction of atherosclerosis. In preferred embodiments, said polypeptide fragment comprises, consists essentially of, or consists of, at least 6 consecutive amino acids of the full length polypeptide sequences identified in SEQ ID NOs: 2, 4 or 6. In further preferred embodiments, said polypeptide fragment comprises, consists essentially of, or consists of, amino acids 21–253 or 26–253 of SEQ ID NO: 2 where amino acid 21 of SEQ ID NO: 2 is predicted to be the N-terminal amino acid of the mature Adipsin polypeptide absent the putative signal peptide and amino acid 26 of SEQ ID NO: 2 is predicted to be the N-terminal amino acid of the mature Adipsin polypeptide absent both the putative signal peptide and the putative activation peptide, amino acids 20–253 or 26–253 of SEQ ID NO: 4 where amino acid 20 of SEQ ID NO: 4 is predicted to be the N-terminal amino acid of the mature Adipsin polypeptide absent the putative signal peptide and amino acid 26 of SEQ ID NO: 4 is predicted to be the N-terminal amino acid of the mature Adipsin polypeptide absent both the putative signal peptide and the putative activation peptide, or amino acids 1–228 or 2–228 of SEQ ID NO: 6. In other preferred embodiments, said polypeptide fragment comprises an amino acid sequence at least 80%, 85%, 90%, 91%, 92%, 93%, 94%, 95%, 96%, 97%, 98%, or 99% identical to the corresponding consecutive amino acids of the polypeptide sequences identified in SEQ ID NOs: 2, 4 or 6.

In other highly preferred embodiments, Adipsin polypeptides comprise, consist essentially of, or consist of, a purified, isolated, or a recombinant Adipsin fragment. Preferably, said Adipsin polypeptide comprises, consists essentially of, or consists of, at least 6 consecutive amino acids of the polypeptide sequences identified in SEQ ID NOs: 2, 4 or 6, preferably said fragment comprises a Proteolytic domain. In further preferred embodiments, said polypeptide fragment comprises, consists essentially of, or consists of, amino acids 21–253 or 26–253 of SEQ ID NO: 2 where amino acid 21 of SEQ ID NO: 2 is predicted to be the N-terminal amino acid of the mature Adipsin polypeptide absent the putative signal peptide and amino acid 26 of SEQ ID NO: 2 is predicted to be the N-terminal amino acid of the mature Adipsin polypeptide absent both the putative signal peptide and the putative activation peptide, amino acids 20–253 or 26–253 of SEQ ID NO: 4 where amino acid 20 of SEQ ID NO: 4 is predicted to be the N-terminal amino acid of the mature Adipsin polypeptide absent the putative signal peptide and amino acid 26 of SEQ ID NO: 4 is predicted to be the N-terminal amino acid of the mature Adipsin polypeptide absent both the putative signal peptide and the putative activation peptide, or amino acids 1–228 or 2–228 of SEQ ID NO: 6, preferably said fragment comprises a Proteolytic domain. Alternatively, said Adipsin polypeptide comprises, consists essentially of, or consists of, an amino acid sequence at least 80%, 85%, 90%, 91%, 92%, 93%, 94%, 95%, 96%, 97%, 98%, or 99% identical to the corresponding amino acids from the polypeptide sequences as identified in SEQ ID NOs: 2, 4 or 6.

In a further preferred embodiment, Adipsin polypeptides are able to lower circulating (either blood, serum or plasma) levels (concentration) of: (i) free fatty acids, (ii) glucose, and/or (iii) triglycerides. Further preferred polypeptides of the invention demonstrating free fatty acid level lowering activity, glucose level lowering activity, and/or triglyceride level lowering activity, have an activity that is the same or greater than full length Adipsin polypeptides at the same molar concentration, have the same or greater than transient activity and/or have a sustained activity.

Further preferred Adipsin polypeptides are those that significantly stimulate muscle lipid or free fatty acid oxidation. Further preferred Adipsin polypeptides are those that significantly stimulate muscle lipid or free fatty acid oxidation.

Further preferred Adipsin polypeptides are those that cause C2C12 cells differentiated in the presence of said polypeptides to undergo at least 10%, 20%, 30%, 35%, or 40% more oleate oxidation as compared to untreated cells.

Further preferred Adipsin polypeptides are those that increase leptin uptake in a liver cell line (preferably BPRCL mouse liver cells (ATCC CRL-2217)).

Further preferred Adipsin polypeptides are those that significantly reduce the postprandial increase in plasma free fatty acids due to a high fat meal.

Further preferred Adipsin polypeptides are those that significantly reduce or eliminate ketone body production as the result of a high fat meal.

Further preferred Adipsin polypeptides are those that increase glucose uptake in skeletal muscle cells.

Further preferred Adipsin polypeptides are those that increase glucose uptake in adipose cells.

Further preferred Adipsin polypeptides are those that increase glucose uptake in neuronal cells.

Further preferred Adipsin polypeptides are those that increase glucose uptake in red blood cells.

Further preferred Adipsin polypeptides are those that increase glucose uptake in the brain.

Further preferred Adipsin polypeptides are those that significantly reduce the postprandial increase in plasma glucose following a meal, particularly a high carbohydrate meal.

Further preferred Adipsin polypeptides are those that significantly prevent the postprandial increase in plasma glucose following a meal, particularly a high fat or a high carbohydrate meal.

Further preferred Adipsin polypeptides are those that increase insulin sensitivity.

Further preferred embodiments include heterologous polypeptides comprising one of the Adipsin polypeptides of the invention.

Further preferred embodiments include Adipsin polypeptides that cleave Apm1 (NCBI accession number XP_003191 or U.S. Pat. No. 5,869,330) or ACRP30 (NCBI Q60994 or U.S. Pat. No. 5,869,330).

In a second aspect, the invention features purified, isolated, or recombinant polynucleotides encoding said Adipsin polypeptides described in the first aspect, or the complement thereof. A further preferred embodiment of the invention is a recombinant, purified or isolated polynucleotide comprising, or consisting of a mammalian genomic sequence, gene, or fragments thereof. In one aspect the sequence is derived from a human, mouse or other mammal. In a preferred aspect, the genomic sequence includes isolated, purified, or recombinant polynucleotides comprising a contiguous span of at least 12, 15, 18, 20, 22, 25, 30, 35, 40, 50, 60, 70, 80, 90, 100, 150, 200, 500, 1000, 2000, 5000, 10000 or 50000 nucleotides of any one of the polynucleotide sequences described in SEQ ID NOs: 1, 3 or 5, or the complements thereof, wherein said contiguous span comprises a nucleotide sequence at least 90%, 91%, 92%, 93%, 94%, 95%, 96%, 97%, 98%, or 99% identical to the corresponding nucleotide sequence of the Proteolytic domains as identified in SEQ ID NOs: 1, 3 or 5. In further embodiments the polynucleotides are DNA, RNA, DNA/RNA hybrids, single-stranded, and double-stranded. In a further preferred embodiment, the polynucleotides encode a active proteolytic fragment of adipin, preferably those that cleave Apm1 or ACRP30 polypeptides.

In a third aspect, the invention features a recombinant vector comprising, consisting essentially of, or consisting of, said polynucleotide described in the second aspect.

In a fourth aspect, the invention features a recombinant cell comprising, consisting essentially of, or consisting of, said recombinant vector described in the third aspect. A further embodiment includes a host cell recombinant for a polynucleotide of the invention.

In a fifth aspect, the invention features a pharmaceutical or physiologically acceptable composition comprising, consisting essentially of, or consisting of, said Adipsin polypeptides described in the first aspect and, alternatively, a pharmaceutical or physiologically acceptable diluent.

In a sixth aspect, the invention features a pharmaceutical or physiologically acceptable composition comprising, consisting essentially of, or consisting of, said Adipsin polypeptides described in the first aspect, Apm1 polypeptide and, alternatively, a pharmaceutical or physiologically acceptable diluent.

In a seventh aspect, the invention features the composition of the sixth aspect, wherein said Adipsin polypeptides have proteolytic activity and are allowed to contact said Apm1 polypeptide so as to specifically proteolytically fragment at least 25%, 30%, 35%, 40%, 45%, 50%, 55%, 60%, 65%, 70%, 75%, 80%, 83%, 85%, 87%, 90%, 91%, 92%, 93%, 94%, 95%, 96%, 97%, 98% or 99% of said Apm1 polypeptide.

In an eighth aspect, the invention features a method of reducing body mass comprising providing or administering to individuals in need of reducing body mass said pharmaceutical or physiologically acceptable composition described in the fifth, sixth or seventh aspect.

In preferred embodiments, the identification of said individuals in need of reducing body mass to be treated with said pharmaceutical or physiologically acceptable composition comprises genotyping Adipsin single nucleotide polymorphisms (SNPs) or measuring metabolic polypeptide or mRNA levels in clinical samples from said individuals. Preferably, said clinical samples are selected from the group consisting of plasma, urine, and saliva. Preferably, a Adipsin polypeptide fragment of the present invention is administered to an individual with at least a 10%, 20%, 30%, 40%, 50%, 60%, 70%, 80%, 90%, or 100% reduction in blood, serum or plasma levels of full length any one or all of the Adipsin polypeptides or the naturally proteolytically cleaved Adipsin fragments as compared to healthy, non-obese patients.

In a ninth aspect, the invention features a method of preventing or treating an metabolic-related disease or disorder comprising providing or administering to an individual in need of such treatment said pharmaceutical or physiologically acceptable composition described in the fifth, sixth or seventh aspect. In preferred embodiments, the identification of said individuals in need of such treatment to be treated with said pharmaceutical or physiologically acceptable composition comprises genotyping Adipsin single nucleotide polymorphisms (SNPs) or measuring Adipsin polypeptide or mRNA levels in clinical samples from said individuals. Preferably, said clinical samples are selected from the group consisting of blood, serum, plasma, urine, and saliva. Preferably, said metabolic-related disease or disorder is selected from the group consisting of obesity, insulin resistance, atherosclerosis, atheromatous disease, heart disease, hypertension, stroke, Syndrome X, non-insulin-dependent diabetes and Type II diabetes. Type II diabetes-related complications to be treated by the methods of the invention include microangiopathic lesions, ocular lesions, and renal lesions. Heart disease includes, but is not limited to, cardiac insufficiency, coronary insufficiency, and high blood pressure. Other metabolic-related disorders to be treated by compounds of the invention include hyperlipidemia and hyperuricemia. Yet other metabolic-related diseases or disorders of the invention include cachexia, wasting, AIDS-related weight loss, anorexia, and bulimia. In preferred embodiments, said individual is a mammal, preferably a human.

In related aspects, embodiments of the present invention includes methods of causing or inducing a desired biological response in an individual comprising the steps of: providing or administering to an individual a composition comprising a Adipsin polypeptide, wherein said biological response is selected from the group consisting of:

(a) modulating circulating (either blood, serum, or plasma) levels (concentration) of free fatty acids, wherein said modulating is preferably lowering;

(b) modulating circulating (either blood, serum or plasma) levels (concentration) of glucose, wherein said modulating is preferably lowering;

(c) modulating circulating (either blood, serum or plasma) levels (concentration) of triglycerides, wherein said modulating is preferably lowering;

(d) stimulating muscle lipid or free fatty acid oxidation;

(e) modulating leptin uptake in the liver or liver cells, wherein said modulating is preferably increasing;

(e) modulating the postprandial increase in plasma free fatty acids due to a high fat meal, wherein said modulating is preferably reducing; and, (f) modulating ketone body production as the result of a high fat meal, wherein said modulating is preferably reducing or eliminating;

(g) increasing cell or tissue sensitivity to insulin, particularly muscle, adipose, liver or brain;

and further wherein said biological response is significantly greater than, or at least 10%, 20%, 30%, 35%, 40%, 50% 75% 100% or 500% greater than, the biological response caused or induced by insulin alone at the same molar concentration. In further preferred embodiments, the present invention of said pharmaceutical or physiologically acceptable composition can be used as a method to control blood glucose in some persons with Noninsulin Dependent Diabetes Mellitus (NIDDM, Type II diabetes) in combination with insulin therapy.

In further preferred embodiments, the present invention of said pharmaceutical or physiologically acceptable composition can be used as a method to control blood glucose in some persons with Insulin Dependent Diabetes Mellitus (IDDM, Type I diabetes) in combination with insulin therapy.

In further preferred embodiments, the present invention of said pharmaceutical or physiologically acceptable composition can be used as a method to control body weight in some persons with Noninsulin Dependent Diabetes Mellitus (NIDDM, Type II diabetes) in combination with insulin therapy.

In further preferred embodiments, the present invention of said pharmaceutical or physiologically acceptable composition can be used as a method to control body weight in some persons with Insulin Dependent Diabetes Mellitus (IDDM, Type I diabetes) in combination with insulin therapy.

In further preferred embodiments, the present invention of said pharmaceutical or physiologically acceptable composition can be used as a method to control blood glucose in some persons with Noninsulin Dependent Diabetes Mellitus (NIDDM, Type II diabetes) alone, without combination of insulin therapy.

In further preferred embodiments, the present invention of said pharmaceutical or physiologically acceptable composition can be used as a method to control blood glucose in some persons with Insulin Dependent Diabetes Mellitus (IDDM, Type I diabetes) alone, without combination of insulin therapy.

In further preferred embodiments, the present invention of said pharmaceutical or physiologically acceptable composition can be used as a method to control body weight in some persons with Noninsulin Dependent Diabetes Mellitus (NIDDM, Type II diabetes) alone, without combination of insulin therapy.

In further preferred embodiments, the present invention of said pharmaceutical or physiologically acceptable composition can be used as a method to control body weight in some persons with Insulin Dependent Diabetes Mellitus (IDDM, Type I diabetes) alone, without combination of insulin therapy.

In a further preferred embodiment, the present invention may be used in complementary therapy of NIDDM patients to improve their weight or glucose control in combination with an insulin secretagogue (preferably oral form) or an insulin sensitising (preferably oral form) agent. Preferably, the oral insulin secretagogue is 1,1-dimethyl-2-(2-morpholino phenyl)guanidine fumarate (BTS67582) or a sulphonylurea selected from tolbutamide, tolazamide, chlorpropamide, glibenclamide, glimepiride, glipizide and glidazide. Preferably, the insulin sensitising agent is selected from metformin, ciglitazone, troglitazone and pioglitazone.

The present invention further provides a method of improving the body weight or glucose control of NIDDM patients alone, without an insulin secretagogue or an insulin sensitising agent.

In a further preferred embodiment, the present invention may be used in complementary therapy of IDDM patients to improve their weight or glucose control in combination with an insulin secretagogue (preferably oral form) or an insulin sensitising (preferably oral form) agent. Preferably, the insulin secretagogue is 1,1-dimethyl-2-(2-morpholino phenyl)guanidme fumarate (BTS67582) or a sulphonylurea selected from tolbutamide, tolazamide, chlorpropamide, glibenclamide, glimepiride, glipizide and glidazide. Preferably, the insulin sensitising agent is selected from metformin, ciglitazone, troglitazone and pioglitazone.

The present invention further provides a method of improving the body weight or glucose control of IDDM patients alone, without an insulin secretagogue or an insulin sensitising agent.

In a further preferred embodiment, the present invention may be administered either concomitantly or concurrently, with the insulin secretagogue or insulin sensitising agent for example in the form of separate dosage units to be used simultaneously, separately or sequentially (either before or after the secretagogue or either before or after the sensitising agent). Accordingly, the present invention further provides for a composition of pharmaceutical or physiologically acceptable composition and an insulin secretagogue or insulin sensitising agent as a combined preparation for simultaneous, separate or sequential use for the improvement of body weight or glucose control in NIDDM or IDDM patients.

In further preferred embodiments, the present invention of said pharmaceutical or physiologically acceptable composition further provides a method for the use as an insulin sensitiser.

In further preferred embodiments, the present invention of said pharmaceutical or physiologically acceptable composition can be used as a method to improve insulin sensitivity in some persons with Noninsulin Dependent Diabetes Mellitus (NIDDM, Type II diabetes) in combination with insulin therapy.

In further preferred embodiments, the present invention of said pharmaceutical or physiologically acceptable composition can be used as a method to improve insulin sensitivity in some persons with Insulin Dependent Diabetes Mellitus (IDDM, Type I diabetes) in combination with insulin therapy.

In further preferred embodiments, the present invention of said pharmaceutical or physiologically acceptable composition can be used as a method to improve insulin sensitivity in some persons with Noninsulin Dependent Diabetes Mellitus (NIDDM, Type II diabetes) without insulin therapy.

In a tenth aspect, the invention features a method of making the Adipsin polypeptide described in the first aspect, wherein said method is selected from the group consisting of: proteolytic cleavage, recombinant methodology and artificial synthesis.

In an eleventh aspect, the present invention provides a method of making a recombinant Adipsin polypeptide fragment or a full length Adipsin polypeptide, the method comprising providing a transgenic, non-human mammal whose milk contains said recombinant Adipsin polypeptide fragment or full-length protein, and purifying said recombinant Adipsin polypeptide fragment or said full-length Adipsin polypeptide from the milk of said non-human mammal. In one embodiment, said non-human mammal is a cow, goat, sheep, rabbit, or mouse. In another embodiment, the method comprises purifying a recombinant full-length Adipsin polypeptide from said milk, and further comprises cleaving said protein in vitro to obtain a desired Adipsin polypeptide fragment.

In a twelfth aspect, the invention features a purified or isolated antibody capable of specifically binding to a polypeptide of the present invention. In one aspect of this embodiment, the antibody is capable of binding to a polypeptide comprising at least 6 consecutive amino acids, at least 8 consecutive amino acids, or at least 10 consecutive amino acids of the sequence of one of the polypeptide sequences described in SEQ ID NOs: 2, 4 or 6.

In a thirteenth aspect, the invention features a use of the polypeptide described in the first aspect for treatment of metabolic-related diseases and disorders and/or reducing or increasing body mass. Preferably, said metabolic-related diseases and disorders are selected from the group consisting of obesity, insulin resistance, atherosclerosis, atheromatous disease, heart disease, hypertension, stroke, Syndrome X, non-insulin-dependent diabetes and Type II diabetes. Type II diabetes-related complications to be treated by the methods of the invention include microangiopathic lesions, ocular lesions, and renal lesions. Heart disease includes, but is not limited to, cardiac insufficiency, coronary insufficiency, and high blood pressure. Other metabolic-related disorders to be treated by compounds of the invention include hyperlipidemia and hyperuricemia. Yet other metabolic-related diseases or disorders of the invention include cachexia, wasting, AIDS-related weight loss, anorexia, and bulimia. In preferred embodiments, said individual is a mammal, preferably a human.

In a fourteenth aspect, the invention provides a polypeptide of the first aspect of the invention, or a composition of the fifth, sixth or seventh aspect of the invention, for use in a method of treatment of the human or animal body.

In a fifteenth aspect, the invention features methods of reducing body weight for cosmetic purposes comprising providing to an individual said pharmaceutical or physiologically acceptable composition described in the fifth aspect, or a polypeptide described in the first aspect. Preferably, for said reducing body weight said individual has a BMI of at least 20 and no more than 25. Alternatively, for said increasing body weight said individual preferably has a BMI of at least 15 and no more than 20.

In a sixteenth aspect, the invention features the pharmaceutical or physiologically acceptable composition described in the fifth, sixth or seventh aspect for reducing body mass and/or for treatment or prevention of metabolic-related diseases or disorders. Preferably, said metabolic-related disease or disorder is selected from the group consisting of obesity, insulin resistance, atherosclerosis, atheromatous disease, heart disease, hypertension, stroke, Syndrome X, non-insulin-dependent diabetes and Type II diabetes. Type II diabetes-related complications to be treated by the methods of the invention include microangiopathic lesions, ocular lesions, and renal lesions. Heart disease includes, but is not limited to, cardiac unsufficiency, coronary insufficiency, and high blood pressure. Other metabolic-related disorders to be treated by compounds of the invention include hyperlipidemia and hyperuricemia. Yet other metabolic-related diseases or disorders of the invention include cachexia, wasting, AIDS-related weight loss, anorexia, and bulimia. In preferred embodiments, said individual is a mammal, preferably a human. In preferred embodiments, the identification of said individuals to be treated with said pharmaceutical or physiologically acceptable composition comprises genotyping Adipsin single nucleotide polymorphisms (SNPs) or measuring Adipsin polypeptide or mRNA levels in clinical samples from said individuals. Preferably, said clinical samples are selected from the group consisting of blood, serum, plasma, urine, and saliva.

In a seventeenth aspect, the invention features the pharmaceutical or physiologically acceptable composition described in the fifth, sixth or seventh aspect for reducing body weight for cosmetic reasons.

In an eighteenth aspect, the invention features methods of treating insulin resistance comprising providing to an individual said pharmaceutical or physiologically acceptable composition described in the fifth, sixth or seventh aspect, or a polypeptide described in the first aspect.

In a nineteenth aspect, the invention features methods of treating atherosclerosis comprising providing to an individual said pharmaceutical or physiologically acceptable composition described in the fifth, sixth or seventh aspect, or a polypeptide described in the first aspect.

In a preferred aspect of the methods above and disclosed herein, the amount of Adipsin polypeptide or polynucleotide administered to an individual is sufficient to bring circulating (blood, serum, or plasma) levels (concentration) of Adipsin polypeptides to their normal levels (levels in non-obese individuals). "Normal levels" may be specified as the total concentration of all circulating Adipsin polypeptides (full length Adipsin proteins and fragments thereof) or the concentration of all circulating proteolytically cleaved Adipsin polypeptides only.

In a further preferred aspect of the methods above and disclosed herein, weight loss is due in part or in whole to a decrease in mass of 1) subcutaneous adipose tissue and/or 2) viseral (omental) adipose tissue.

In a further preferred aspect of the present invention, the Adipsin polypeptides of the present invention, including pharmaceutical and physiological compositions thereof, are used in methods to cleave Apm1 or ACRP30, said methods comprising the steps of contacting Apm1 or ACRP30 with an Adipsin polypeptide under conditions the permit proteolytic cleavage of said Apm1 or ACRP30 by said Adipsin. In a preferred embodiment, the Apm1 or ACRP30 polypeptide is in an individual and is contacted by Adipsin by administering to said individual an Adipsin polypeptides of the present invention. In another preferred embodiment, the Apm1 polypeptide is an endogenous Apm1 polypeptide. In another preferred embodiment, the Apm1 polypeptide, including fragments thereof, is administered to said individual, wherein said administration is before, after, or concurrently with administration of said Adipsin polypeptide.

Any of the methods, or specific embodiments of methods of the present invention may be specifically excluded, including methods of treating and embodiments thereof. For example, obese people may be specifically excluded from a method of the present invention. Moreover, embodiments of the methods may be combined in any combination. For example, a method may include limitations such as a person who is diabetic (type I or type II) or suffering with insulin resistance, who is also obese. Alternatively, the person may be obese and suffering from another disease or disorder disclosed herein.

Structure of Adipsin Polypeptide

The full-length Adipsin polypeptide is comprised of distinct regions including:

1. an N-terminal putative signal peptide comprising amino acids from about amino acids 1–20 of SEQ ID NO: 2, or comprising amino acids from about amino acids 1–19 of SEQ ID NO: 4;
2. a putative activation peptide comprising amino acids from about amino acids 21–25 of SEQ ID NO: 2, or comprising amino acids from about amino acids 20–25 of SEQ ID NO: 4; and
3. a region required for serine protease activity comprising amino acids from about amino acids 26–253 of SEQ ID NOs: 2 or 4, or comprising amino acids from about amino acids 1–228 of SEQ ID NO: 6.

BRIEF DESCRIPTION OF SEQUENCE LISTING

SEQ ID NOs: 1, 3 or 5 are the nucleotide sequence of cDNA with an open reading frame which location is indicated as features. When appropriate, the locations of the potential polyadenylation site and polyadenylation signal are also indicated.

SEQ ID NOs: 2, 4 or 6 are the amino acid sequences of protein encoded by the cDNA of SEQ ID NOs: 1, 3 or 5, respectively.

The appended Sequence Listing is hereby incorporated by reference in its entirety.

DETAILED DESCRIPTION OF THE INVENTION

Before describing the invention in greater detail, the following definitions are set forth to illustrate and define the meaning and scope of the terms used to describe the invention herein.

As used interchangeably herein, the terms "oligonucleotides", and "polynucleotides" and nucleic acid include RNA, DNA, or RNA/DNA hybrid sequences of more than one nucleotide in either single chain or duplex form. The terms encompass "modified nucleotides" which comprise at least one modification, including by way of example and not limitation: (a) an alternative linking group, (b) an analogous form of purine, (c) an analogous form of pyrimidine, or (d) an analogous sugar. For examples of analogous linking groups, purines, pyrimidines, and sugars see for example PCT publication No. WO 95/04064. The polynucleotide sequences of the invention may be prepared by any known method, including synthetic, recombinant, ex vivo generation, or a combination thereof, as well as utilizing any purification methods known in the art.

The terms polynucleotide construct, recombinant polynucleotide and recombinant polypeptide are used herein consistently with their use in the art. The terms "upstream" and "downstream" are also used herein consistently with their use in the art. The terms "base paired" and "Watson & Crick base paired" are used interchangeably herein and consistently with their use in the art. Similarly, the terms "complementary", "complement thereof", "complement", "complementary polynucleotide", "complementary nucleic acid" and "complementary nucleotide sequence" are used interchangeably herein and consistently with their use in the art.

The term "purified" is used herein to describe a polynucleotide or polynucleotide vector of the invention that has been separated from other compounds including, but not limited to, other nucleic acids, carbohydrates, lipids and proteins (such as the enzymes used in the synthesis of the polynucleotide). Purified can also refer to the separation of covalently closed polynucleotides from linear polynucleotides, or vice versa, for example. A polynucleotide is substantially pure when at least about 50%, 60%, 75%, or 90% of a sample contains a single polynucleotide sequence. In some cases this involves a determination between conformations (linear versus covalently closed). A substantially pure polynucleotide typically comprises about 50, 60, 70, 80, 90, 95, 99% weight/weight of a nucleic acid sample. Polynucleotide purity or homogeneity may be indicated by a number of means well known in the art, such as agarose or polyacrylamide gel electrophoresis of a sample, followed by visualizing a single polynucleotide band upon staining the gel. For certain purposes higher resolution can be provided by using HPLC or other means well known in the art.

Similarly, the term "purified" is used herein to describe a polypeptide of the invention that has been separated from other compounds including, but not limited to, nucleic acids, lipids, carbohydrates and other proteins. In some preferred embodiments, a polypeptide is substantially pure when at least about 50%, 60%, 75%, 85%, 90%, 95%, 96%, 97%, 98%, 99%, or 99.5% of the polypeptide molecules of a sample have a single amino acid sequence. In some preferred embodiments, a substantially pure polypeptide typically comprises about 50%, 60%, 70%, 80%, 90% 95%, 96%, 97%, 98%, 99% or 99.5% weight/weight of a protein sample. Polypeptide purity or homogeneity is indicated by a number of methods well known in the art, such as agarose or polyacrylamide gel electrophoresis of a sample, followed by visualizing a single polypeptide band upon staining the gel. For certain purposes higher resolution can be provided by using HPLC or other methods well known in the art.

Further, as used herein, the term "purified" does not require absolute purity; rather, it is intended as a relative definition. Purification of starting material or natural material to at least one order of magnitude, preferably two or three orders, and more preferably four or five orders of magnitude is expressly contemplated. Alternatively, purification may be expressed as "at least" a percent purity relative to heterologous polynucleotides (DNA, RNA or both) or polypeptides. As a preferred embodiment, the polynucleotides or polypeptides of the present invention are at least; 10%, 20%, 30%, 40%, 50%, 60%, 70%, 80%, 90%, 95%, 96%, 96%, 98%, 99%, 99.5% or 100% pure relative to heterologous polynucleotides or polypeptides. As a further preferred embodiment the polynucleotides or polypeptides have an "at least" purity ranging from any number, to the thousandth position, between 90% and 100% (e.g., at least 99.995% pure) relative to heterologous polynucleotides or polypeptides. Additionally, purity of the polynucleotides or polypeptides may be expressed as a percentage (as described above) relative to all materials and compounds other than the carrier solution. Each number, to the thousandth position, may be claimed as individual species of purity.

The term "isolated" requires that the material be removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment.

Specifically excluded from the definition of "isolated" are: naturally occurring chromosomes (e.g., chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a 5' EST makes up less than 5% (or alternatively 1%, 2%, 3%, 4%, 10%, 25%, 50%, 75%, or 90%, 95%, or 99%) of the number of nucleic acid inserts in the vector molecules. Further specifically excluded are whole cell genomic DNA or whole cell RNA preparations (including said whole cell preparations which are mechanically sheared or enzymatically digested). Further specifically excluded are the above whole cell preparations as either an in vitro preparation or as a heterogeneous mixture separated by electrophoresis (including blot transfers of the same) wherein the polynucleotide of the invention have not been further separated from the heterologous polynucleotides in the electrophoresis medium (e.g., further separating by excising a single band from a heterogeneous band population in an agarose gel or nylon blot).

The term "primer" denotes a specific oligonucleotide sequence which is complementary to a target nucleotide sequence and used to hybridize to the target nucleotide sequence. A primer serves as an initiation point for nucleotide polymerization catalyzed by DNA polymerase, RNA polymerase, or reverse transcriptase.

The term "probe" denotes a defined nucleic acid segment (or nucleotide analog segment, e.g., PNA as defined hereinbelow) which can be used to identify a specific polynucleotide sequence present in a sample, said nucleic acid segment comprising a nucleotide sequence complementary to the specific polynucleotide sequence to be identified.

The term "polypeptide" refers to a polymer of amino acids without regard to the length of the polymer. Thus, peptides, oligopeptides, and proteins are included within the definition of polypeptide. This term also does not specify or exclude post-expression modifications of polypeptides. For example, polypeptides that include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

Without being limited by theory, the compounds/polypeptides of the invention are capable of modulating the partitioning of dietary lipids between the liver and peripheral tissues, and are thus believed to treat "diseases involving the partitioning of dietary lipids between the liver and peripheral tissues." The term "peripheral tissues" is meant to include muscle and adipose tissue. In preferred embodiments, the compounds/polypeptides of the invention partition the dietary lipids toward the muscle. In alternative preferred embodiments, the dietary lipids are partitioned toward the adipose tissue. In other preferred embodiments, the dietary lipids are partitioned toward the liver. In yet other preferred embodiments, the compounds/polypeptides of the invention increase or decrease the oxidation of dietary lipids, preferably free fatty acids (FFA) by the muscle. Dietary lipids include, but are not limited to triglycerides and free fatty acids.

Preferred diseases believed to involve the partitioning of dietary lipids include obesity and obesity-related diseases and disorders such as obesity, insulin resistance, atherosclerosis, atheromatous disease, heart disease, hypertension, stroke, Syndrome X, Nonisulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, and renal lesions. Heart disease includes, but is not limited to, cardiac insufficiency, coronary insufficiency, and high blood pressure. Other obesity-related disorders to be treated by compounds of the invention include hyperlipidemia and hyperuricemia. Yet other obesity-related diseases or disorders of the invention include cachexia, wasting, AIDS-related weight loss, anorexia, and bulimia.

The term "heterologous", when used herein, is intended to designate any polypeptide or polynucleotide other than a Adipsin polypeptide or a polynucleotide encoding a Adipsin polypeptide of the present invention.

The terms "comprising", "consisting of" and "consisting essentially of" are defined according to their standard meaning. A defined meaning set forth in the M.P.E.P. controls over a defined meaning in the art and a defined meaning set forth in controlling Federal Circuit case law controls over a meaning set forth in the M.P.E.P. With this in mind, the terms may be substituted for one another throughout the instant application in order to attach the specific meaning associated with each term.

The term "host cell recombinant for" a particular polynucleotide of the present invention, means a host cell that has been altered by the hands of man to contain said polynucleotide in a way not naturally found in said cell. For example, said host cell may be transiently or stably transfected or transduced with said polynucleotide of the present invention.

The term "obesity" as used herein is defined in the WHO classifications of weight (Kopelman (2000) Nature 404:635643). Underweight is less than 18.5 (thin); Healthy is 18.5–24.9 (normal); grade 1 overweight is 25.0–29.9 (overweight); grade 2 overweight is 30.0–39.0 (obesity); grade 3 overweight is greater than or equal to 40.0 BMI. BMI is body mass index (morbid obesity) and is $kg/m^2$. Waist circumference can also be used to indicate a risk of metabolic complications where in men a circumference of greater than or equal to 94 cm indicates an increased risk, and greater than or equal to 102 cm indicates a substantially increased risk. Similarly for women, greater than or equal to 88 cm indicates an increased risk, and greater than or equal to 88 cm indicates a substantially increased risk. The waist circumference is measured in cm at midpoint between lower border of ribs and upper border of the pelvis. Other measures of obesity include, but are not limited to, skinfold thickness which is a measurement in cm of skinfold thickness using calipers, and bioimpedance, which is based on the principle that lean mass conducts current better than fat mass because it is primarily an electrolyte solution; measurement of resistance to a weak current (impedance) applied across extremities provides an estimate of body fat using an empirically derived equation.

The term "agent acting on the partitioning of dietary lipids between the liver and peripheral tissues" refers to a compound or polypeptide of the invention that modulates the partitioning of dietary lipids between the liver and the peripheral tissues as previously described. Preferably, the agent increases or decreases the oxidation of dietary lipids, preferably free fatty acids (FFA) by the muscle. Preferably the agent decreases or increases the body weight of individuals or is used to treat or prevent an obesity-related disease or disorder such as obesity, insulin resistance, atherosclerosis, atheromatous disease, heart disease, hypertension, stroke, Syndrome X, Noninsulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, renal lesions. Heart disease includes, but is not limited to, cardiac insufficiency, coronary insufficiency, and high blood pressure. Other obesity-related disorders to be treated by compounds of the invention include hyperlipidemia and hyperuricemia. Yet other obesity-related diseases or disorders of the invention include cachexia, wasting, AIDS-related weight loss, anorexia, and bulimia.

The terms "response to an agent acting on the partitioning of dietary lipids between the liver and peripheral tissues" refer to drug efficacy, including but not limited to, ability to metabolize a compound, ability to convert a pro-drug to an active drug, and the pharmacokinetics (absorption, distribution, elimination) and the pharmacodynamics (receptor-related) of a drug in an individual.

The terms "side effects to an agent acting on the partitioning of dietary lipids between the liver and peripheral tissues" refer to adverse effects of therapy resulting from extensions of the principal pharmacological action of the drug or to idiosyncratic adverse reactions resulting from an interaction of the drug with unique host factors. "Side effects to an agent acting on the partitioning of dietary lipids between the liver and peripheral tissues" can include, but are not limited to, adverse reactions such as dermatologic, hematologic or hepatologic toxicities and further includes gastric and intestinal ulceration, disturbance in platelet function, renal injury, nephritis, vasomotor rhinitis with profuse watery secretions, angioneurotic edema, generalized urticaria, and bronchial asthma to laryngeal edema and bronchoconstriction, hypotension, and shock.

The term "Adipsin-related diseases and disorders" as used herein refers to any disease or disorder comprising an aberrant functioning of a Adipsin, or which could be treated or prevented by modulating Adipsin levels or activity. "Aberrant functioning of a Adipsin" includes, but is not limited to, aberrant levels of expression of a Adipsin (either increased or decreased, but preferably decreased), aberrant activity of a Adipsin (either increased or decreased), and aberrant interactions with ligands or binding partners (either increased or decreased). By "aberrant" is meant a change from the type, or level of activity seen in normal cells, tissues, or patients, or seen previously in the cell, tissue, or patient prior to the onset of the illness. In preferred embodiments, these Adipsin-related diseases and disorders include obesity and the metabolic-related diseases and disorders described previously.

The term "cosmetic treatments" is meant to include treatments with compounds or polypeptides of the invention that increase or decrease the body mass of an individual where the individual is not clinically obese or clinically thin. Thus, these individuals have a body mass index (BMI) below the cut-off for clinical obesity (e.g. below 25 kg/m$^2$) and above the cut-off for clinical thinness (e.g. above 18.5 kg/m$^2$). In addition, these individuals are preferably healthy (e.g. do not have an metabolic-related disease or disorder of the invention). "Cosmetic treatments" are also meant to encompass, in some circumstances, more localized increases in adipose tissue, for example, gains or losses specifically around the waist or hips, or around the hips and thighs, for example. These localized gains or losses of adipose tissue can be identified by increases or decreases m waist or hip size, for example.

The term "preventing" as used herein refers to administering a compound prior to the onset of clinical symptoms of a disease or condition so as to prevent a physical manifestation of aberrations associated with obesity or a Adipsin.

The term "treating" as used herein refers to administering a compound after the onset of clinical symptoms.

The term "in need of treatment" as used herein refers to a judgment made by a caregiver (e.g. physician, nurse, nurse practitioner, etc in the case of humans; veterinarian in the case of animals, including non-human mammals) that an individual or animal requires or will benefit from treatment. This judgment is made based on a variety of factors that are in the realm of a caregiver's expertise, but that include the knowledge that the individual or animal is ill, or will be ill, as the result of a condition that is treatable by the compounds of the invention.

The term "perceives a need for treatment" refers to a sub-clinical determination that an individual desires to reduce weight for cosmetic reasons as discussed under "cosmetic treatment" above. The term "perceives a need for treatment" in other embodiments can refer to the decision that an owner of an animal makes for cosmetic treatment of the animal.

The term "individual" or "patient" as used herein refers to any animal, including mammals, preferably mice, rats, other rodents, rabbits, dogs, cats, swine, cattle, sheep, horses, or primates, and most preferably humans. The term may specify male or female or both, or exclude male or female.

The term "non-human animal" refers to any non-human vertebrate, including birds and more usually mammals, preferably primates, animals such as swine, goats, sheep, donkeys, horses, cats, dogs, rabbits or rodents, more preferably rats or mice. Both the terms "animal" and "mammal" expressly embrace human subjects unless preceded with the term "non-human".

The inventors believe Adipsin polypeptides are able to significantly reduce the postprandial response of plasma free fatty acids, glucose, and triglycerides in mice fed a high fat/sucrose meal, while not affecting levels of leptin, insulin or glucagon. In addition, it is believed Adipsin polypeptides modulate muscle free fatty acid oxidation in vitro and ex vivo, preferably increase oxidation. Further, Adipsin polypeptides of the invention are believed to modulate weight gain in mice that are fed a high fat/sucrose diet.

The instant invention encompasses the use of Adipsin polypeptides in the partitioning of free fatty acid (FFA) and as an important new tool to control energy homeostasis. Of the tissues that can significantly remove lipids from circulation and cause FFA oxidation, muscle is believed to be quantitatively the most important. . .

PREFERRED EMBODIMENTS OF THE INVENTION

I. Adipsin Polypeptides of the Invention

Adipsin polypeptides that have measurable activity in vitro and in vivo have been identified. Preferred Adipsin polypeptides are those of SEQ ID NOs: 2, 4 and 6. Further preferred Adipsin polypeptides include amino acids 21–253 or 26–253 of SEQ ID NO: 2 where amino acid 21 of SEQ ID NO: 2 is predicted to be the N-terminal amino acid of the mature Adipsin polypeptide absent the putative signal peptide and amino acid 26 of SEQ ID NO: 2 is predicted to be the N-terminal amino acid of the mature Adipsin polypeptide absent both the putative signal peptide and the putative activation peptide, amino acids 20–253 or 26–253 of SEQ ID NO: 4 where amino acid 20 of SEQ ID NO: 4 is predicted to be the N-terminal amino acid of the mature Adipsin polypeptide absent the putative signal peptide and amino acid 26 of SEQ ID NO: 4 is predicted to be the N-terminal amino acid of the mature Adipsin polypeptide absent both the putative signal peptide and the putative activation peptide, or amino acids 1–228 or 2–228 of SEQ ID NO: 6. Further preferred Adipsin polypeptides are those with increased activity. For example, included in the present invention are Adipsin polypeptides of SEQ ID NOs :2 or 4 wherein Ser203 is replaced by Tyr, Thr223 is replaced with Ser, and Ser224 is replaced with Trp and Adipsin polypeptides of SEQ ID NO: 6 wherein Ser178 is replaced by Tyr, Thr198 is replaced with Ser, and Ser199 is replaced with Trp. Included are polypeptides with one, two or all three of the substitutions, wherein each possible combination is included as an individual species of the present invention. Methods for making other substitutions and other modifications are well known in the art as are methods for measuring Adipsin activity (See e.g., Kim, S. J. Biol. Chem. 270(41): 24399–24405(1995), Volanakis, J. E., Protein Science 5:553–564 (1996), incorporated by reference herein in their entireties. Preferred Adipsin biological activities as a result of its function as a protease, include, but are not limited to, modulation, preferably reduction, of the postprandial response of plasma free fatty acids, glucose, and triglycerides in mice fed a high fat/sucrose meal, change; preferably a reduction of insulin resistance; preferably a reduction in smooth muscle cell proliferation and atherosclerosis; preferably an increase, in muscle free fatty acid oxidation in vitro and ex vivo; and sustained weight loss in mice on a high fat/sucrose diet. Other assays for Adipsin polypeptide activity in vitro and in vivo are also provided (Examples 2, 5, 7, 9, 11, for example), and equivalent assays can be designed by those with skill in the art.

The term "Adipsin polypeptides" includes both the "full-length" polypeptide and fragments of the "full-length" Adipsin polypeptides (although each of the above species may be particularly specified).

By "intact" or "full-length" Adipsin polypeptide as used herein is meant the full length polypeptide sequence of any Adipsin polypeptide, from the N-terminal methionine to the C-terminal stop codon. Examples of intact or full length Adipsin polypeptides are found in the sequence listing.

The term "metabolic-related activity" as used herein refers to at least one, and preferably all, of the activities described herein for Adipsin polypeptides. Assays for the determination of these activities are provided herein (See e.g. Examples section), and equivalent assays can be designed by those with ordinary skill in the art. Optionally, "metabolic-related activity" can be selected from the group consisting of lipid partitioning, lipid metabolism, and insulin-like activity, or an activity within one of these categories. By "lipid partitioning" activity is meant the ability to effect the location of dietary lipids among the major tissue groups including, adipose tissue, liver, and muscle. The inventors believe that Adipsin polypeptides of the invention play a role in the partitioning of lipids to the muscle, liver or adipose tissue. By "lipid metabolism" activity is meant the ability to influence the metabolism of lipids. The inventors believe that Adipsin polypeptides of the invention have the ability to affect the level of free fatty acids in the plasma as well as to modulate, preferably increase, the metabolism of lipids in the muscle through free fatty acid oxidation experiments (Examples 2, 6, 8, 9, 10) and to transiently affect the levels of triglycerides in the plasma and the muscle (Examples 6, 8, 11). By "insulin-like" activity is meant the ability of Adipsin polypeptides to modulate the levels of glucose in the plasma. The inventors believe that Adipsin polypeptides do not significantly impact insulin levels but do impact glucose levels similarly to the effects of insulin (Examples 7 & 8). These effects may vary in the presence of the intact (full-length) Adipsin polypeptides or are significantly greater in the presence of the Adipsin polypeptide fragments compared with the full-length Adipsin polypeptides.

The term "significantly greater" as used herein refers to a comparison of the activity of a Adipsin polypeptide in an metabolic-related assay compared with untreated cells in the same assay. By "significantly" as used herein is meant statistically significant as it is typically determined by those with ordinary skill in the art. For example, data are typically calculated as a mean±SEM, and a p-value <0.05 is considered statistically significant. Statistical analysis is typically done using either the unpaired Student's t test or the paired Student's t test, as appropriate in each study. Examples of a significant change in activity as a result of the presence of a Adipsin polypeptide of the invention compared to untreated cells include an increase or a decrease in a given parameter of at least 5%, 10%, 15%, 20%, 25%, 30%, 35%, 40%, 45%, 50%, 55%, 60%, 65%, 70%, or 75%. One or more, but not necessarily all, of the measurable parameters will change significantly in the presence of Adipsin polypeptide as compared to untreated cells.

Representative "metabolic-related assays" are provided in the Examples. These assays include, but are not limited to, methods of measuring the postprandial response, methods of measuring free fatty acid oxidation, and methods of measuring weight modulation. In preferred embodiments, the post-prandial response is measured in non-human animals, preferably mice. In preferred embodiments changes in dietary lipids are measured, preferably free fatty acids and/or triglycerides. In other embodiments, other physiologic parameters are measured including, but not limited to, levels of glucose, insulin, and leptin. In other preferred embodiments, free fatty acid oxidation is measured in cells in vitro or ex vivo, preferably in muscle cells or tissue of non-human animals, preferably mice. In yet other preferred embodiments weight modulation is measured in human or non-human animals, preferably rodents (rats or mice), primates, canines, felines or procines. on a high fat/sucrose diet. Optionally, "metabolic-related activity" includes other activities not specifically identified herein. In general, "measurable parameters" relating to obesity and the field of metabolic research can be selected from the group consisting of free fatty acid levels, free fatty acid oxidation, triglyceride levels, glucose levels, insulin levels, leptin levels, food intake, weight, leptin and lipoprotein binding, uptake and degradation and LSR expression.

In these metabolic-related assays, preferred Adipsin polypeptides would cause a significant change in at least one of the measurable parameters selected from the group consisting of post-prandial lipemia, free fatty acid levels, triglyceride levels, glucose levels, free fatty acid oxidation, and weight. Alternatively, preferred Adipsin polypeptides would have a significant change in at least one of the measurable parameters selected from the group consisting of an increase in LSR activity, an increase in leptin activity and an increase in lipoprotein activity. By "LSR" activity is meant expression of LSR on the surface of the cell, or in a particular conformation, as well as its ability to bind, uptake, and degrade leptin and lipoprotein. By "leptin" activity is meant its binding, uptake and degradation by LSR, as well as its transport across a blood brain barrier, and potentially these occurrences where LSR is not necessarily the mediating factor or the only mediating factor. Similarly, by "lipoprotein" activity is meant its binding, uptake and degradation by LSR, as well as these occurrences where LSR is not necessarily the mediating factor or the only mediating factor.

The invention is drawn, inter alia, to isolated, purified or recombinant Adipsin polypeptides. Adipsin polypeptides of the invention are useful for reducing or increasing (using antagonists of Adipsin polypeptides) body weight either as a cosmetic treatment or for treatment or prevention of metabolic-related diseases and disorders. Adipsin polypeptides are also useful inter alia in screening assays for agonists or antagonists of Adipsin polypeptide activity, for raising Adipsin polypeptide-specific antibodies, and in diagnostic assays.

The Adipsin polypeptides of the present invention are preferably provided in an isolated form, and may be partially or substantially purified. A recombinantly produced version of any one of the Adipsin polypeptides can be substantially purified by the one-step method described by Smith et al. ((1988) Gene 67(1):31–40) or by the methods described herein or known in the art. Polypeptides of the invention also can be purified from natural or recombinant sources using antibodies directed against the polypeptides of the invention by methods known in the art of protein purification.

Preparations of Adipsin polypeptides of the invention involving a partial purification of or selection for the Adipsin polypeptides are also specifically contemplated. These crude to preparations are envisioned to be the result of the concentration of cells expressing Adipsin polypeptides with perhaps a few additional purification steps, but prior to complete purification of the fragment. The cells expressing Adipsin polypeptides are present in a pellet, they are lysed, or the crude polypeptide is lyophilized, for example.

Adipsin polypeptides can be any integer in length from at least 6 consecutive amino acids to the number of amino acids of the full length Adipsin polypeptide. Thus, for the polypeptide of SEQ ID NOs: 2 or 4, a Adipsin polypeptide can be any integer of consecutive amino acids from 6 to 253 or 6 to 228 for SEQ ID NO: 6, for example. The term "integer" is used herein in its mathematical sense and thus representative integers include, but are not limited to: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 234, 235, 236, 237, 238, 239, 240, 241, 242, 243, 244, 245, 246, 247, 248, 249, 250, 251, 252, and 253.

Each Adipsin polypeptide as described above can be further specified in terms of its N-terminal and C-terminal positions. For example, every combination of a N-terminal and C-terminal position that fragments of from 6 contiguous amino acids to 1 amino acids less than the full length Adipsin polypeptide could occupy, on any given intact and contiguous full length Adipsin polypeptide sequence are included in the present invention. Thus, a 6 consecutive amino acid fragment could occupy positions selected from the group consisting of 1–6, 2–7, 3–8, 4–9, 5–10, 6–11, 7–12, 8–13, 9–14, 10–15, 11–16, 12–17, 13–18, 14–19, 15–20, 16–21, 17–22, 18–23, 19–24, 20–25, 21–26, 22–27, 23–28, 24–29, 25–30, 26–31, 27–32, 28–33, 29–34, 30–35, 31–36, 32–37, 33–38, 34–39, 35–40, 36–41, 37–42, 38–43, 39–44, 40–45, 41–46, 42–47, 43–48, 44–49, 45–50, 46–51, 47–52, 48–53, 49–54, 50–55, 51–56, 52–57, 53–58, 54–59, 55–60, 56–61, 57–62, 58–63, 59–64, 60–65, 61–66, 62–67, 63–68, 64–69, 65–70, 66–71, 67–72, 68–73, 69–74, 70–75, 71–76, 72–77, 73–78, 74–79, 75–80, 76–81, 77–82, 78–83, 79–84, 80–85, 81–86, 82–87, 83–88, 84–89, 85–90, 86–91, 87–92, 88–93, 89–94, 90–95, 91–96, 92–97, 93–98, 94–99, 95–100, 96–101, 97–102, 98–103, 99–104, 100–105, 101–106, 102–107, 103–108, 104–109, 105–110, 106–111, 107–112, 108–113, 109–114, 110–115, 111–116, 112–117, 113–118, 114–119, 115–120, 116–121, 117–122, 118–123, 119–124, 120–125, 121–126, 122–127, 123–128, 124–129, 125–130, 126–131, 127–132, 128–133, 129–134, 130–135, 131–136, 132–137, 133–138, 134–139, 135–140, 136–141, 137–142, 138–143, 139–144, 140–145, 141–146, 142–147, 143–148, 144–149, 145–150, 146–151, 147–152, 148–153, 149–154, 150–155, 151–156, 152–157, 153–158, 154–159, 155–160, 156–161, 157–162, 158–163, 159–164, 160–165, 161–166, 162–167, 163–168, 164–169, 165–170, 166–171, 167–172, 168–173, 169–174, 170–175, 171–176, 172–177, 173–178, 174–179, 175–180, 176–181, 177–182, 178–183, 179–184, 180–185, 181–186, 182–187, 183–188, 184–189, 185–190, 186–191, 187–192, 188–193, 189–194, 190–195, 191–196, 192–197, 193–198, 194–199, 195–200, 196–201, 197–202, 198–203, 199–204, 200–205, 201–206, 202–207, 203–208, 204–209, 205–210, 206–211, 207–212, 208–213, 209–214, 210–215, 211–216, 212–217, 213–218, 214–219, 215–220, 216–221, 217–222, 218–223, 219–224, 220–225, 221–226, 222–227, 223–228, 224–229, 225–230, 226–231, 227–232, 228–233, 229–234, 230–235, 231–236, 232–237, 233–238, 234–239, 235–240, 236–241, 237–242, 238–243, 239–244, 240–245, 241–246, 242–247, 243–248, 244–249, 245–250, 246–251, 247–252, and 248–253 for a polypeptide consisting of 253 consecutive amino acids. A 247 consecutive amino acid fragment could occupy positions selected from the group consisting of 1–247, 2–248, 3–249, 4–250, 5–251, 6–252 and 7–253 (SEQ ID NOs:2 or 4). Similarly, the positions occupied by all the other fragments of sizes between 6 amino acids and 253 or 228 amino acids in SEQ ID NOs: 2 or 4 and SEQ ID NO: 6, respectively, are included in the present invention and can also be immediately envisaged based on these two examples and therefore, are not individually listed solely for the purpose of not unnecessarily lengthening the specification. Furthermore, the positions occupied by fragments of 6 to next to the last amino acid consecutive amino acids in SEQ ID NOs: 2, 4 or 6 are included in the present invention and can also be immediately envisaged based on these two examples and therefore are not individually listed solely for the purpose of not unnecessarily lengthening the specification. In addition, the positions occupied by fragments of 6 consecutive amino acids to 1 amino acid less than any other full length Adipsin polypeptide can also be envisaged based on these two examples and therefore are not individually listed solely for the purpose of not unnecessarily lengthening the specification.

The Adipsin polypeptides of the present invention may alternatively be described by the formula "n to c" (inclusive); where "n" equals the N-terminal most amino acid position (as defined by the sequence listing) and "c" equals the C-terminal most amino acid position (as defined by the sequence listing) of the polypeptide; and further where "n" equals an integer between 1 and the number of amino acids of the full length polypeptide sequence of the present invention minus 5; and where "c" equals an integer between 6 and the number of amino acids of the full length polypeptide sequence; and where "n" is an integer smaller then "c" by at least 5. Therefore, for the sequences provided in SEQ ID NO: 2 or 4, "n" is any integer selected from the list consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247 and 248; and "c" is any integer selected from the group consisting of: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252 and 253. Every combination of "n" and "c" positions are included as specific embodiments of the invention. Moreover, the formula "n" to "c" may be modified as "'n1–n2" to "c1–c2"', wherein "n1–n2" and "c1–c2" represent positional ranges selected from any two integers above which represent amino acid positions of the sequence listing. Alternative formulas include "'n1–n2" to "c"' and "'n" to "c1–c2"'.

These specific embodiments, and other polypeptide and polynucleotide fragment embodiments described herein may be modified as being "at least", "equal to", "equal to or less than", "less than", "at least_but not greater than_" or "from_to_", a specified size or specified N-terminal and/or C-terminal positions. It is noted that all ranges used to describe any embodiment of the present invention are inclusive unless specifically set forth otherwise.

The present invention also provides for the exclusion of any individual fragment specified by N-terminal and C-terminal positions or of any fragment specified by size in amino acid residues as described above. In addition, any number of fragments specified by N-terminal and C-terminal positions or by size in amino acid residues as described above may be excluded as individual species. Further, any number of fragments specified by N-terminal and C-terminal positions or by size in amino acid residues as described above may make up a polypeptide fragment in any combination and may optionally include non-Adipsin polypeptide sequence as well.

In particularly preferred embodiments, the Adipsin polypeptides contain a "Proteolytic" domain.

Adipsin polypeptides of the invention include variants, fragments, analogs and derivatives of the Adipsin polypeptides described above, including modified Adipsin polypeptides.

Variants

It will be recognized by one of ordinary skill in the art that some amino acids of the Adipsin polypeptide sequences of the present invention can be varied without significant effect on the structure or function of the proteins; there will be critical amino acids in the sequence that determine activity. Thus, the invention further includes variants of Adipsin polypeptides that have metabolic-related activity as described above. Such variants include Adipsin polypeptide sequences with one or more amino acid deletions, insertions, inversions, repeats, and substitutions either from natural mutations or human manipulation selected according to general riles known in the art so as to have little effect on activity. Guidance concerning how to make phenotypically silent amino acid substitutions is provided below.

There are two main approaches for studying the tolerance of an amino acid sequence to change (see, Bowie, et al. (1990) Science, 247, 1306–10). The first method relies on the process of evolution, in which mutations are either accepted or rejected by natural selection. The second approach uses genetic engineering to introduce amino acid changes at specific positions of a cloned gene and selections or screens to identify sequences that maintain functionality.

These studies have revealed that proteins are surprisingly tolerant of amino acid substitutions and indicate which amino acid changes are likely to be permissive at a certain position of the protein. For example, most buried amino acid residues require nonpolar side chains, whereas few features of surface side chains are generally conserved. Other such phenotypically silent substitutions are described by Bowie et al. (supra) and the references cited therein.

In the case of an amino acid substitution in the amino acid sequence of a polypeptide according to the invention, one or several amino acids can be replaced by "equivalent" amino acids. The expression "equivalent" amino acid is used herein to designate any amino acid that may be substituted for one of the amino acids having similar properties, such that one skilled in the art of peptide chemistry would expect the secondary structure and hydropathic nature of the polypeptide to be substantially unchanged.

In particular embodiments, conservative substitutions of interest are shown in Table 1 under the heading of preferred substitutions. If such substitutions result in a change in biological activity, then more substantial changes, denominated exemplary substitutions in Table 4, or as further described below in reference to amino acid classes, are introduced and the products screened.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the Adipsin polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., Nucl. Acids Res., 13:4331 (1986); Zoller et al., Nucl. Acids Res., 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce the Adipsin variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main chain conformation of the variant [Cunningham and Wells, Science, 244: 1081–1085 (1989)]. Alanine is also typically preferred because it is the most common amino acid. Further, it is frequently found in both buried and exposed positions [Creighton, The Proteins, (W.H. Freeman & Co., N.Y.); Chothia, J. Mol. Biol., 150:1 (1976)]. If alanine substitution does not yield adequate amounts of variant, an isoteric amino acid can be used.

Amino acids in the Adipsin polypeptide sequences of the invention that are essential for function can also be identified by methods known in the art, such as site-directed mutagenesis or alanine-scanning mutagenesis (see, e.g., Cunningham, et al. (1989) Science 244(4908):1081–5). The latter procedure introduces single alanine mutations at every residue in the molecule. The resulting mutant molecules are then tested for metabolic-related activity using assays as described above. Of special interest are substitutions of charged amino acids with other charged or neutral amino acids that may produce proteins with highly desirable improved characteristics, such as less aggregation. Aggregation may not only reduce activity but also be problematic when preparing pharmaceutical or physiologically acceptable formulations, because aggregates can be immunogenic (see, e.g., Pinckard, et al., (1967) Clin. Exp. Immunol 2:331–340; Robbins, et al., (1987) Diabetes July;36(7): 838–41; and Cleland, et al., (1993) Crit Rev Ther Drug Carrier Syst. 10(4):307–77).

Thus, the fragment, derivative, analog, or homolog of the Adipsin polypeptides of the present invention may be, for example: (i) one in which one or more of the amino acid residues are substituted with a conserved or non-conserved amino acid residue (preferably a conserved amino acid residue) and such substituted amino acid residue may or may not be one encoded by the genetic code (i.e. may be a non-naturally occurring amino acid); or (ii) one in which one or more of the amino acid residues includes a substituent group; or (iii) one in which the Adipsin polypeptide is fused with another compound, such as a compound to increase the half-life of the fragment (for example, polyethylene glycol); or (iv) one in which the additional amino acids are fused to the above form of the fragment, such as an IgG Fc fusion region peptide or leader or secretory sequence or a sequence which is employed for purification of the above form of the fragment or a pro-protein sequence. Such fragments, derivatives and analogs are deemed to be within the scope of those skilled in the art from the teachings herein.

A further embodiment of the invention relates to a polypeptide which comprises the amino acid sequence of Adipsin polypeptide having an amino acid sequence which contains at least one conservative amino acid substitution, but not more than 50 conservative amino acid substitutions, not more than 40 conservative amino acid substitutions, not more than 30 conservative amino acid substitutions, and not more than 20 conservative amino acid substitutions. Also provided are polypeptides which comprise the amino acid sequence of a Adipsin fragment, having at least one, but not more than 10, 9, 8, 7, 6, 5, 4, 3, 2 or 1 conservative amino acid substitutions.

Another specific embodiment of a modified Adipsin polypeptide of the invention is a polypeptide that is resistant to proteolysis, for example a Adipsin polypeptide mi which a —CONH-peptide bond is modified and replaced by one or more of the following: a (CH2NH) reduced bond; a (NHCO) retro inverso bond; a (CH2-O) methylene-oxy bond; a (CH2-S) thiomenthylene bond; a (CH2CH2) carba bond; a (CO—CH2) cetomethylene bond; a (CHOH—CH2) hydroxyethylene bond); a (N—N) bound; a E-alcene bond; or a —CH=CH— bond. Thus, the invention also encompasses a Adipsin polypeptide or a variant thereof in which at least one peptide bond has been modified as described above.

In addition, amino acids have chirality within the body of either L or D. In some embodiments it is preferable to alter the chirality of the amino acids in the Adipsin polypeptides of the invention in order to extend half-life within the body. Thus, in some embodiments, one or more of the amino acids are preferably in the L configuration. In other embodiments, one or more of the amino acids are preferably in the D configuration.

Percent Identity

The polypeptides of the present invention also include polypeptides having an amino acid sequence at least 50% identical, at least 60% identical, or 70%, 80%, 85%, 90%, 91%, 92%, 93%, 94%, 95%, 96%, 97%, 98% or 99% identical to a Adipsin polypeptide as described above. By a polypeptide having an amino acid sequence at least, for example, 95% "identical" to a Adipsin polypeptide amino acid sequence is meant that the amino acid sequence is identical to the Adipsin polypeptide sequence except that it may include up to five amino acid alterations per each 100 amino acids of the Adipsin polypeptide amino acid sequence. The reference sequence is the Adipsin polypeptide with a sequence corresponding to the sequences provided in SEQ ID NOs: 2, 4 or 6. Thus, to obtain a polypeptide having an amino acid sequence at least 95% identical to a Adipsin polypeptide amino acid sequence, up to 5% (5 of 100) of the amino acid residues in the sequence may be inserted, deleted, or substituted with another amino acid compared with the Adipsin polypeptide sequence. These alterations may occur at the amino or carboxy termini or anywhere between those terminal positions, interspersed either individually among residues in the sequence or in one or more contiguous groups within the sequence.

As a practical matter, whether any particular polypeptide is a percentage identical to a Adipsin polypeptide can be determined conventionally using known computer programs. Such algorithms and programs include, but are by no means limited to, TBLASTN, BLASTP, FASTA, TFASTA, and CLUSTALW (Pearson and Lipman, (1988) Proc Natl Acad Sci USA April;85(8):2444–8; Altschul et al., (1990) J. Mol. Biol. 215(3):403–410; Thompson et al., (1994) Nucleic Acids Res. 22(2):4673–4680; Higgins et al., (1996) Meth. Enzymol. 266:383–402; Altschul et al., (1997) Nuc. Acids Res. 25:3389–3402; Altschul et al., (1993) Nature Genetics 3:266–272). In a particularly preferred embodiment, protein and nucleic acid sequence homologies are evaluated using the Basic Local Alignment Search Tool ("BLAST"), which is well known in the art (See, e.g., Karlin and Altschul (1990) Proc Natl Acad Sci USA March;87(6):2264–8; Altschul et al., 1990, 1993, 1997, all supra). In particular, five specific BLAST programs are used to perform the following tasks:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (see, Gonnet et al., (1992) Science June 5;256(5062):1443–5; Henikoff and Henikoff (1993) Proteins September;17(1):49–61). Less preferably, the PAM or PAM250 matrices may also be used (See, e.g., Schwartz and Dayhoff, eds, (1978) Matrices for Detecting Distance Relationships: Atlas of Protein Sequence and Structure, Washington: National Biomedical Research Foundation). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (See, e.g., Karlin and Altschul, (1990) Proc Natl Acad Sci USA March;87(6): 2264–8). The BLAST programs may be used with the default parameters or with modified parameters provided by the user. Preferably, the parameters are default parameters.

A preferred method for determining the best overall match between a query sequence (a sequence of the present invention) and a subject sequence, also referred to as a global sequence alignment, can be determined using the FASTDB computer program based on the algorithm of Brutlag et al. (1990) Comp. App. Biosci. 6:237–245. In a sequence alignment the query and subject sequences are both amino acid sequences. The result of said global sequence alignment is in percent identity. Preferred parameters used in a FASTDB amino acid alignment are: Matrix= PAM 0, k-tuple=2, Mismatch Penalty=1, Joining Penalty= 20, Randomization Group=25 Length=0, Cutoff Score=1, Window Size=sequence length, Gap Penalty=5, Gap Size Penalty=0.05, Window Size=247 or the length of the subject amino acid sequence, whichever is shorter.

If the subject sequence is shorter than the query sequence due to N- or C-terminal deletions, not because of internal deletions, the results, in percent identity, must be manually corrected because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, that are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query amino acid residues outside the farthest N- and C-terminal residues of the subject sequence.

For example, a 90 amino acid residue subject sequence is aligned with a 100-residue query sequence to determine percent identity. The deletion occurs at the N-terminus of the subject sequence and therefore, the FASTDB alignment does not match/align with the first residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%.

In another example, a 90-residue subject sequence is compared with a 100-residue query sequence. This time the deletions are internal so there are no residues at the N- or C-termini of the subject sequence, which are not matched/ aligned with the query. In this case, the percent identity calculated by FASTDB is not manually corrected. Once again, only residue positions outside the N- and C-terminal ends of the subject sequence, as displayed in the FASTDB alignment, which are not matched/aligned with the query sequence are manually corrected. No other manual corrections are made for the purposes of the present invention.

Production

Note, throughout the disclosure, wherever Adipsin polypeptides are discussed, Adipsin fragments, variants and derivatives are specifically intended to be included as a preferred subset of Adipsin polypeptides.

Adipsin polypeptides are preferably isolated from human or mammalian tissue samples or expressed from human or mammalian genes in human or mammalian cells. The Adipsin polypeptides of the invention can be made using routine expression methods known in the art. The polynucleotide encoding the desired polypeptide is ligated into an expression vector suitable for any convenient host. Both eukaryotic and prokaryotic host systems are used in forming recombinant polypeptides. The polypeptide is then isolated from lysed cells or from the culture medium and purified to the extent needed for its intended use. Purification is by any technique known in the art, for example, differential extraction, salt fractionation, chromatography, centrifugation, and the like. See, for example, Methods in Enzymology for a variety of methods for purifying proteins.

In a alternative embodiment, the polypeptides of the invention are isolated from milk. The polypeptides can be purified as full length Adipsin polypeptides, which can then be cleaved, if appropriate, in vitro to generate a Adipsin fragment, or, alternatively, Adipsin fragments themselves can be purified from the milk. Any of a large number of methods can be used to purify the present polypeptides from milk, including those taught in Protein Purification Applications, A Practical Approach (New Edition), Edited by Simon Roe, AEA Technology Products and Systems, Biosciences, Harwell; Clark (1998) J Mammary Gland Biol Neoplasia 3:337–50; Wilkins and Velander (1992) 49:333–8; U.S. Pat. Nos. 6,140,552; 6,025,540; Hennighausen, Protein Expression and Purification, vol. 1, pp. 3–8 (1990); Harris et al. (1997) Bioseparation 7:31–7; Degener et al. (1998) J. Chromatog. 799:125–37; Wilkins (1993) J. Cell. Biochem. Suppl. 0 (17 part A):39; the entire disclosures of each of which are herein incorporated by reference. In a typical embodiment, milk is centrifuged, e.g. at a relatively low speed, to separate the lipid fraction, and the aqueous supernatant is then centrifuged at a higher speed to separate the casein in the milk from the remaining, "whey" fraction. Often, biomedical proteins are found in this whey fraction, and can be isolated from this fraction using standard chromatographic or other procedures commonly used for protein purification, e.g. as described elsewhere in the present application. In one preferred embodiment, Adipsin polypeptides are purified using antibodies specific to Adipsin polypeptides, e.g. using affinity chromatography. In addition, methods can be used to isolate particular Adipsin fragments, e.g. electrophoretic or other methods for isolating proteins of a particular size. The Adipsin polypeptides isolating using these methods can be naturally occurring, as Adipsin polypeptides have been discovered to be naturally present in the milk of mammals, or can be the result of the recombinant production of the protein in the mammary glands of a non-human mammal, as described infra. In one such embodiment, the Adipsin is produced as a fusion protein with a heterologous, antigenic polypeptide sequence, which antigenic sequence can be used to purify the protein, e.g., using standard immuno-affinity methodology.

In addition, shorter protein fragments may be produced by chemical synthesis. Alternatively, the proteins of the invention are extracted from cells or tissues of humans or non-human animals. Methods for purifying proteins are known in the art, and include the use of detergents or chaotropic agents to disrupt particles followed by differential extraction and separation of the polypeptides by ion exchange chromatography, affinity chromatography, sedimentation according to density, and gel electrophoresis.

Any Adipsin cDNA, including those in SEQ ID NO: 2, can be used to express Adipsin polypeptides. The nucleic acid encoding the Adipsin to be expressed is operably linked to a promoter in an expression vector using conventional cloning technology. The Adipsin cDNA insert in the expression vector may comprise the coding sequence for: the full length Adipsin polypeptide (to be later modified); from 6 amino acids to 6 amino acids any integer less than the full-length Adipsin polypeptide; a Adipsin fragment; or variants and % similar polypeptides.

The expression vector is any of the mammalian, yeast, insect or bacterial expression systems known in the art, some of which are described herein. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence can be optimized for the particular expression organism into which the expression vector is introduced, as explained by Hatfield, et al., U.S. Pat. No. 5,082,767, the disclosures of which are incorporated by reference herein in their entirety.

If the nucleic acid encoding any one of the Adipsin polypeptides lacks a methionine to serve as the initiation site, an initiating methionine can be introduced next to the first codon of the nucleic acid using conventional techniques. Similarly, if the insert from the Adipsin polypeptide cDNA lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene.

The nucleic acid encoding a Adipsin can be obtained by PCR from a vector containing the Adipsin nucleotide sequence using oligonucleotide primers complementary to the desired Adipsin cDNA and containing restriction endonuclease sequences for Pst I incorporated into the 5' primer and BglII at the 5' end of the corresponding cDNA 3' primer, taking care to ensure that the sequence encoding the Adipsin is positioned properly with respect to the poly A signal. The purified polynucleotide obtained from the resulting PCR reaction is digested with PstI blunt ended with an exonuclease, digested with Bgl II, purified and ligated to pXT1, now containing a poly A signal and digested with BglII.

Transfection of a Adipsin expressing vector into mouse NIH 3T3 cells is one embodiment of introducing polynucleotides into host cells. Introduction of a polynucleotide encoding a polypeptide into a host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al. ((1986) Methods in Molecular Biology, Elsevier Science Publishing Co., Inc., Amsterdam). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells.

Depending upon the host employed in a recombinant production procedure, the polypeptides of the present invention may be glycosylated or may be non-glycosylated. Preferably the polypeptides of the invention are non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., (1989) Proc Natl Acad Sci USA November;86(22):8932–5; Koller et al., (1989) Proc Natl Acad Sci USA November;86(22):8927–31; and Zijlstra et al. (1989) Nature November 23;342(6248): 435–8; the disclosures of each of which are incorporated by reference in their entireties).

Modifications

In addition, polypeptides of the invention can be chemically synthesized using techniques known in the art (See, e.g., Creighton, 1983 Proteins. New York, N.Y.: W.H. Freeman and Company; and Hunkapiller et al., (1984) Nature July 12–18;310(5973):105–11). For example, a relative short fragment of the invention can be synthesized by use of a peptide synthesizer. Furthermore, if desired, nonclassical amino acids or chemical amino acid analogs can be introduced as a substitution or addition into the fragment sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoroamino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methlonine residue as a result of procaryotic host cell expression. The polypeptides may also be modified with a detectable label, such as an enzymatic, fluorescent, isotopic or affinity label to allow for detection and isolation of the polypeptide.

Also provided by the invention are chemically modified derivatives of the polypeptides of the invention that may provide additional advantages such as increased solubility, stability and circulating time of the polypeptide, or decreased immunogenicity. See U.S. Pat. No. 4,179,337. The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigerticity and other known effects of the polyethylene glycol to a therapeutic protein or analog).

The polyethylene glycol molecules (or other chemical moieties) should be attached to the polypeptide with consideration of effects on functional or antigenic domains of the polypeptide. There are a number of attachment methods available to those skilled in the art, e.g., EP 0 401 384, herein incorporated by reference (coupling PEG to G-CSF), see also Malik et al. (1992) Exp Hematol. September;20(8) :1028–35, reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus may be accomplished by reductive alkylation, which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

Multimers

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, pharmaceutical or physiologically acceptable compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the Adipsin polypeptides of the invention (including polypeptide fragments, variants, splice variants, and fusion proteins corresponding to these polypeptide fragments as described herein). These homomers may contain polypeptide fragments having identical or different amino acid sequences. In a specific embodiment, a homomer of the invention is a multimer containing only polypeptide fragments having an identical amino acid sequence. In another specific embodiment, a homomer of the invention is a multimer containing polypeptide fragments having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., corresponding to different proteins or polypeptides thereof) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences, which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, oseteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins, and have since been found in a variety of different proteins (Landschulz et al., (1988) Genes Dev. July;2(7):786–800). Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. FEBS Letters (1994) May 16;344(2–3): 191–5, and in U.S. patent application Ser. No. 08/446,922, hereby incorporated by reference. Other peptides derived from naturally occurring trimeric proteins may be employed in preparing trimeric polypeptides of the invention. In another example, proteins of the invention are associated by interactions between FLAG & polypeptide sequence contained in fusion proteins of the invention contaning FLAG polypeptide sequence. In a further embodiment, proteins of the invention are associated by interactions between heterologous polypeptide sequence contained in FLAG fusion proteins of the invention and anti FLAG antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C-terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, at least 30 techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained In multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (See, e.g., U.S. Pat. No. 5,478,925, which is herein incorporated by reference in its entirety).

II. Adipsin Polynucleotides of the Invention

Preferred polynucleotides are those that encode Adipsin polypeptides of the invention. The recombinant polynucleotides encoding Adipsin polypeptides can be used in a variety of ways, including, but not limited to, expressing the polypeptides in recombinant cells for use in screening assays for antagonists and agonists of its activity as well as to facilitate its purification for use in a variety of ways including, but not limited to screening assays for agonists and antagonists of its activity, diagnostic screens, and raising antibodies, as well as treatment and/or prevention of metabolic-related diseases and disorders and/or to reduce body mass.

The invention relates to the polynucleotides encoding Adipsin polypeptides and variant polypeptides thereof as described herein. These polynucleotides may be purified, isolated, and/or recombinant. In all cases, the desired Adipsin polynucleotides of the invention are those that encode Adipsin polypeptides of the invention having metabolic-related activity as described and discussed herein.

Fragments

A polynucleotide fragment is a polynucleotide having a sequence that entirely is the same as part, but not all, of the full length Adipsin polypeptide or a specified Adipsin polypeptide nucleotide sequence. Such fragments may be "free-standing", i.e. not part of or fused to other polynucleotides, or they may be comprised within another non-Adipsin (heterologous) polynucleotide of which they form a part or region. However, several Adipsin polynucleotide fragments may be comprised within a single polynucleotide.

The Adipsin polynucleotides of the invention comprise from 18 consecutive bases to 18 consecutive bases less than the full length polynucleotide sequences encoding the intact Adipsin polypeptides, for example the full length Adipsin polypeptide polynucleotide sequences in SEQ ID NOs: 1, 3 or 5. In one aspect of this embodiment, the polynucleotide comprises at least 18, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 740, 770, 800, 850, 900, 950, 1000, 1100, 1200, 1300, 1400, 1500, 1600, 1700, 1800, 1900, 2000, 2100 or 2200 consecutive nucleotides of a polynucleotide of the present invention.

In addition to the above preferred nucleic acid sizes, further preferred nucleic acids comprise at least 18 nucleotides, wherein "at least 18" is defined as any integer between 18 and the integer representing 18 nucleotides less than the 3' most nucleotide position of the intact Adipsin polypeptides cDNA as set forth in SEQ ID NOs: 1, 3 or 5 or elsewhere herein.

Further included as preferred polynucleotides of the present invention are nucleic acid fragments at least 18 nucleotides in length, as described above, that are further specified in terms of their 5' and 3' position. The 5' and 3' positions are represented by the position numbers set forth in the sequence listing below. For allelic and degenerate and other variants, position 1 is defined as the 5' most nucleotide of the ORF, i.e., the nucleotide "A" of the start codon (ATG) with the remaining nucleotides numbered consecutively. Therefore, every combination of a 5' and 3' nucleotide position that a polynucleotide fragment, at least 18 contiguous nucleotides in length, could occupy on an intact Adipsin polypeptide encoding a polynucleotide of the present invention is included in the invention as an individual species. The polynucleotide fragments specified by 5' and 3' positions can be immediately envisaged and are therefore not individually listed solely for the purpose of not unnecessarily lengthening the specification.

It is noted that the above species of polynucleotide fragments of the present invention may alternatively be described by the formula "x to y"; where "x" equals the 5' most nucleotide position and "y" equals the 3' most nucleotide position of the polynucleotide; and further where "x" equals an integer between 1 and the number of nucleotides of the polynucleotide sequence of the present invention minus 18, and where "y" equals an integer between 19 and the number of nucleotides of the polynucleotide sequence of the present invention minus 18 nucleotides; and where "x" is an integer less than "y" by at least 18.

The present invention also provides for the exclusion of any species of polynucleotide fragments of the present invention specified by 5' and 3' positions or polynucleotides specified by size in nucleotides as described above. Any number of fragments specified by 5' and 3' positions or by size in nucleotides, as described above, may be excluded.

The Adipsin polynucleotide fragments of the invention comprise from 18 consecutive bases to the full length polynucleotide sequence encoding the Adipsin fragments described in Section II of the Preferred Embodiments of the Invention. In one aspect of this embodiment, the polynucleotide comprises at least 18, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 740, 770, 800, 850, 900, 950, 1000, 1100, 1200, 1300, 1400, 1500, 1600, 1700, 1800, 1900, 2000, 2100 or 2200 consecutive nucleotides of a polynucleotide of the present invention.

In addition to the above preferred nucleic acid sizes, further preferred nucleic acids comprise at least 18 nucleotides, wherein "at least 18" is defined as any integer between 18 and the integer corresponding to the 3' most nucleotide position of a Adipsin fragment cDNA herein.

Further included as preferred polynucleotides of the present invention are nucleic acid fragments at least 18 nucleotides in length, as described above, that are further specified in terms of their 5' and 3' position. The 5' and 3' positions are represented by the position numbers set forth in the sequence listing below. For allelic and degenerate and other variants, position 1 is defined as the 5' most nucleotide of the open reading frame (ORF), i.e., the nucleotide "A" of the start codon (ATG) with the remaining nucleotides numbered consecutively. Therefore, every combination of a 5' and 3' nucleotide position that a polynucleotide fragment invention, at least 18 contiguous nucleotides in length, could occupy on a Adipsin fragment polynucleotide of the present invention is included in the invention as an individual species. The polynucleotide fragments specified by 5' and 3' positions can be immediately envisaged and are therefore not individually listed solely for the purpose of not unnecessarily lengthening the specification.

It is noted that the above species of polynucleotide fragments of the present invention may alternatively be described by the formula "x to y"; where "x" equals the 5' most nucleotide position and "y" equals the 3' most nucleotide position of the polynucleotide; and further where "x" equals an integer between 1 and the number of nucleotides of the Adipsin polynucleotide sequences of the present invention minus 18, and where "y" equals an integer between 9 and the number of nucleotides of the Adipsin polynucleotide sequences of the present invention; and where "x" is an integer smaller than "y" by at least 18. Every combination of "x" and "y" positions are included as specific embodiments of the invention. Moreover, the formula "x" to "y" may be modified as "'x1–x2" to "y1–y2"', wherein "x1–x2" and "y1–y2" represent positional ranges selected from any two nucleotide positions of the sequence listing. Alternative formulas include "'x1–x2" to "y"' and "'x" to "y1–y2"'.

These specific embodiments, and other polynucleotide fragment embodiments described herein may be modified as being "at least", "equal to", "equal to or less than", "less than", "at least_but not greater than_" or "from_to_". a specified size or specified 5' and/or 3' positions.

The present invention also provides for the exclusion of any species of polynucleotide fragments of the present invention specified by 5' and 3' positions or polynucleotides specified by size in nucleotides as described above. Any number of fragments specified by 5' and 3' positions or by size in nucleotides, as described above, may be excluded.

Variants

In other preferred embodiments, variants of Adipsin polynucleotides encoding Adipsin polypeptides are envisioned. Variants of polynucleotides, as the term is used herein, are polynucleotides whose sequence differs from a reference polynucleotide. A variant of a polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms. Generally, differences are limited so that the nucleotide sequences of the reference and the variant are closely similar overall and, in many regions, identical.

Polynucleotide variants that comprise a sequence substantially different from those described above but that, due to the degeneracy of the genetic code, still encode Adipsin polypeptides of the present invention are also specifically envisioned. It would also be routine for one skilled in the art to generate the degenerate variants described above, for instance, to optimize codon expression for a particular host (e.g., change codons in the human mRNA to those preferred by other mammalian or bacterial host cells).

As stated above, variant polynucleotides may occur naturally, such as a natural allelic variant, or by recombinant methods. By an "allelic variant" is intended one of several alternate forms of a gene occupying a given locus on a chromosome of an organism (See, e.g., B. Lewin, (1990) Genes IV, Oxford University Press, New York). Non-naturally occurring variants may be produced using art-known mutagenesis techniques. Such nucleic acid variants include those produced by nucleotide substitutions, deletions, or additions. The substitutions, deletions, or additions may involve one or more nucleotides. Alterations in the coding regions may produce conservative or non-conservative amino acid substitutions, deletions or additions. Especially preferred among these are silent substitutions, additions and deletions, which do not alter the properties and activities of Adipsin polypeptides of the invention. Also preferred in this regard are conservative substitutions.

Nucleotide changes present in a variant polynucleotide are preferably silent, which means that they do not alter the amino acids encoded by the polynucleotide. However, nucleotide changes may also result in amino acid substitutions, additions, deletions, fusions and truncations in the polypeptide encoded by the reference sequence.

In cases where the nucleotide substitutions result in one or more amino acid changes, preferred Adipsin polypeptides include those that retain one or more metabolic-related activity as described in Section I of the Preferred Embodiments of the Invention.

By "retain the same activities" is meant that the activity measured using the polypeptide encoded by the variant Adipsin polynucleotide in assays is at least 75%, 80%, 85%, 90%, 95%, 96%, 97%, 98%, 99%, or 100%, and not more than 101%, 102%, 103%, 104%, 105%, 110%, 115%, 120% or 125% of the activity measured using a Adipsin polypeptide described in the Examples Section herein.

By the activity being "increased" is meant that the activity measured using the polypeptide encoded by the variant Adipsin polynucleotide in assays is at least 125%, 130%, 135%, 140%, 145%, 150%, 155%, 160%, 170%, 180%, 190%, 200%, 225%, 250%, 275%, 300%, 325%, 350%, 375%, 400%, 450%, or 500% of the activity measured using a Adipsin polypeptide described in the Examples Section herein.

By the activity being "decreased" is meant that the activity measured using the polypeptide encoded by the variant Adipsin polynucleotide in assays is decreased by at least 25%, 30%, 35%, 40%, 45%, 50%, 75%, 80%, 90% or 95% of the activity measured using a Adipsin polypeptide described in the Examples Section herein Percent Identity The present invention is further directed to nucleic acid molecules having sequences at least 50%, 60%, 70%, 80%, 90%, 95%, 96%, 97%, 98% or 99% identical to the polynucleotide sequences of SEQ ID NO: 1 or fragments thereof that encode a polypeptide having metabolic-related activity as described in Section I of the Preferred Embodiments of the Invention. Of course, due to the degeneracy of the genetic code, one of ordinary skill in the art will immediately recognize that a large number of the nucleic acid molecules at least 50%, 60%, 70%, 80%, 90%, 95%, 96%, 97%, 98%, or 99% identical to the nucleic acid sequences shown in SEQ ID NO: 1 or fragments thereof will encode a polypeptide having biological activity. In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having biological activity. This is because the skilled artisan is fully aware of amino acid substitutions that are either less likely or not likely to significantly affect protein function (e.g., replacing one aliphatic amino acid with a second aliphatic amino acid), as further described previously in Section I of the Preferred Embodiments of the Invention.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the Adipsin polypeptide. In other words, to obtain a polynucleotide having a nucleotide sequence at least 95% identical to a reference nucleotide sequence, up to 5% of the nucleotides in the reference sequence may be deleted, inserted, or substituted with another nucleotide. The query sequence may be an entire sequence or any fragment specified as described herein.

The methods of determining and defining whether any particular nucleic acid molecule or polypeptide is at least 50%, 60%, 70%, 80%, 90%, 95%, 96%, 97%, 98% or 99% identical to a nucleotide sequence of the present invention can be done by using known computer programs. A preferred method for determining the best overall match between a query sequence (a sequence of the present invention) and a subject sequence, also referred to as a global sequence alignment, can be determined using the FASTDB computer program based on the algorithm of Brutlag et al., ((1990) Comput Appl Biosci. July;6(3):237–45). In a sequence alignment the query and subject sequences are both DNA sequences. An RNA sequence can be compared by first converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only nucleotides outside the 5' and 3' nucleotides of the subject sequence, as displayed by the FASTDB alignment, which are not matched/aligned with the query sequence, are calculated for the purposes of manually adjusting the percent identity score.

For example, a 90-nucleotide subject sequence is aligned to a 100-nucleotide query sequence to determine percent identity. The deletions occur at the 5' end of the subject sequence and therefore, the FASTDB alignment does not show a matched/alignment of the first 10 nucleotides at 5' end. The 10 unpaired nucleotides represent 10% of the sequence (number of nucleotides at the 5' and 3' ends not matched/total number of nucleotides in the query sequence) so 10% is subtracted from the percent identity score calculated by the FASTDB program. If the remaining 90 nucleotides were perfectly matched the final percent identity would be 90%.

In another example, a 90 nucleotide subject sequence is compared with a 100 nucleotide query sequence. This time the deletions are internal deletions so that there are no nucleotides on the 5' or 3' of the subject sequence which are not matched/aligned with the query. In this case the percent identity calculated by FASTDB is not manually corrected. Once again, only nucleotides 5' and 3' of the subject sequence which are not matched/aligned with the query sequence are manually corrected for. No other manual corrections are made for the purposes of the present invention.

Fusions

Further included in the present invention are polynucleotides encoding the polypeptides of the present invention that are fused in frame to the coding sequences for additional heterologous amino acid sequences. Also included in the present invention are nucleic acids encoding polypeptides of the present invention together with additional, non-coding sequences, including for example, but not limited to non-coding 5' and 3' sequences, vector sequence, sequences used for purification, probing, or priming. For example, heterologous sequences include transcribed, non-translated sequences that may play a role in transcription, and mRNA processing, for example, ribosome binding and stability of mRNA. The heterologous sequences may alternatively comprise additional coding sequences that provide additional functionalities. Thus, a nucleotide sequence encoding a polypeptide may be fused to a tag sequence, such as a sequence encoding a peptide that facilitates purification of the fused polypeptide. In certain preferred embodiments of this aspect of the invention, the tag amino acid sequence is a hexa-histidine peptide, such as the tag provided in a pQE vector (QIAGEN, Inc., 9259 Eton Avenue, Chatsworth, Calif., 91311), among others, many of which are commercially available. For instance, hexa-histidine provides for convenient purification of the fusion protein (See, Gentz et al., (1989) Proc Natl Acad Sci USA February;86(3):821–4). The "HA" tag is another peptide useful for purification which corresponds to an epitope derived from the influenza hemagglutinin protein (See, Wilson et al., (1984) Cell 37(3): 767–78). As discussed above, other such fusion proteins include Adipsin cDNA fused to Fc at the N- or C-terminus.

In a preferred embodiment of the present invention, Adipsin polypeptides are used in methods of proteolytically cleaving Apm1 or ACRP30 polypeptides, said methods comprising the step of contacting said Adipsin polypeptide with an Apm1 or ACRP30 polypeptide under conditions permitting the proteolytic cleavage of Apm1 or ACRP30. Preferably, the Adipsin polypeptide is recombinant Adipsin or an Adipsin polypeptide isolated in a form that does not comprise cells or tissues or is purified to at least 50%, 75%, 80%, 90%, 95%, 97%, 98%, 99% pure in relation to other polypeptides, polynucleotides, lipids, or all other molecules which do not comprise the carrier.

Recombinant Vectors of the Invention

The term "vector" is used herein to designate either a circular or a linear DNA or RNA molecule, that is either double-stranded or single-stranded, and that comprises at least one polynucleotide of interest that is sought to be transferred in a cell host or in a unicellular or multicellular host organism.

The present invention relates to recombinant vectors comprising any one of the polynucleotides described herein.

The present invention encompasses a family of recombinant vectors that comprise polynucleotides encoding Adipsin polypeptides of the invention.

In a first preferred embodiment, a recombinant vector of the invention is used to amplify the inserted polynucleotide in a suitable cell host, this polynucleotide being amplified every time that the recombinant vector replicates. The inserted polynucleotide can be one that encodes Adipsin polypeptides of the invention.

A second preferred embodiment of the recombinant vectors according to the invention consists of expression vectors comprising polynucleotides encoding Adipsin polypeptides of the invention. Within certain embodiments, expression vectors are employed to express a Adipsin polypeptide of the invention, preferably a modified Adipsin described in the present invention, which can be then purified and, for example, be used as a treatment for metabolic-related diseases, or simply to reduce body mass of individuals.

Expression requires that appropriate signals are provided in the vectors, said signals including various regulatory elements, such as enhancers/promoters from both viral and mammalian sources, that drive expression of the genes of interest in host cells. Dominant drug selection markers for establishing permanent, stable, cell clones expressing the products are generally included in the expression vectors of the invention, as they are elements that link expression of the drug selection markers to expression of the polypeptide.

More particularly, the present invention relates to expression vectors which include nucleic acids encoding a Adipsin polypeptide of the invention, or a modified Adipsin as described herein, or variants or fragments thereof, under the control of a regulatory sequence selected among Adipsin polypeptides, or alternatively under the control of an exogenous regulatory sequence.

Consequently, preferred expression vectors of the invention are selected from the group consisting of: (a) a Adipsin regulatory sequence and driving the expression of a coding polynucleotide operably linked thereto; and (b) a Adipsin coding sequence of the invention, operably linked to regulatory sequences allowing its expression in a suitable cell host and/or host organism.

Some of the elements which can be found in the vectors of the present invention are described m further detail in the following sections.

1) General Features of the Expression Vectors of the Invention:

A recombinant vector according to the invention comprises, but is not limited to, a YAC (Yeast Artificial Chromosome), a BAC (Bacterial Artificial Chromosome), a phage, a phagemid, a cosmid, a plasmid, or even a linear DNA molecule which may consist of a chromosomal, non-chromosomal, semi-synthetic or synthetic DNA. Such a recombinant vector can comprise a transcriptional unit comprising an assembly of:

(1) a genetic element or elements having a regulatory role in gene expression, for example promoters or enhancers. Enhancers are cis-acting elements of DNA, usually from about 10 to 300 bp in length that act on the promoter to increase the transcription;

(2) a structural or coding sequence which is transcribed into mRNA and eventually translated into a polypeptide, said structural or coding sequence being operably linked to the regulatory elements described in (1); and (3) appropriate transcription initiation and termination sequences. Structural units intended for use in yeast or eukaryotic expression systems preferably include a leader sequence enabling extracellular secretion of translated protein by a host cell. Alternatively, when a recombinant protein is expressed without a leader or transport sequence, it may include a N-terminal residue. This residue may or may not be subsequently cleaved from the expressed recombinant protein to provide a final product.

Generally, recombinant expression vectors will include origins of replication, selectable markers permitting transformation of the host cell, and a promoter derived from a highly expressed gene to direct transcription of a downstream structural sequence. The heterologous structural sequence is assembled in appropriate phase with translation initiation and termination sequences, and preferably a leader sequence capable of directing secretion of the translated protein into the periplasmic space or the extracellular medium. In a specific embodiment wherein the vector is adapted for transfecting and expressing desired sequences in mammalian host cells, preferred vectors will comprise an origin of replication in the desired host, a suitable promoter and enhancer, and also any necessary ribosome binding sites, polyadenylation sites, splice donor and acceptor sites, transcriptional termination sequences, and 5'-flanking non-transcribed sequences. DNA sequences derived from the SV40 viral genome, for example SV40 origin, early promoter, enhancer, splice and polyadenylation sites may be used to provide the required non-transcribed genetic elements.

2) Regulatory Elements

Promoters

The suitable promoter regions used in the expression vectors of the present invention are chosen taking into account the cell host in which the heterologous gene is expressed. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell, such as, for example, a human or a viral promoter.

A suitable promoter may be heterologous with respect to the nucleic acid for which it controls the expression or alternatively can be endogenous to the native polynucleotide containing the coding sequence to be expressed. Additionally, the promoter is generally heterologous with respect to the recombinant vector sequences within which the construct promoter/coding sequence has been inserted.

Promoter regions can be selected from any desired gene using, for example, CAT (chloramphenicol transferase) vectors and more preferably pKK232-8 and pCM7 vectors.

Preferred bacterial promoters are the LacI, LacZ, the T3 or T7 bacteriophage RNA polymerase promoters, the gpt, lambda PR, PL and trp promoters (EP 0036776), the polyhedrin promoter, or the p10 protein promoter from baculovirus (Kit Novagen) (Smith et al., (1983) Mol Cell Biol December;3(12):2156–65; O'Reilly et al., 1992), the lambda PR promoter or also the trc promoter.

Eukaryotic promoters include CMV immediate early, HSV thymidine kinase, early and late SV40, LTRs from retrovirus, and mouse metallothionein-L. In addition, promoters specific for a particular cell type may be chosen, such as those facilitating expression in adipose tissue, muscle tissue, or liver. Selection of a convenient vector and promoter is well within the level of ordinary skill in the art.

The choice of a promoter is well within the ability of a person skilled in the field of genetic engineering. For example, one may refer to Sambrook et al. (1989) Molecular Cloning: A Laboratory Manual, Cold Spring Harbor Laboratory Press, NY, Vol. 1, 2, 3 (1989), or also to the procedures described by Fuller et al. (1996) Immunology in Current Protocols in Molecular Biology.

Other Regulatory Elements

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

Vectors containing the appropriate DNA sequence as described above can be utilized to transform an appropriate host to allow the expression of the desired polypeptide or polynucleotide.

3) Selectable Markers

Such markers would confer an identifiable change to the cell permitting easy identification of cells containing the expression construct. The selectable marker genes for selection of transformed host cells are preferably dihydrofolate reductase or neomycin resistance for eukaryotic cell culture, TRP1 for *S. cerevisiae* or tetracycline, rifampicin or ampicillin resistance in *E. coli*, or levan saccharase for mycobacteria, this latter marker being a negative selection marker.

4) Preferred Vectors

Bacterial Vectors

As a representative but non-limiting example, useful expression vectors for bacterial use can comprise a selectable marker and a bacterial origin of replication derived from commercially available plasmids comprising genetic elements of pBR322 (ATCC 37017). Such commercial vectors include, for example, pKK223-3 (Pharmacia, Uppsala, Sweden), and pGEM1 (Promega Biotec, Madison, Wis., USA).

Large numbers of other suitable vectors are known to those of skill in the art, and are commercially available, such as the following bacterial vectors: pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pRIT5 (Pharmacia); pWLNEO, pSV2CAT, pOG44, pXT1, pSG (Stratagene); pSVK3, pBPV, pMSG, pSVL (Pharmacia); pQE-30 (QIAexpress).

Baculovirus Vectors

A suitable vector for the expression of polypeptides of the invention is a baculovirus vector that can be propagated in insect cells and in insect cell lines. A specific suitable host vector system is the pVL1392/1393 baculovirus transfer vector (Pharmingen) that is used to transfect the SF9 cell line (ATCC N°CRL 1711) which is derived from *Spodoptera frugiperda*.

Other suitable vectors for the expression of an Apm1 globular head polypeptide in a baculovirus expression system include those described by Chai et al. (1993; Biotechnol Appl Biochem. December;18 (Pt 3):259–73); Vlasak et al. (1983; Eur J Biochem September 1;135(1):123–6); and Lenhard et al. (1996; Gene March 9;169(2):187–90).

Viral Vectors

In one specific embodiment, the vector is derived from an adenovirus. Preferred adenovirus vectors according to the invention are those described by Feldman and Steg (1996; Semin Interv Cardiol September;1(3):203–8) or Ohno et al. (1994; Science August 5;265(5173):781–4). Another preferred recombinant adenovirus according to this specific embodiment of the present invention is the human adenovirus type 2 or 5 (Ad 2 or Ad 5) or an adenovirus of animal origin (French patent application No. FR-93.05954).

Retrovirus vectors and adeno-associated virus vectors are generally understood to be the recombinant gene delivery systems of choice for the transfer of exogenous polynucleotides in vivo, particularly to mammals, including humans. These vectors provide efficient delivery of genes into cells, and the transferred nucleic acids are stably integrated into the chromosomal DNA of the host.

Particularly preferred retroviruses for the preparation or construction of retroviral in vitro or in vivo gene delivery vehicles of the present invention include retroviruses selected from the group consisting of Mink-Cell Focus Inducing Virus, Murine Sarcoma Virus, Reticuloendotheliosis virus and Rous Sarcoma virus. Particularly preferred Murine Leukemia Viruses include the 4070A and the 1504A viruses, Abelson (ATCC No VR-999), Friend (ATCC No VR-245), Gross (ATCC No VR-590), Rauscher (ATCC No VR-998) and Moloney Murine Leukemia Virus (ATCC No VR-190; PCT Application No WO 94/24298). Particularly preferred Rous Sarcoma Viruses include Bryan high titer (ATCC Nos VR-334, VR-657, VR-726, VR-659 and VR-728). Other preferred retroviral vectors are those described in Roth et al. (1996), PCT Application No WO 93/25234, PCT Application No WO 94/06920, Roux et al., ((1989) Proc Natl Acad Sci USA December;86(23): 9079–83), Julan et al., (1992) J. Gen. Virol. 3:3251–3255 and Neda et al., ((1991) J Biol Chem August 5;266(22): 14143–6).

Yet another viral vector system that is contemplated by the invention consists of the adeno-associated virus (AAV). The adeno-associated virus is a naturally occurring defective virus that requires another virus, such as an adenovirus or a herpes virus, as a helper virus for efficient replication and a productive life cycle (Muzyczka et al., (1992) Curr Top Microbiol Immunol;158:97–129). It is also one of the few viruses that may integrate its DNA into non-dividing cells, and exhibits a high frequency of stable integration (Flotte et al., (1992) Am J Respir Cell Mol Biol September;7(3): 349–56; Samulski et al., (1989) J Virol September;63(9): 3822–8; McLaughlin et al., (1989) Am. J. Hum. Genet. 59:561–569). One advantageous feature of AAV derives from its reduced efficacy for transducing primary cells relative to transformed cells.

5) Delivery of the Recombinant Vectors

In order to effect expression of the polynucleotides of the invention, these constructs must be delivered into a cell. This delivery may be accomplished in vitro, as in laboratory procedures for transforming cell lines, or in vivo or ex vivo, as in the treatment of certain disease states.

One mechanism is viral infection where the expression construct is encapsulated in an infectious viral particle.

Several non-viral methods for the transfer of polynucleotides into cultured mammalian cells are also contemplated by the present invention, and include, without being limited to, calcium phosphate precipitation (Graham et al., (1973) Virology August;54(2):536–9; Chen et al., (1987) Mol Cell Biol August;7(8):2745–52), DEAE-dextran (Gopal, (1985) Mol Cell Biol May;5(5):1188–90), electroporation (Tur-Kaspa et al., (1986) Mol Cell Biol February;6(2):716–8; Potter et al., (1984) Proc Natl Acad Sci USA November;81 (22):7161–5.), direct microinjection (Harland et al., (1985) J Cell Biol September;101(3):1094–9), DNA-loaded liposomes (Nicolau et al., (1982) Biochim Biophys Acta October 11;721(2):185–90; Fraley et al., (1979) Proc Natl Acad Sci USA July;76(7):3348–52), and receptor-mediated transfection (Wu and Wu, (1987) J Biol Chem April 5;262(10): 4429–32; Wu and Wu (1988) Biochemistry February 9;27 (3):887–92). Some of these techniques may be successfully adapted for in vivo or ex vivo use.

Once the expression polynucleotide has been delivered into the cell, it may be stably integrated into the genome of the recipient cell. This integration may be in the cognate location and orientation via homologous recombination (gene replacement) or it may be integrated in a random, non specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle.

One specific embodiment for a method for delivering a protein or peptide to the interior of a cell of a vertebrate in vivo comprises the step of introducing a preparation comprising a physiologically acceptable carrier and a naked polynucleotide operatively coding for the polypeptide of interest into the interstitial space of a tissue comprising the cell, whereby the naked polynucleotide is taken up into the interior of the cell and has a physiological effect. This is particularly applicable for transfer in vitro but it may be applied to in vivo as well.

Compositions for use in vitro and in vivo comprising a "naked" polynucleotide are described in PCT application No. WO 90/11092 (Vical Inc.) and also in PCT application No. WO 95/11307 (Institut Pasteur, INSERM, Université d'Ottawa) as well as in the articles of Tascon et al. (1996) Nature Medicine. 2(8):888–892 and of Huygen et al. ((1996) Nat Med August;2(8):893–8).

In still another embodiment of the invention, the transfer of a naked polynucleotide of the invention, including a polynucleotide construct of the invention, into cells may be proceeded with a particle bombardment (biolistic), said particles being DNA-coated microprojectiles accelerated to a high velocity allowing them to pierce cell membranes and enter cells without killing them, such as described by Klein et al. ((1990) Curr Genet February;17(2):97–103).

In a further embodiment, the polynucleotide of the invention may be entrapped in a liposome (Ghosh and Bacchawat, (1991) Targeted Diagn Ther;4:87–103; Wong et al., (1980) Gene 10:87–94; Nicolau et al., (1987) Methods Enzymol.;149:157–76). These liposomes may further be targeted to cells expressing LSR by incorporating leptin, triglycerides, ACRP30, or other known LSR ligands into the liposome membrane.

In a specific embodiment, the invention provides a composition for the in vivo production of an GMP-1 globular head polypeptide described herein. It comprises a naked polynucleotide operatively coding for this polypeptide, in solution in a physiologically acceptable carrier, and suitable for introduction into a tissue to cause cells of the tissue to express the said polypeptide.

The amount of vector to be injected to the desired host organism varies according to the site of injection. As an indicative dose, it will be injected between 0.1 and 100 μg of the vector in an animal body, preferably a mammal body, for example a mouse body.

In another embodiment of the vector according to the invention, it may be introduced in vitro in a host cell, preferably in a host cell previously harvested from the animal to be treated and more preferably a somatic cell such as a muscle cell. In a subsequent step, the cell that has been transformed with the vector coding for the desired GMP-1 globular head polypeptide or the desired fragment thereof is reintroduced into the animal body in order to deliver the recombinant protein within the body either locally or systemically.

Screening for compounds that modulate Adipsin expression and/or biological activity The present invention further relates to compounds able to modulate Adipsin expression and/or biological activity and methods to use these compounds. Such compounds may interact with the regulatory sequences of Adipsin genes or they may interact with Adipsin polypeptides directly or indirectly.

Compounds Interacting with Adipsin Regulatory Sequences

The present invention also concerns a method for screening substances or molecules that are able to interact with the regulatory sequences of an Adipsin gene, such as for example promoter or enhancer sequences in untranscribed regions of the genomic DNA, as determined using any techniques known to those skilled in the art including, or such as regulatory sequences located in untranslated regions of Adipsin mRNA.

Sequences within untranscribed or untranslated regions of polynucleotides of the invention may be identified by comparison to databases containing known regulatory sequence such as transcription start sites, transcription factor binding sites, promoter sequences, enhancer sequences, 5'UTR and 3'UTR elements (Pesole et al., 2000; http://see Worldwide Website: igs-server.cnrs.mrs.fr/~gauthere/UTR/index.html). Alternatively, the regulatory sequences of interest may be identified through conventional mutagenesis or deletion analyses of reporter plasmids.

Following the identification of potential Adipsin regulatory sequences, proteins that interact with these regulatory sequences may be identified as described below.

Gel retardation assays may be performed independently in order to screen candidate molecules that are able to interact with the regulatory sequences of the Adipsin gene, such as described by Fried and Crothers (1981), Garner and Revzin (1981) and Dent and Latchman (1993), the teachings of these publications being herein incorporated by reference. These techniques are based on the principle according to which a DNA or mRNA fragment that is bound to a protein migrates slower than the same unbound DNA or mRNA fragment. Briefly, the target nucleotide sequence is labeled. Then the labeled target nucleotide sequence is brought into contact with either a total nuclear extract from cells containing regulation factors, or with different candidate molecules to be tested. The interaction between the target regulatory sequence of the Adipsin gene and the candidate molecule or the regulation factor is detected after gel or capillary electrophoresis through a retardation in the migration.

Nucleic acids encoding proteins which are able to interact with the promoter sequence of the Adipsin gene, more particularly a nucleotide sequence selected from the group consisting of the polynucleotides of the 5' and 3' regulatory region or a fragment or variant thereof, may be identified by using a one-hybrid system, such as that described in the booklet enclosed in the Matchmaker One-Hybrid System kit from Clontech (Catalog Ref. n° K1603-1), the technical teachings of which are herein incorporated by reference. Briefly, the target nucleotide sequence is cloned upstream of a selectable reporter sequence and the resulting polynucleotide construct is integrated in the yeast genome (*Saccharomyces cerevisiae*). Preferably, multiple copies of the target sequences are inserted into the reporter plasmid in tandem. The yeast cells containing the reporter sequence in their genome are then transformed with a library comprising fusion molecules between cDNA encoding candidate proteins for binding onto the regulatory sequences of the Adipsin gene and sequences encoding the activator domain of a yeast transcription factor such as GAL4. The recombinant yeast cells are plated in a culture broth for selecting cells expressing the reporter sequence. The recombinant yeast cells thus selected contain a fusion protein that is able to bind onto the target regulatory sequence of the Adipsin gene. Then, the cDNA encoding the fusion proteins are sequenced and may be cloned into expression or transcription vectors in vitro. The binding of the encoded polypeptides to the target regulatory sequences of the Adipsin gene may be confirmed by techniques familiar to the one skilled in the art, such as gel retardation assays or DNAse protection assays.

LIGANDS Interacting with Adipsin Polypeptides

For the purpose of the present invention, a LIGAND means a molecule, such as a protein, a peptide, an antibody or any synthetic chemical compound capable of binding to an Adipsin protein or one of its fragments or variants or to modulate the expression of the polynucleotide coding for Adipsin or a fragment or variant thereof.

In the LIGAND screening method according to the present invention, a biological sample or a defined molecule to be tested as a putative LIGAND of an Adipsin protein is brought into contact with the corresponding purified Adipsin protein, for example the corresponding purified recombinant Adipsin protein produced by a recombinant cell host as described herein, in order to form a complex between this protein and the putative LIGAND molecule to be tested.

As an illustrative example, to study the interaction of an Adipsin protein, or a fragment comprising a contiguous span of at least 6 amino acids, preferably at least 8 to 10 amino acids, more preferably at least 12, 15, 20, 25, 30, 40, 50, or 100 amino acids of a polypeptide selected from the group consisting of sequences of SEQ ID NOs: 2, 4 or 6 and polypeptides encoded by the clone inserts of the deposited clone pool, with drugs or small molecules, such as molecules generated through combinatorial chemistry approaches, the microdialysis coupled to HPLC method described by Wang et al. (1997) or the affinity capillary electrophoresis method described by Bush et al. (1997), the disclosures of which are incorporated by reference, can be used. In preferred embodiments, said fragment is selected from amino acids 21–253 or 26–253 of SEQ ID NO: 2 where amino acid 21 of SEQ ID NO: 2 is predicted to be the N-terminal amino acid of the mature Adipsin polypeptide absent the putative signal peptide and amino acid 26 of SEQ ID NO: 2 is predicted to be the N-terminal amino acid of the mature Adipsin polypeptide absent both the putative signal peptide and the putative activation peptide, amino acids 20–253 or 26–253 of SEQ ID NO: 4 where amino acid 20 of SEQ ID NO: 4 is predicted to be the N-terminal amino acid of the mature Adipsin polypeptide absent the putative signal peptide and amino acid 26 of SEQ ID NO: 4 is predicted to be the N-terminal amino acid of the mature Adipsin polypeptide absent both the putative signal peptide and the putative activation peptide, or amino acids 1–228 or 2–228 of SEQ ID NO: 6.

In further methods, peptides, drugs, fatty acids, lipoproteins, or small molecules which interact with an Adipsin protein, or a fragment comprising a contiguous span of at least 6 amino acids, preferably at least 8 to 10 amino acids, more preferably at least 12, 15, 20, 25, 30, 40, 50, or 100 amino acids of a polypeptide selected from the group consisting of sequences of SEQ ID NOs: 2, 4 or 6 and polypeptides encoded by the clone inserts of the deposited clone pool may be identified using assays such as the following. In preferred embodiments, said fragment is selected from amino acids 21–253 or 26–253 of SEQ ID NO: 2, amino acids 21–253 or 26–253 of SEQ ID NO: 2 where amino acid 21 of SEQ ID NO: 2 is predicted to be the N-terminal amino acid of the mature Adipsin polypeptide absent the putative signal peptide and amino acid 26 of SEQ ID NO: 2 is predicted to be the N-terminal amino acid of the mature Adipsin polypeptide absent both the putative signal peptide and the putative activation peptide, amino acids 20–253 or 26–253 of SEQ ID NO: 4 where amino acid 20 of SEQ ID NO: 4 is predicted to be the N-terminal amino acid of the mature Adipsin polypeptide absent the putative signal peptide and amino acid 26 of SEQ ID NO: 4 is predicted to be the N-terminal amino acid of the mature Adipsin polypeptide absent both the putative signal peptide and the putative activation peptide, or amino acids 1–228 or 2–228 of SEQ ID NO: 6. The molecule to be tested for binding is labeled with a detectable label, such as a fluorescent, radioactive, or enzymatic tag and placed in contact with immobilized Adipsin protein, or a fragment thereof under conditions that permit specific binding to occur. After removal of non-specifically bound molecules, bound molecules are detected using appropriate means.

Various candidate substances or molecules can be assayed for interaction with an Adipsin polypeptide. These substances or molecules include, without being limited to, natural or synthetic organic compounds or molecules of biological origin such as polypeptides. When the candidate substance or molecule comprises a polypeptide, this polypeptide may be the resulting expression product of a phage clone belonging to a phage-based random peptide library, or alternatively the polypeptide may be the resulting expression product of a cDNA library cloned in a vector suitable for performing a two-hybrid screening assay.

A. Candidate Ligands Obtained from Random Peptide Libraries

In a particular embodiment of the screening method, the putative LIGAND is the expression product of a DNA insert contained in a phage vector (Parmeley and Smith, 1988). Specifically, random peptide phages libraries are used. The random DNA inserts encode for peptides of 8 to 20 amino acids in length (Oldenburg et al., 1992; Valadon et al., 1996; Lucas, 1994; Westerink, 1995; Felici et al., 1991), which disclosures are hereby incorporated by reference in their entireties. According to this particular embodiment, the recombinant phages expressing a protein that binds to an immobilized Adipsin protein is retained and the complex formed between the Adipsin protein and the recombinant phage may be subsequently immunoprecipitated by a polyclonal or a monoclonal antibody directed against the Adipsin protein.

Once the LIGAND library in recombinant phages has been constructed, the phage population is brought into contact with the immobilized Adipsin protein. Then the preparation of complexes is washed in order to remove the non-specifically bound recombinant phages. The phages that bind specifically to the Adipsin protein are then eluted by a buffer (acid pH) or immunoprecipitated by the monoclonal antibody produced by the hybridoma anti-Adipsin, and this phage population is subsequently amplified by an over-infection of bacteria (for example $E.$ $coli$). The selection step may be repeated several times, preferably 2–4 times, in order to select the more specific recombinant phage clones. The last step comprises characterizing the peptide produced by the selected recombinant phage clones either by expression in infected bacteria and isolation, expressing the phage insert in another host-vector system, or sequencing the insert contained in the selected recombinant phages.

B. Candidate Ligands Obtained by Competition Experiments.

Alternatively, peptides, drugs or small molecules which bind to an Adipsin protein or fragment thereof comprising a contiguous span of at least 6 amino acids, preferably at least 8 to 10 amino acids, more preferably at least 12, 15, 20, 25, 30, 40, 50, or 100 amino acids of a polypeptide selected from the group consisting of sequences of SEQ ID NOs: 2, 4 or 6 and polypeptides encoded by the clone inserts of the deposited clone pool, may be identified in competition experiments. In preferred embodiments, said fragment is selected from amino acids 21–253 or 26–253 of SEQ ID NO: 2 where amino acid 21 of SEQ ID NO: 2 is predicted to be the N-terminal amino acid of the mature Adipsin polypeptide absent the putative signal peptide and amino acid 26 of SEQ ID NO: 2 is predicted to be the N-terminal amino acid of the mature Adipsin polypeptide absent both the putative signal peptide and the putative activation peptide, amino acids 20–253 or 26–253 of SEQ ID NO: 4 where amino acid 20 of SEQ ID NO: 4 is predicted to be the N-terminal amino acid of the mature Adipsin polypeptide absent the putative signal peptide and amino acid 26 of SEQ ID NO: 4 is predicted to be the N-terminal amino acid of the mature Adipsin polypeptide absent both the putative signal peptide and the putative activation peptide, or amino acids 1–228 or 2–228 of SEQ ID NO: 6. In such assays, the Adipsin protein, or a fragment thereof, is immobilized to a surface, such as a plastic plate. Increasing amounts of the peptides, drugs or small molecules are placed in contact with the immobilized Adipsin protein, or a fragment thereof, in the presence of a detectable labeled known Adipsin protein LIGAND. For example, the Adipsin LIGAND may be detectably labeled with a fluorescent, radioactive, or enzymatic tag. The ability of the test molecule to bind the Adipsin protein, or a fragment thereof, is determined by measuring the amount of detectably labeled known LIGAND bound in the presence of the test molecule. A decrease in the amount of known LIGAND bound to the Adipsin protein, or a fragment thereof, when the test molecule is present indicated that the test molecule is able to bind to the Adipsin protein, or a fragment thereof.

C. Candidate Ligands Obtained by Affinity Chromatography.

Proteins or other molecules interacting with an Adipsin protein, or a fragment thereof comprising a contiguous span of at least 6 amino acids, preferably at least 8 to 10 amino acids, more preferably at least 12, 15, 20, 25, 30, 40, 50, or 100 amino acids of a polypeptide selected from the group consisting of sequences of SEQ ID NOs: 2, 4 or 6 and polypeptides encoded by the clone inserts of the deposited clone pool, can also be found using affinity columns which contain the Adipsin protein, or a fragment thereof. In preferred embodiments, said fragment is selected from amino acids 21–253 or 26–253 of SEQ ID NO: 2 where amino acid 21 of SEQ ID NO: 2 is predicted to be the N-terminal amino acid of the mature Adipsin polypeptide absent the putative signal peptide and amino acid 26 of SEQ ID NO: 2 is predicted to be the N-terminal amino acid of the mature Adipsin polypeptide absent both the putative signal peptide and the putative activation peptide, amino acids 20–253 or 26–253 of SEQ ID NO: 4 where amino acid 20 of SEQ ID NO: 4 is predicted to be the N-terminal amine acid of the mature Adipsin polypeptide absent the putative signal peptide and amino acid 26 or SEQ ID NO: 4 is predicted to be the N-terminal amino acid of the mature Adipsin polypeptide absent both the putative signal peptide and the putative activation peptide, or amino acids 1–228 or 2–228 of SEQ ID NO: 6. The Adipsin protein, or a fragment thereof, may be attached to the column using conventional techniques including chemical coupling to a suitable column matrix such as agarose, AFFIGEL, or other matrices familiar to those of skill in art. In some embodiments of this method, the affinity column contains chimeric proteins in which the Adipsin protein, or a fragment thereof, is fused to glutathion S transferase (GST). A mixture of cellular proteins or pool of expressed proteins as described above is applied to the affinity column. Proteins or other molecules interacting with the Adipsin protein, or a fragment thereof, attached to the column can then be isolated and analyzed on 2-D electrophoresis gel as described in Ramunsen et al. (1997), the disclosure of which is incorporated by reference. Alternatively, the proteins retained on the affinity column can be purified by electrophoresis based methods and sequenced. The same method can be used to isolate antibodies, to screen phage display products, or to screen phage display human antibodies.

D. Candidate Ligands Obtained by Optical Biosensor Methods

Proteins interacting with an Adipsin protein, or a fragment comprising a contiguous span of at least 6 amino acids, preferably at least 8 to 10 amino acids, more preferably at least 12, 15, 20, 25, 30, 40, 50, or 100 amino acids of a polypeptide selected from the group consisting of sequences of SEQ ID NOs: 2, 4 or 6 and polypeptides encoded by the clone inserts of the deposited clone pool, can also be screened by using an Optical Biosensor as described in Edwards and Leatherbarrow (1997) and also in Szabo et al. (1995), the disclosures of which are incorporated by reference. In preferred embodiments, said fragment is selected from amino acids 21–253 or 26–253 of SEQ ID NO: 2 where amino acid 21 of SEQ ID NO: 2 is predicted to be the N-terminal amino acid of the mature Adipsin polypeptide absent the putative signal peptide and amino acid 26 of SEQ ID NO: 2 is predicted to be the N-terminal amino acid of the mature Adipsin polypeptide absent both the putative signal peptide and the putative activation peptide, amino acids 20–253 or 26–253 of SEQ ID NO: 4 where amino acid 20 of SEQ ID NO: 4 is predicted to be the N-terminal amino acid of the mature Adipsin polypeptide absent the putative signal peptide and amino acid 26 of SEQ ID NO: 4 is predicted to be the N-terminal amino acid of the mature Adipsin polypeptide absent both the putative signal peptide and the putative activation peptide, or amino acids 1–228 or 2–228 of SEQ ID NO: 6. This technique permits the detection of interactions between molecules in real time, without the need of labeled molecules. This technique is based on the surface plasmon resonance (SPR) phenomenon. Briefly, the candidate LIGAND molecule to be tested is attached to a surface (such as a carboxymethyl dextran matrix). A light beam is directed towards the side of the surface that does not contain the sample to be tested and is reflected by said surface. The SPR phenomenon causes a decrease in the intensity of the reflected light with a specific association of angle and wavelength. The binding of candidate LIGAND molecules cause a change in the refraction index on the surface, which change is detected as a change in the SPR signal. For screening of candidate LIGAND molecules or substances that are able to interact with the Adipsin protein, or a fragment thereof, the Adipsin protein, or a fragment thereof, is immobilized onto a surface. This surface comprises one side of a cell through which flows the candidate molecule to be assayed. The binding of the candidate molecule on the Adipsin protein, or a fragment thereof, is detected as a change of the SPR signal. The candidate molecules tested may be proteins, peptides, carbohydrates, lipids, or small molecules generated by combinatorial chemistry. This technique may also be performed by immobilizing eukaryotic or prokaryotic cells or lipid vesicles exhibiting an endogenous or a recombinantly expressed Adipsin protein at their surface.

The main advantage of the method is that it allows the determination of the association rate between the Adipsin protein and molecules interacting with the Adipsin protein. It is thus possible to select specifically LIGAND molecules interacting with the Adipsin protein, or a fragment thereof, through strong or conversely weak association constants.

E. Candidate Ligands Obtained Through a Two-hybrid Screening Assay.

The yeast two-hybrid system is designed to study protein-protein interactions in vivo (Fields and Song, 1989), which disclosure is hereby incorporated by reference in its entirety, and relies upon the fusion of a bait protein to the DNA binding domain of the yeast Gal4 protein. This technique is also described in the U.S. Pat. No. 5,667,973 and the U.S. Pat. No. 5,283,173, the technical teachings of both patents being herein incorporated by reference.

The general procedure of library screening by the two-hybrid assay may be performed as described by Harper et al. (1993) or as described by Cho et al. (1998) or also Fromont-Racine et al. (1997), which disclosures are hereby incorporated by reference in their entireties.

The bait protein or polypeptide comprises, consists essentially of, or consists of an Adipsin polypeptide or a fragment thereof comprising a contiguous span of at least 6 amino acids, preferably at least 8 to 10 amino acids, more preferably at least 12, 15, 20, 25, 30, 40, 50, or 100 amino acids of a polypeptide selected from the group consisting of sequences of SEQ ID NOs: 2, 4 or 6 and polypeptides encoded by the clone inserts of the deposited clone pool. In preferred embodiments, said fragment is selected from amino acids 21–253 or 26–253 of SEQ ID NO: 2 where amino acid 21 of SEQ ID NO: 2 is predicted to be the N-terminal amino acid of the mature Adipsin polypeptide absent the putative signal peptide and amino acid 26 of SEQ ID NO: 2 is predicted to be the N-terminal amino acid of the mature Adipsin polypeptide absent both the putative signal peptide and the putative activation peptide, amino acids 20–253 or 26–253 of SEQ ID NO: 4 where amino acid 20 of SEQ ID NO: 4 is predicted to be the N-terminal amino acid of the mature Adipsin polypeptide absent the putative signal peptide and amino acid 26 of SEQ ID NO: 4 is predicted to be the N-terminal amino acid of the mature Adipsin polypeptide absent both the putative signal peptide and the putative activation peptide, or amino acids 1–228 or 2–228 of SEQ ID NO: 6.

More precisely, the nucleotide sequence encoding the Adipsin polypeptide or a fragment or variant thereof is fused to a polynucleotide encoding the DNA binding domain of the GAL4 protein, the fused nucleotide sequence being inserted in a suitable expression vector, for example pAS2 or pM3.

Then, a human cDNA library is constructed in a specially designed vector, such that the human cDNA insert is fused to a nucleotide sequence in the vector that encodes the transcriptional domain of the GAL4 protein. Preferably, the vector used is the pACT vector. The polypeptides encoded by the nucleotide inserts of the human cDNA library are termed "prey" polypeptides.

A third vector contains a detectable marker gene, such as beta galactosidase gene or CAT gene that is placed under the control of a regulation sequence that is responsive to the binding of a complete Gal4 protein containing both the transcriptional activation domain and the DNA binding domain. For example, the vector pG5EC may be used.

Two different yeast strains are also used. As an illustrative but non limiting example the two different yeast strains may be the following:

Y190, the phenotype of which is (MATa, Leu2-3, 112 ura3-12, trp1-901, his3-D200, ade2-101, gal4Dgal180D URA3 GAL-LacZ, LYS GAL-HIS3, cyh$^r$);

Y187, the phenotype of which is (MATa gal4 gal80 his3 trp1-901 ade2-101 ura3-52 leu2-3, -112 URA3 GAL-lacZmet$^-$), which is the opposite mating type of Y190.

Briefly, 20 µg of pAS2/Adipsin and 20 µg of pACT-cDNA library are co-transformed into yeast strain Y190. The transformants are selected for growth on minimal media lacking histidine, leucine and tryptophan, but containing the histidine synthesis inhibitor 3-AT (50 mM). Positive colonies are screened for beta galactosidase by filter lift assay. The double positive colonies (His$^+$, beta-gal$^+$) are then grown on plates lacking histidine, leucine, but containing tryptophan and cycloheximide (10 mg/ml) to select for loss of pAS2/Adipsin plasmids but retention of pACT-cDNA library plasmids. The resulting Y190 strains are mated with Y187 strains expressing Adipsin or non-related control proteins; such as cyclophilin B, lamin, or SNF1, as Gal4 fusions as described by Harper et al. (1993) and by Brain et al. (1993), which disclosures are hereby incorporated by reference in their entireties, and screened for beta galactosidase by filter lift assay. Yeast clones that are beta gal- after mating with the control Gal4 fusions are considered false positives.

In another embodiment of the two-hybrid method according to the invention, interaction between the Adipsin or a fragment or variant thereof with cellular proteins may be assessed using the Matchmaker Two Hybrid System 2 (Catalog No. K1604-1, Clontech). As described in the manual accompanying the kit, the disclosure of which is incorporated herein by reference, nucleic acids encoding the Adipsin protein or a portion thereof, are inserted into an expression vector such that they are in frame with DNA encoding the DNA binding domain of the yeast transcriptional activator GAL4. A desired cDNA, preferably human cDNA, is inserted into a second expression vector such that they are in frame with DNA encoding the activation domain of GAL4. The two expression plasmids are transformed into yeast and the yeast are plated on selection medium which selects for expression of selectable markers on each of the expression vectors as well as GAL4 dependent expression of the HIS3 gene. Transformants capable of growing on medium lacking histidine are screened for GAL4 dependent lacZ expression. Those cells that are positive in both the histidine selection and the lacZ assay contain interaction between Adipsin and the protein or peptide encoded by the initially selected cDNA insert.

Compounds Modulating Adipsin Biological Activity

Another method of screening for compounds that modulate gene expression and/or biological activity is by measuring the effects of test compounds on specific biological activity, wherein said activity is selected from the group consisting of lipid partitioning, lipid metabolism, and insulin-like activity or as described herein, in a host cell. In one embodiment, the present invention relates to a method of identifying an agent that alters gene activity, wherein a nucleic acid construct comprising a nucleic acid that encodes a mammalian gene polypeptide is introduced into a host cell. The host cells produced are maintained under conditions appropriate for expression of the encoded mammalian gene polypeptides, whereby the nucleic acid is expressed. The host cells are then contacted with a compound to be assessed (an agent) and an activity of the cells is detected in the presence of the compound to be assessed, wherein said activity is selected from the group consisting of lipid partitioning, lipid metabolism, and insulin-like activity or as described herein. Detection of a change in said activity in the presence of the agent indicates that the agent alters Adipsin activity. In a particular embodiment, the invention relates to a method of identifying an agent which is an activator of Adipsin activity, wherein detection of an increase of said activity, said activity being selected from the group consisting of lipid partitioning, lipid metabolism, and insulin-like activity or as described herein, in the presence of the agent indicates that the agent activates Adipsin activity. In another particular embodiment, the invention relates to a method of identifying an agent which is an inhibitor of Adipsin activity, wherein detection of a decrease of said activity, said activity being selected from the group consisting of lipid partitioning, lipid metabolism, and insulin-like activity or as described herein, in the presence of the agent indicates that the agent inhibits Adipsin activity.

Detection of a change in said Adipsin activity, said activity being selected from the group consisting of lipid partitioning, lipid metabolism, and insulin-like activity or as described herein, can be performed using a variety of techniques as described for representative activities in examples provided herein. For example, said activity can be used in conjunction with recombinant cells expressing an Adipsin polypeptide. Decrease of said activity in the presence of the test compound, indicates a decrease of Adipsin activity, said activity being selected from the group consisting of lipid partitioning, lipid metabolism, and insulin-like activity or as described herein, and increase of said activity in the presence of the test compound, indicates an increase for cases Adipsin activity, wherein said activity is selected from the group consisting of lipid partitioning, lipid metabolism, and insulin-like activity. If a decrease in said activity is observed in Adipsin expressing cells, but not in control cells, then the test compound is an inhibitor of Adipsin. If an increase in said activity is observed in Adipsin expressing cells, but not in control cells, then the test compound is an activator of Adipsin.

In a particular embodiment a high throughput screen can be used to identify agents that activate (enhance) or inhibit Adipsin activity (See e.g., PCT publication WO 98/45438, which disclosure is hereby incorporated by reference in its entirety). For example, the method of identifying an agent that alters Adipsin activity can be performed as follows. A nucleic acid construct comprising polynucleotide that encodes a mammalian Adipsin polypeptide is introduced into a host cell to produce recombinant host cells. The recombinant host cells produced are maintained under conditions appropriate for expression of the encoded mammalian Adipsin polypeptide, whereby the nucleic acid is expressed. An indicator of Adipsin activity and the compound to be assessed are added to the recombinant host cells; the resulting combination is referred to as a test sample. The indicator signal is detected. A decrease of indicator signal in the presence of the test compound occurs with a decrease in the Adipsin activity, wherein said activity is selected from the group consisting of lipid partitioning, lipid metabolism, and insulin-like activity of the cells, which indicates that the agent is an inhibitor of Adipsin. Conversely, an increase of indicator signal in the presence of the test compound occurs with an increase in the Adipsin activity, wherein said activity is selected from the group consisting of lipid partitioning, lipid metabolism, and insulin-like activity of the cells, which indicates that the agent is an activator of Adipsin. A control can be used in the methods of detecting agents that alter Adipsin activity. For example, the control sample includes the same reagents but lacks the compound or agent being assessed; it is treated in the same manner as the test sample.

Methods of Screening for Compounds Modulating Adipsin Expression and/or Activity The present invention also relates to methods of screening compounds for their ability to modulate (e.g. increase or inhibit) the activity or expression of Adipsin. More specifically, the present invention relates to methods of testing compounds for their ability either to increase or to decrease expression or activity of Adipsin. The assays are performed in vitro or in vivo.

In Vitro Methods

In vitro, cells expressing Adipsin are incubated in the presence and absence of the test compound. By determining the level of Adipsin expression in the presence of the test compound or the level of Adipsin activity in the presence of the test compound, compounds can be identified that suppress or enhance Adipsin expression or activity. Alternatively, constructs comprising an Adipsin regulatory sequence operably linked to a reporter gene (e.g. luciferase, chloramphenicol acetyl transferase, LacZ, green fluorescent protein, etc.) can be introduced into host cells and the effect of the test compounds on expression of the reporter gene detected. Cells suitable for use in the foregoing assays include, but are not limited to, cells having the same origin as tissues or cell lines in which the polypeptide is known to be expressed.

Consequently, the present invention encompasses a method for screening molecules that modulate the expression of an Adipsin gene, said screening method comprising the steps of:

a) cultivating a prokaryotic or an eukaryotic cell that has been transfected with a nucleotide sequence encoding an Adipsin protein or a variant or a fragment thereof, placed under the control of its own promoter;

b) bringing into contact said cultivated cell with a molecule to be tested;

c) quantifying the expression of said Adipsin protein or a variant or a fragment thereof in the presence of said molecule.

Using DNA recombination techniques well known by the one skill in the art, the Adipsin protein encoding DNA sequence is inserted into an expression vector, downstream from its promoter sequence. As an illustrative example, the promoter sequence of the Adipsin gene is contained in the 5' untranscribed region of the Adipsin genomic DNA.

The quantification of the expression of an Adipsin protein may be realized either at the mRNA level (using for example Northern blots, RT-PCR, preferably quantitative RT-PCR with primers and probes specific for the Adipsin mRNA of interest) or at the protein level (using polyclonal or monoclonal antibodies in immunoassays such as ELISA or RIA assays, Western blots, or immunochemistry).

The present invention also concerns a method for screening substances or molecules that are able to increase, or in contrast to decrease, the level of expression of an Adipsin gene. Such a method may allow the one skilled in the art to select substances exerting a regulating effect on the expression level of an Adipsin gene and which may be useful as active ingredients included in pharmaceutical compositions for treating patients suffering from diseases/disorders associated with abnormal levels of Adipsin products, including but not restricted to obesity-related diseases/disorders and disorders associated with excessive weight loss. Obesity and obesity-related diseases and disorders include, but are not restricted to, obesity, insulin resistance, atherosclerosis, atheromatous disease, heart disease, hypertension, stroke, Syndrome X, Noninsulin Dependent Diabetes Mellitus (NIDDM, or Type II diabetes) and Insulin Dependent Diabetes Mellitus (IDDM or Type I diabetes). Diabetes-related complications include, but are not restricted to, microangiopathic lesions, ocular lesions, retinopathy, neuropathy, renal lesions. Heart disease includes, but is not limited to, cardiac insufficiency, coronary insufficiency, and high blood pressure. Other obesity-related disorders include, but are not restricted to, hyperlipidemia and hyperuricemia. Disorders associated with excessive weight loss include, but are not restricted to, cachexia, wasting, cancer-related weight loss, AIDS-related weight loss, chronic inflammatory disease-related weight loss, anorexia, and bulimia.

The Adipsin or LIGAND polypeptide fragments or antagonists thereof may also be used to treat dyslexia, attention-deficit disorder (ADD), attention-deficit/hyperactivity disorder (ADHD), and psychiatric disorders such as schizophrenia by modulating fatty acid metabolism, more specifically, the production of certain long-chain polyunsaturated fatty acids.

Thus, also part of the present invention is a method for screening a candidate molecule that modulates the expression of an Adipsin gene, this method comprises the following steps:

a) providing a recombinant cell host containing a nucleic acid, wherein said nucleic acid comprises an Adipsin 5' regulatory region or a regulatory active fragment or variant thereof, operably linked to a polynucleotide encoding a detectable protein;

b) obtaining a candidate molecule; and c) determining the ability of said candidate molecule to modulate the expression levels of said polynucleotide encoding the detectable protein.

In a further embodiment, said nucleic acid comprising an Adipsin 5' regulatory region or a regulatory active fragment or variant thereof, includes the 5'UTR region of an Adipsin cDNA selected from the group comprising of the 5'UTRs of the sequences of SEQ ID Nos 1, sequences of clones inserts of the deposited clone pool, regulatory active fragments and variants thereof. In a more preferred embodiment of the above screening method, said nucleic acid includes a promoter sequence which is endogenous with respect to the Adipsin 5'UTR sequence. In another more preferred embodiment of the above screening method, said nucleic acid includes a promoter sequence which is exogenous with respect to the Adipsin 5'UTR sequence defined therein.

Preferred polynucleotides encoding a detectable protein are polynucleotides encoding beta galactosidase, green fluorescent protein (GFP) and chloramphenicol acetyl transferase (CAT).

The invention further relates to a method for the production of a pharmaceutical composition comprising a method of screening a candidate molecule that modulates the expression of an Adipsin gene and furthermore mixing the identified molecule with a pharmaceutically acceptable carrier.

The invention also pertains to kits for the screening of a candidate substance modulating the expression of an Adipsin gene. Preferably, such kits comprise a recombinant vector that allows the expression of an Adipsin 5' regulatory region or a regulatory active fragment or a variant thereof, operably linked to a polynucleotide encoding a detectable protein or an Adipsin protein or a fragment or a variant thereof. More preferably, such kits include a recombinant vector that comprises a nucleic acid including the 5'UTR region of an Adipsin cDNA selected from the group comprising the 5'UTRs of the sequences of SEQ ID No 1, sequences of clones inserts of the deposited clone pool, regulatory active fragments and variants thereof, being operably linked to a polynucleotide encoding a detectable protein.

For the design of suitable recombinant vectors useful for performing the screening methods described above, it will be referred to the section of the present specification wherein the preferred recombinant vectors of the invention are detailed.

Another object of the present invention comprises methods and kits for the screening of candidate substances that interact with an Adipsin polypeptide, fragments or variants thereof. By their capacity to bind covalently or non-covalently to an Adipsin protein, fragments or variants thereof, these substances or molecules may be advantageously used both in vitro and in vivo.

In vitro, said interacting molecules may be used as detection means in order to identify the presence of an Adipsin protein in a sample, preferably a biological sample.

A method for the screening of a candidate substance that interact with an Adipsin polypeptide, fragments or variants thereof, said methods comprising the following steps:

a) providing a polypeptide comprising, consisting essentially of, or consisting of an Adipsin protein or a fragment comprising a contiguous span of at least 6 amino acids, preferably at least 8 to 10 amino acids, more preferably at least 12, 15, 20, 25, 30, 40, 50, or 100 amino acids of a polypeptide selected from the group consisting of sequences of SEQ ID NO:2 or 3 and polypeptides encoded by the clone inserts of the deposited clone pool;

b) obtaining a candidate substance;

c) bringing into contact said polypeptide with said candidate substance;

d) detecting the complexes formed between said polypeptide and said candidate substance.

The invention further relates to a method for the production of a pharmaceutical composition comprising a method for the screening of a candidate substance that interact with an Adipsin polypeptide, fragments or variants thereof and furthermore mixing the identified substance with a pharmaceutically acceptable carrier.

The invention further concerns a kit for the screening of a candidate substance interacting with the Adipsin polypeptide, wherein said kit comprises:

a) a polypeptide comprising, consisting essentially of, or consisting of an Adipsin protein or a fragment comprising a contiguous span of at least 6 amino acids, preferably at least 8 to 10 amino acids, more preferably at least 12, 15, 20, 25, 30, 40, 50, or 100 amino acids of a polypeptide selected from the group consisting of sequences of SEQ ID NO:2 or 3 and polypeptides encoded by the clone inserts of the deposited clone pool; and b) optionally means useful to detect the complex formed between said polypeptide or a variant thereof and the candidate substance.

In a preferred embodiment of the kit described above, said fragment is selected from amino acids 21–253 or 26–253 of SEQ ID NO: 2 where amino acid 21 of SEQ ID NO: 2 is predicted to be the N-terminal amino acid of the mature Adipsin polypeptide absent the putative signal peptide and amino acid 26 of SEQ ID NO: 2 is predicted to be the N-terminal amino acid of the mature Adipsin polypeptide absent both the putative signal peptide and the putative activation peptide, amino acids 20–253 or 26–253 of SEQ ID NO: 4 where amino acid 20 of SEQ ID NO: 4 is predicted to be the N-terminal amino acid of the mature Adipsin polypeptide absent the putative signal peptide and amino acid 26 of SEQ ID NO: 4 is predicted to be the N-terminal amino acid of the mature Adipsin polypeptide absent both the putative signal peptide and the putative activation peptide, or amino acids 1–228 or 2–228 of SEQ ID NO: 6.

In a preferred embodiment of the kit described above, the detection means comprises a monoclonal or polyclonal antibody binding to said Adipsin protein or fragment or variant thereof.

In Vivo Methods

Compounds that suppress or enhance Adipsin expression can also be identified using in vivo screens. In these assays, the test compound is administered (e.g. IV, IP, IM, orally, or otherwise), to the animal, for example, at a variety of dose levels. The effect of the compound on Adipsin expression is determined by comparing Adipsin levels, for example in tissues known to express the gene of interest, and using Northern blots, immunoassays, PCR, etc., as described above. Suitable test animals include rodents (e.g., mice and rats), primates. Humanized mice can also be used as test animals, that is mice in which the endogenous mouse protein is ablated (knocked out) and the homologous human protein added back by standard transgenic approaches. Such mice express only the human form of a protein. Humanized mice expressing only the human Adipsin can be used to study in vivo responses of obesity-related diseases/disorders and disorders associated with excessive weight loss in response to potential agents regulating Adipsin protein or mRNA levels. As an example, transgenic mice have been produced carrying the human apoE4 gene. They are then bred with a mouse line that lacks endogenous apoE, to produce an animal model carrying human proteins believed to be instrumental in development of Alzheimer's pathology. Such transgenic animals are useful for dissecting the biochemical and physiological steps of disease, and for development of therapies for disease intervention (Loring, et al, 1996) (incorporated herein by reference in its entirety).

Uses for Compounds Modulating Adipsin Expression and/or Biological Activity

Using in vivo (or in vitro) systems, it may be possible to identify compounds that exert a tissue specific effect, for example, that increase Adipsin expression or activity only in tissues of interest, such as muscle, liver, blood, and adipose tissue. Screening procedures such as those described above are also useful for identifying agents for their potential use in pharmacological intervention strategies. Agents that enhance Adipsin expression or stimulate its activity may thus be used to induce associated, for example, with obesity-related diseases/disorders or disorders associated with excessive weight loss. Obesity-related diseases and disorders such as obesity, insulin resistance, atherosclerosis, atheromatous disease, heart disease, hypertension, stroke, Syndrome X, Noninsulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, renal lesions. Heart disease includes, but is not limited to, cardiac insufficiency, coronary insufficiency, and high blood pressure.

The Adipsin or LIGAND polypeptide fragments or antagonists thereof may also be used to treat dyslexia, attention-deficit disorder (ADD), attention-deficit/hyperactivity disorder (ADHD), and psychiatric disorders such as schizophrenia by modulating fatty acid metabolism, more specifically, the production of certain long-chain polyunsaturated fatty acids.

In addition, agents that enhance Adipsin expression or activity may also be used to treat disorders such as other obesity-related diseases/disorders. Other obesity-related disorders include hyperlipidemia and hyperuricemia.

The Adipsin or LIGAND polypeptide fragments or antagonists thereof may also be used to treat dyslexia, attention-deficit disorder (ADD), attention-deficit/hyperactivity disorder (ADHD), and psychiatric disorders such as schizophrenia by modulating fatty acid metabolism, more specifically, the production of certain long-chain polyunsaturated fatty acids.

Compounds that suppress Adipsin expression or inhibit its activity can be used to treat disorders associated with excessive weight loss. Disorders associated with excessive weight loss include, but are not limited to, cachexia, wasting, cancer-related weight loss, AIDS-related weight loss, chronic inflammatory disease-related weight loss, anorexia, and bulimia.

The Adipsin or LIGAND polypeptide fragments or antagonists thereof may also be used to treat dyslexia, attention-deficit disorder (ADD), attention-deficit/hyperactivity disorder (ADHD), and psychiatric disorders such as schizophrenia by modulating fatty acid metabolism, more specifically, the production of certain long-chain polyunsaturated fatty acids.

In addition, agents that suppress Adipsin expression or inhibit its activity may also be used to treat disorders such as disorders associated with excessive weight loss. Disorders associates with excessive weight loss include, but are not limited to, cachexia, wasting, AIDS-related weight loss, chronic inflammatory disease-related weight loss, anorexia, and bulimia.

The Adipsin or LIGAND polypeptide fragments or antagonists thereof may also be used to treat dyslexia, attention-deficit disorder (ADD), attention-deficit/hyperactivity disorder (ADHD), and psychiatric disorders such as schizophrenia by modulating fatty acid metabolism, more specifically, the production of certain long-chain polyunsaturated fatty acids.

Also encompassed by the present invention is an agent that interacts with Adipsin directly or indirectly, and inhibits or enhances Adipsin expression and/or function. In one embodiment, the agent is an inhibitor that interferes with Adipsin directly (e.g., by binding Adipsin) or indirectly (e.g., by blocking the ability of Adipsin to have an Adipsin biological activity). In a particular embodiment, an inhibitor of Adipsin protein is an antibody specific for Adipsin protein or a functional portion of Adipsin; that is, the antibody binds an Adipsin polypeptide. For example, the antibody can be specific for a polypeptide encoded by one of the amino acid sequences of human genes (SEQ ID NOs: 2, 4 or 6), mammal Adipsin or portions thereof Alternatively, the inhibitor can be an agent other than an antibody (e.g., small organic molecule, protein or peptide) that binds Adipsin and blocks its activity. For example, the inhibitor can be an agent that mimics Adipsin structurally, but lacks its function. Alternatively, it can be an agent that binds to or interacts with a molecule that Adipsin normally binds with or interacts with, thus blocking Adipsin from doing so and preventing it from exerting the effects it would normally exert.

In another embodiment, the agent is an enhancer (activator) of Adipsin that increases the activity of Adipsin (increases the effect of a given amount or level of Adipsin), increases the length of time it is effective (by preventing its degradation or otherwise prolonging the time during which it is active) or both either directly or indirectly. For example, Adipsin polynucleotides and polypeptides can be used to identify therapeutic drugs.

The Adipsin sequences of the present invention can also be used to generate nonhuman gene knockout animals, such as mice, which lack an Adipsin gene or transgenically overexpress Adipsin. For example, such Adipsin gene knockout mice can be generated and used to obtain further insight into the function of Adipsin as well as assess the specificity of Adipsin activators and inhibitors. Also, over expression of Adipsin (e.g., human Adipsin) in transgenic mice can be used as a means of creating a test system for Adipsin activators and inhibitors (e.g., against human Adipsin). In addition, the Adipsin gene can be used to clone the Adipsin promoter/enhancer in order to identify regulators of Adipsin transcription. Adipsin gene knockout animals include animals that completely or partially lack the Adipsin gene and/or Adipsin activity or function. As described herein, it is likely that Adipsin plays a role in obesity-related diseases/disorders and disorders associated with excessive weight loss, which indicates that inhibitors of Adipsin can be used as a means of said diseases/disorders. Thus the present invention relates to a method of inhibiting (partially or completely) Adipsin biological function in a mammal (e.g., human) comprising administering to the mammal an effective amount of an inhibitor of Adipsin. The invention also relates to a method of enhancing Adipsin biological function in a mammal comprising administering to the mammal an effective amount of an enhancer Adipsin.

Inhibiting Adipsin Expression

Therapeutic compositions according to the present invention may comprise advantageously one or several Adipsin oligonucleotide fragments as an antisense tool or a triple helix tool that inhibits the expression of the corresponding Adipsin gene.

Antisense Approach

In antisense approaches, nucleic acid sequences complementary to an mRNA are hybridized to the mRNA intracellularly, thereby blocking the expression of the protein encoded by the mRNA. The antisense nucleic acid molecules to be used in gene therapy may be either DNA or RNA sequences. Preferred methods using antisense polynucleotide according to the present invention are the procedures described by Sczakiel et al. (1995), which disclosure is hereby incorporated by reference in its entirety.

Preferably, the antisense tools are chosen among the polynucleotides (15–200 bp long) that are complementary to Adipsin mRNA, more preferably to the 5'end of the Adipsin mRNA. In another embodiment, a combination of different antisense polynucleotides complementary to different parts of the desired targeted gene are used.

Other preferred antisense polynucleotides according to the present invention are sequences complementary to either a sequence of Adipsin mRNAs comprising the translation initiation codon ATG or a sequence of Adipsin genomic DNA containing a splicing donor or acceptor site.

Preferably, the antisense polynucleotides of the invention have a 3' polyadenylation signal that has been replaced with a self-cleaving ribozyme sequence, such that RNA polymerase II transcripts are produced without poly(A) at their 3' ends, these antisense polynucleotides being incapable of export from the nucleus, such as described by Liu et al.(1994), which disclosure is hereby incorporated by reference in its entirety. In a preferred embodiment, these Adipsin antisense polynucleotides also comprise, within the ribozyme cassette, a histone stem-loop structure to stabilize cleaved transcripts against 3'-5' exonucleolytic degradation, such as the structure described by Eckner et al.(1991), which disclosure is hereby incorporated by reference in its entirety.

The antisense nucleic acids should have a length and melting temperature sufficient to permit formation of an intracellular duplex having sufficient stability to inhibit the expression of the Adipsin mRNA in the duplex. Strategies for designing antisense nucleic acids suitable for use in gene therapy are disclosed in Green et al., (1986) and Izant and Weintraub, (1984), the disclosures of which are incorporated herein by reference.

In some strategies, antisense molecules are obtained by reversing the orientation of the Adipsin coding region with respect to a promoter so as to transcribe the opposite strand from that which is normally transcribed in the cell. The antisense molecules may be transcribed using in vitro transcription systems such as those which employ T7 or SP6 polymerase to generate the transcript. Another approach involves transcription of Adipsin antisense nucleic acids in vivo by operably linking DNA containing the antisense sequence to a promoter in a suitable expression vector.

Alternatively, oligonucleotides that are complementary to the strand normally transcribed in the cell may be synthesized in vitro. Thus, the antisense nucleic acids are complementary to the corresponding mRNA and are capable of hybridizing to the mRNA to create a duplex. In some embodiments, the antisense sequences may contain modified sugar phosphate backbones to increase stability and make them less sensitive to RNase activity. Examples of modifications suitable for use in antisense strategies include 2'

O-methyl RNA oligonucleotides and Protein-nucleic acid (PNA) oligonucleotides. Further examples are described by Rossi et al., (1991), which disclosure is hereby incorporated by reference in its entirety.

Various types of antisense oligonucleotides complementary to the sequence of the Adipsin cDNA or genomic DNA may be used. In one preferred embodiment, stable and semi-stable antisense oligonucleotides described in International Application No. PCT WO94/23026, hereby incorporated by reference, are used. In these molecules, the 3' end or both the 3' and 5' ends are engaged in intramolecular hydrogen bonding between complementary base pairs. These molecules are better able to withstand exonuclease attacks and exhibit increased stability compared to conventional antisense oligonucleotides.

In another preferred embodiment, the antisense oligodeoxynucleotides against herpes simplex virus types 1 and 2 described in International Application No. WO 95/04141, hereby incorporated by reference, are used.

In yet another preferred embodiment, the covalently cross-linked antisense oligonucleotides described in International Application No. WO 96/31523, hereby incorporated by reference, are used. These double- or single-stranded oligonucleotides comprise one or more, respectively, inter- or intra-oligonucleotide covalent cross-linkage, wherein the linkage consists of an amide bond between a primary amine group of one strand and a carboxyl group of the other strand or of the same strand, respectively, the primary amine group being directly substituted in the 2' position of the strand nucleotide monosaccharide ring, and the carboxyl group being carried by an aliphatic spacer group substituted on a nucleotide or nucleotide analog of the other strand or the same strand, respectively.

The antisense oligodeoxynucleotides and oligonucleotides disclosed in International Application No. WO 92/18522, incorporated by reference, may also be used. These molecules are stable to degradation and contain at least one transcription control recognition sequence that binds to control proteins and are effective as decoys therefore. These molecules may contain "hairpin" structures, "dumbbell" structures, "modified dumbbell" structures, "cross-linked" decoy structures and "loop" structures.

In another preferred embodiment, the cyclic double-stranded oligonucleotides described in European Patent Application No. 0 572 287 A2, hereby incorporated by reference are used. These ligated oligonucleotide "dumbbells" contain the binding site for a transcription factor and inhibit expression of the gene under control of the transcription factor by sequestering the factor.

Use of the closed antisense oligonucleotides disclosed in International Application No. WO 92/19732, hereby incorporated by reference, is also contemplated. Because these molecules have no free ends, they are more resistant to degradation by exonucleases than are conventional oligonucleotides. These oligonucleotides may be multifunctional, interacting with several regions which are not adjacent to the target mRNA.

The appropriate level of antisense nucleic acids required to inhibit gene expression may be determined using in vitro expression analysis. The antisense molecule may be introduced into the cells by diffusion, injection, infection or transfection using procedures known in the art. For example, the antisense nucleic acids can be introduced into the body as a bare or naked oligonucleotide, oligonucleotide encapsulated in lipid, oligonucleotide sequence encapsidated by viral protein, or as an oligonucleotide operably linked to a promoter contained in an expression vector. The expression vector may be any of a variety of expression vectors known in the art, including retroviral or viral vectors, vectors capable of extrachromosomal replication, or integrating vectors. The vectors may be DNA or RNA.

The antisense molecules are introduced onto cell samples at a number of different concentrations preferably between $1\times10^{-10}$M to $1\times10^{-4}$M. Once the minimum concentration that can adequately control gene expression is identified, the optimized dose is translated into a dosage suitable for use in vivo. For example, an inhibiting concentration in culture of $1\times10^{-7}$ translates into a dose of approximately 0.6 mg/kg bodyweight. Levels of oligonucleotide approaching 100 mg/kg bodyweight or higher may be possible after testing the toxicity of the oligonucleotide in laboratory animals. It is additionally contemplated that cells from the vertebrate are removed, treated with the antisense oligonucleotide, and reintroduced into the vertebrate.

In a preferred application of this invention, the polypeptide encoded by the gene is first identified, so that the effectiveness of antisense inhibition on translation can be monitored using techniques that include but are not limited to antibody-mediated tests such as RIAs and ELISA, functional assays, or radiolabeling.

An alternative to the antisense technology that is used according to the present invention comprises using ribozymes that will bind to a target sequence via their complementary polynucleotide tail and that will cleave the corresponding RNA by hydrolyzing its target site (namely "hammerhead ribozymes"). Briefly, the simplified cycle of a hammerhead ribozyme comprises (1) sequence specific binding to the target RNA via complementary antisense sequences; (2) site-specific hydrolysis of the cleavable motif of the target strand; and (3) release of cleavage products, which gives rise to another catalytic cycle. Indeed, the use of long-chain antisense polynucleotide (at least 30 bases long) or ribozymes with long antisense arms are advantageous. A preferred delivery system for antisense ribozyme is achieved by covalently linking these antisense ribozymes to lipophilic groups or to use liposomes as a convenient vector. Preferred antisense ribozymes according to the present invention are prepared as described by Rossi et al, (1991) and Sczakiel et al.(1995), the specific preparation procedures being referred to in said articles being herein incorporated by reference.

Triple Helix Approach

The Adipsin genomic DNA may also be used to inhibit the expression of the Adipsin gene based on intracellular triple helix formation.

Triple helix oligonucleotides are used to inhibit transcription from a genome. They are particularly useful for studying alterations in cell activity when it is associated with a particular gene. The Adipsin cDNA or genomic DNAs of the present invention or, more preferably, a fragment of those sequences, can be used to inhibit gene expression in individuals having diseases associated with expression of a particular gene. Similarly, a portion of the Adipsin genomic DNA can be used to study the effect of inhibiting Adipsin transcription within a cell. Traditionally, homopurine sequences were considered the most useful for triple helix strategies. However, homopyrimidine sequences can also inhibit gene expression. Such homopyrimidine oligonucleotides bind to the major groove at homopurine:homopyrimidine sequences. Thus, both types of sequences from the Adipsin genomic DNA are contemplated within the scope of this invention.

To carry out gene therapy strategies using the triple helix approach, the sequences of the Adipsin genomic DNA are first scanned to identify 10-mer to 20-mer homopyrimidine or homopurine stretches which could be used in triple-helix based strategies for inhibiting Adipsin expression. Following identification of candidate homopyrimidine or homopurine stretches, their efficiency in inhibiting Adipsin expression is assessed by introducing varying amounts of oligonucleotides containing the candidate sequences into tissue culture cells which express the Adipsin gene.

The oligonucleotides can be introduced into the cells using a variety of methods known to those skilled in the art, including but not limited to calcium phosphate precipitation, DEAE-Dextran, electroporation, liposome-mediated transfection or native uptake.

Treated cells are monitored for altered cell function or reduced Adipsin expression using techniques such as Northern blotting, RNase protection assays, or PCR based strategies to monitor the transcription levels of the Adipsin gene in cells which have been treated with the oligonucleotide. The cell functions to be monitored are predicted based upon the homologies of the target gene corresponding to the cDNA from which the oligonucleotide was derived with known gene sequences that have been associated with a particular function. The cell functions can also be predicted based on the presence of abnormal physiology within cells derived from individuals with a particular inherited disease, particularly when the cDNA is associated with the disease.

The oligonucleotides which are effective in inhibiting gene expression in tissue culture cells may then be introduced in vivo using the techniques and at a dosage calculated based on the in vitro results.

In some embodiments, the natural (beta) anomers of the oligonucleotide units can be replaced with alpha anomers to render the oligonucleotide more resistant to nucleases. Further, an intercalating agent such as ethidium bromide, or the like, can be attached to the 3' end of the alpha oligonucleotide to stabilize the triple helix. For information on the generation of oligonucleotides suitable for triple helix formation see Griffin et al.(1989), which is hereby incorporated by this reference.

Treating Adipsin-related Disorders

The present invention further relates to methods of treating diseases/disorders including but not restricted to obesity-related diseases/disorders and disorders associated with excessive weight loss. Obesity-related diseases and disorders include, but are not restricted to, obesity, insulin resistance, atherosclerosis, atheromatous disease, heart disease, hypertension, stroke, Syndrome X, Noninsulin Dependent Diabetes Mellitus (NIDDM, or Type II diabetes) and Insulin Dependent Diabetes Mellitus (IDDM or Type I diabetes). Diabetes-related complications include, but are not restricted to, microangiopathic lesions, ocular lesions, retinopathy, neuropathy, renal lesions. Heart disease includes, but is not limited to, cardiac insufficiency, coronary insufficiency, and high blood pressure. Other obesity-related disorders include, but are not restricted to, hyperlipidemia and hyperuricemia. Disorders associated with excessive weight loss include, but are not restricted to, cachexia, wasting, cancer-related weight loss, AIDS-related weight loss, chronic inflammatory.

Positive controls for methods of screening for compounds that increase Adipsin expression (mRNA or protein) include thiazolidinediones (TZDs) such as troglitazone, pioglitazone, and BRL 49653. These compounds are specifically excluded as test compounds of the methods of screening of the present invention. Likewise, all known compounds currently known to be useful in the treatment of diabetes, insulin resistance, obesity, or another condition or disorder as described herein are specifically excluded from the present invention.

IV. Recombinant Cells of the Invention

Another object of the invention consists of host cells recombinant for, i.e., that have been transformed or transfected with one of the polynucleotides described herein, and more precisely a polynucleotide comprising a polynucleotide encoding a Adipsin polypeptide of the invention such as any one of those described in "Polynucleotides of the Invention". These polynucleotides can be present in cells as a result of transient or stable transfection. The invention includes host cells that are transformed (prokaryotic cells) or that are transfected (eukaryotic cells) with a recombinant vector such as any one of those described in "Recombinant Vectors of the Invention".

Generally, a recombinant host cell of the invention comprises at least one of the polynucleotides or the recombinant vectors of the invention that are described herein.

Preferred host cells used as recipients for the recombinant vectors of the invention are the following:

a) Prokaryotic host cells : *Escherichia coli* strains (I.E. DH5-α strain), *Bacillus subtilis, Salmonella typhimurium*, and strains from species like *Pseudomonas, Streptomyces* and *Staphylococcus*, and b) Eukaryotic host cells : HeLa cells (ATCC N°CCL2; N°CCL2.1; N°CCL2.2), Cv 1 cells (ATCC N°CCL70), COS cells (ATCC N°CRL1650; N°CRL1651), Sf-9 cells (ATCC N°CRL1711), C127 cells (ATCC N° CRL-1804), 3T3 (ATCC N° CRL-6361), CHO (ATCC N° CCL-61), human kidney 293 (ATCC N° 45504; N° CRL-1573), BHK (ECACC N° 84100501; N° 84111301), PLC cells, HepG2, and Hep3B.

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period.

Cells are typically harvested by centrifugation, disrupted by physical or chemical means, and the resulting crude extract retained for further purification.

Microbial cells employed in the expression of proteins can be disrupted by any convenient method, including freeze-thaw cycling, sonication, mechanical disruption, or use of cell lysing agents. Such methods are well known by the skilled artisan.

Further, according to the invention, these recombinant cells can be created in vitro or in vivo in an animal, preferably a mammal, most preferably selected from the group consisting of mice, rats, dogs, pigs, sheep, cattle, and primates, not to include humans. Recombinant cells created in vitro can also be later surgically implanted in an animal, for example. Methods to create recombinant cells in vivo in animals are well-known in the art.

The present invention also encompasses primary, secondary, and immortalized homologously recombinant host cells of vertebrate origin, preferably mammalian origin and particularly human origin, that have been engineered to: a) insert exogenous (heterologous) polynucleotides into the endogenous chromosomal DNA of a targeted gene, b) delete endogenous chromosomal DNA, and/or c) replace endogenous chromosomal DNA with exogenous polynucleotides. Insertions, deletions, and/or replacements of polynucleotide sequences may be to the coding sequences of the targeted gene and/or to regulatory regions, such as promoter and enhancer sequences, operably associated with the targeted gene.

The present invention further relates to a method of making a homologously recombinant host cell in vitro or in vivo, wherein the expression of a targeted gene not normally expressed in the cell is altered. Preferably the alteration causes expression of the targeted gene under normal growth conditions or under conditions suitable for producing the polypeptide encoded by the targeted gene. The method comprises the steps of: (a) transfecting the cell in vitro or in vivo with a polynucleotide construct, the polynucleotide construct comprising; (i) a targeting sequence; (ii) a regulatory sequence and/or a coding sequence; and (iii) an unpaired splice donor site, if necessary, thereby producing a transfected cell; and (b) maintaining the transfected cell in vitro or in vivo under conditions appropriate for homologous recombination.

The present invention further relates to a method of altering the expression of a targeted gene in a cell in vitro or in vivo wherein the gene is not normally expressed in the cell, comprising the steps of: (a) transfecting the cell in vitro or in vivo with a polynucleotide construct, the polynucleotide construct comprising: (i) a targeting sequence; (ii) a regulatory sequence and/or a coding sequence; and (iii) an unpaired splice donor site, if necessary, thereby producing a transfected cell; and (b) maintaining the transfected cell in vitro or in vivo under conditions appropriate for homologous recombination, thereby producing a homologously recombinant cell; and (c) maintaining the homologously recombinant cell in vitro or in vivo under conditions appropriate for expression of the gene.

The present invention further relates to a method of making a polypeptide of the present invention by altering the expression of a targeted endogenous gene in a cell in vitro or in vivo wherein the gene is not normally expressed in the cell, comprising the steps of: a) transfecting the cell in vitro with a polynucleotide construct, the polynucleotide construct comprising: (i) a targeting sequence; (ii) a regulatory sequence and/or a coding sequence; and (iii) an unpaired splice donor site, if necessary, thereby producing a transfected cell; (b) maintaining the transfected cell in vitro or in vivo under conditions appropriate for homologous recombination, thereby producing a homologously recombinant cell; and c) maintaining the homologously recombinant cell in vitro or in vivo under conditions appropriate for expression of the gene thereby making the polypeptide.

The present invention further relates to a polynucleotide construct that alters the expression of a targeted gene in a cell type in which the gene is not normally expressed. This occurs when a polynucleotide construct is inserted into the chromosomal DNA of the target cell, wherein the polynucleotide construct comprises: a) a targeting sequence; b) a regulatory sequence and/or coding sequence; and c) an unpaired splice-donor site, if necessary. Further included are polynucleotide constructs, as described above, wherein the construct further comprises a polynucleotide which encodes a polypeptide and is in-frame with the targeted endogenous gene after homologous recombination with chromosomal DNA.

The compositions may be produced, and methods performed, by techniques known in the art, such as those described in U.S. Pat. Nos. 6,054,288; 6,048,729; 6,048,724; 6,048,524; 5,994,127; 5,968,502; 5,965,125; 5,869,239; 5,817,789; 5,783,385; 5,733,761; 5,641,670; 5,580,734; International Publication Nos: WO96/29411, WO 94/12650; and scientific articles described by Koller et al., (1994) Annu. Rev. Immunol. 10:705–730; the disclosures of each of which are incorporated by reference in their entireties).

The expression of Adipsins in mammalian, and typically human, cells may be rendered defective, or alternatively it may be enhanced, with the insertion of a Adipsin genomic or cDNA sequence with the replacement of the Adipsin gene counterpart in the genome of an animal cell by a Adipsin polynucleotide according to the invention. These genetic alterations may be generated by homologous recombination events using specific DNA constructs that have been previously described.

One kind of host cell that may be used are mammalian zygotes, such as murine zygotes. For example, murine zygotes may undergo microinjection with a purified DNA molecule of interest, for example a purified DNA molecule that has previously been adjusted to a concentration range from 1 ng/ml—for BAC inserts- 3 ng/$\mu$l—for P1 bacteriophage inserts- in 10 mM Tris-HCl, pH 7.4, 250 $\mu$M EDTA containing 100 mM NaCl, 30 $\mu$M spermine, and 70 $\mu$M spermidine. When the DNA to be microinjected has a large size, polyamines and high salt concentrations can be used in order to avoid mechanical breakage of this DNA, as described by Schedl et al ((1993) Nature March 18;362 (6417):258–61).

Any one of the polynucleotides of the invention, including the DNA constructs described herein, may be introduced in an embryonic stem (ES) cell line, preferably a mouse ES cell line. ES cell lines are derived from pluripotent, uncommitted cells of the inner cell mass of pre-implantation blastocysts. Preferred ES cell lines are the following: ES-E14TG2a (ATCC No. CRL-1821), ES-D3 (ATCC No. CRL1934 and No. CRL-11632), YS001 (ATCC No. CRL-11776), 36.5 (ATCC No. CRL-11116). To maintain ES cells in an uncommitted state, they are cultured in the presence of growth inhibited feeder cells which provide the appropriate signals to preserve this embryonic phenotype and serve as a matrix for ES cell adherence. Preferred feeder cells are primary embryonic fibroblasts that are established from tissue of day 13-day 14 embryos of virtually any mouse strain, that are maintained in culture, such as described by Abbondanzo et al. (1993; Methods Enzymol;225:803–23) and are inhibited in growth by irradiation, such as described by Robertson ((1987) Embryo-derived stem cell lines. In: E. J. Robertson Ed. Teratocarcinomas and embrionic stem cells: a practical approach. IRL Press, Oxford), or by the presence of an inhibitory concentration of LIF, such as described by Pease and Williams (1990; Exp Cell Res. October;190(2):209–11).

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period. Cells are typically harvested by centrifugation, disrupted by physical or chemical means, and the resulting crude extract retained for further purification. Microbial cells employed in the expression of proteins can be disrupted by any convenient method, including freeze-thaw cycling, sonication, mechanical disruption, or use of cell lysing agents. Such methods are well known by the skilled artisan.

III. Transgenic Animals

The present invention also provides methods and compositions for the generation of non-human animals and plants that express the recombinant Adipsin polypeptides, of the present invention. The animals or plants can be transgenic, i.e. each of their cells contains a gene encoding a Adipsin polypeptide, or, alternatively, a polynucleotide encoding a Adipsin polypeptide can be introduced into somatic cells of the animal or plant, e.g. into mammary secretory epithelial cells of a mammal. In preferred embodiments, the non-human animal is a mammal such as a cow, sheep, goat, pig, or rabbit.

Methods of making transgenic animals such as mammals are well known to those of skill in the art, and any such method can be used in the present invention. Briefly, transgenic mammals can be produced, e.g., by transfecting a pluripotential stem cell such as an ES cell with a polynucleotide encoding a polypeptide of interest. Successfully transformed ES cells can then be introduced into an early stage embryo which is then implanted into the uterus of a mammal of the same species. In certain cases, the transformed ("transgenic") cells will comprise part of the germ line of the resulting animal, and adult animals comprising the transgenic cells in the germ line can then be mated to other animals, thereby eventually producing a population of transgenic animals that have the transgene in each of their cells, and which can stably transmit the transgene to each of their offspring. Other methods of introducing the polynucleotide can be used, for example introducing the polynucleotide encoding the polypeptide of interest into a fertilized egg or early stage embryo via microinjection. Alternatively, the transgene may be introduced into an animal by infection of zygotes with a retrovirus containing the transgene (Jaenisch, R. (1976) Proc. Natl. Acad. Sci. USA 73, 1260–1264). Methods of making transgenic mammals are described, e.g., in Wall et al. (1992) J Cell Biochem 1992 June;49(2): 113–20; Hogan, et al. (1986) in Manipulating the mouse embryo. A Laboratory Manual. Cold Spring Harbor Laboratory Press, Cold Spring Harbor, N.Y.; in WO 91/08216, or in U.S. Pat. No. 4,736,866.

In a preferred method, the polynucleotides are microinjected into the fertilized oocyte. Typically, fertilized oocytes are microinjected using standard techniques, and then cultured in vitrountil a "pre-implantation embryo" is obtained. Such pre-implantation embryos preferably contain approximately 16 to 150 cells. Methods for culturing fertilized oocytes to the pre-implantation stage are described, e.g., by Gordon et al. ((1984) Methods in Enzymology, 101, 414); Hogan et al. ((1986) in Manipulating the mouse embryo. A Laboratory Manual. Cold Spring Harbor Laboratory Press, Cold Spring Harbor, N.Y.) (for the mouse embryo); Hammer et al. ((1985) Nature, 315, 680) (for rabbit and porcine embryos); Gandolfi et al. ((1987) J. Reprod. Fert. 81, 23–28); Rexroad et al. ((1988) J. Anim. Sci. 66, 947–953) (for ovine embryos); and Eyestone et al. ((1989) J. Reprod. Fert. 85, 715–720); Camous et al. ((1984) J. Reprod. Fert. 72, 779–785); and Heyman et al. ((1987) Theriogenology 27, 5968) (for bovine embryos); the disclosures of each of which are incorporated herein in their entireties. Pre-implantation embryos are then transferred to an appropriate female by standard methods to permit the birth of a transgenic or chimeric animal, depending upon the stage of development when the transgene is introduced.

As the frequency of transgene incorporation is often low, the detection of transgene integration in pre-implantation embryos is often desirable using any of the herein-described methods. Any of a number of methods can be used to detect the presence of a transgene in a pre-implantation embryo. For example, one or more cells may be removed from the pre-implantation embryo, and the presence or absence of the transgene in the removed cell or cells can be detected using any standard method e.g. PCR. Alternatively, the presence of a transgene can be detected in utero or post partum using standard methods.

In a particularly preferred embodiment of the present invention, transgenic mammals are generated that secrete recombinant Adipsin polypeptides in their milk. As the mammary gland is a highly efficient protein-producing organ, such methods can be used to produce protein concentrations in the gram per liter range, and often significantly more. Preferably, expression in the mammary gland is accomplished by operably linking the polynucleotide encoding the Adipsin polypeptide to a mammary gland specific promoter and, optionally, other regulatory elements. Suitable promoters and other elements include, but are not limited to, those derived from mammalian short and long WAP, alpha, beta, and kappa, casein, alpha and beta lactoglobulin, beta-CN 5' genes, as well as the the mouse mammary tumor virus (MMTV) promoter. Such promoters and other elements may be derived from any mammal, including, but not limited to, cows, goats, sheep, pigs, mice, rabbits, and guinea pigs. Promoter and other regulatory sequences, vectors, and other relevant teachings are provided, e.g., by Clark (1998) J Mammary Gland Biol Neoplasia 3:337–50; Jost et al. (1999) Nat. Biotechnol 17:160–4; U.S. Pat. Nos. 5,994,616; 6,140,552; 6,013,857; Sohn et al. (1999) DNA Cell Biol. 18:845–52; Kim et al. (1999) J. Biochem. (Japan) 126:320–5; Soulier et al. (1999) Euro. J. Biochem. 260:533–9; Zhang et al. (1997) Chin. J. Biotech. 13:271–6; Rijnkels et al. (1998) Transgen. Res. 7:5–14; Korhonen et al. (1997) Euro. J. Biochem. 245:482–9; Uusi-Oukari et al. (1997) Transgen. Res. 6:75–84; Hitchin et al. (1996) Prot. Expr. Purif. 7:247–52; Platenburg et al. (1994) Transgen. Res. 3:99–108; Heng-Cherl et al. (1993) Animal Biotech. 4:89–107; and Christa et al. (2000) Euro. J. Biochem. 267:1665–71; the entire disclosures of each of which is herein incorporated by reference.

In another embodiment, the polypeptides of the invention can be produced in milk by introducing polynucleotides encoding the polypeptides into somatic cells of the mammary gland in vivo, e.g. mammary secreting epithelial cells. For example, plasmid DNA can be infused through the nipple canal, e.g. in association with DEAE-dextran (see, e.g., Hens et al. (2000) Biochim. Biophys. Acta 1523:161–171), in association with a ligand that can lead to receptor-mediated endocytosis of the construct (see, e.g., Sobolev et al. (1998) 273:7928–33), or in a viral vector such as a retroviral vector, e.g. the Gibbon ape leukemia virus (see, e.g., Archer et al. (1994) PNAS 91:6840–6844). In any of these embodiments, the polynucleotide may be operably linked to a mammary gland specific promoter, as described above, or, alternatively, any strongly expressing promoter such as CMV or MoMLV LTR.

The suitability of any vector, promoter, regulatory element, etc. for use in the present invention can be assessed beforehand by transfecting cells such as mammary epithelial cells, e.g. MacT cells (bovine mammary epithelial cells) or GME cells (goat mammary epithelial cells), in vitro and assessing the efficiency of transfection and expression of the transgene in the cells.

For in vivo administration, the polynucleotides can be administered in any suitable formulation, at any of a range of concentrations (e.g. 1–500 µg/ml, preferably 50–100 µg/ml), at any volume (e.g. 1–100 ml, preferably 1 to 20 ml), and can be administered any number of times (e.g. 1, 2, 3, 5, or 10 times), at any frequency (e.g. every 1, 2, 3, 5, 10, or any number of days). Suitable concentrations, frequencies, modes of administration, etc. will depend upon the particular polynucleotide, vector, animal, etc., and can readily be determined by one of skill in the art.

In a preferred embodiment, a retroviral vector such as as Gibbon ape leukemia viral vector is used, as described in Archer et al. ((1994) PNAS 91:6840–6844). As retroviral infection typically requires cell division, cell division in the mammary glands can be stimulated in conjunction with the administration of the vector, e.g. using a factor such as estrodiol benzoate, progesterone, reserpine, or dexamethasone. Further, retroviral and other methods of infection can be facilitated using accessory compounds such as polybrene.

In any of the herein-described methods for obtaining Adipsin polypeptides from milk, the quantity of milk obtained, and thus the quantity of Adipsin polypeptides produced, can be enhanced using any standard method of lactation induction, e.g. using hexestrol, estrogen, and/or progesterone.

The polynucleotides used in such embodiments can either encode a full-length Adipsin polypeptide or an Adipsin fragment. Typically, the encoded polypeptide will include a signal sequence to ensure the secretion of the protein into the milk. Where a full length Adipsin sequence is used, the full length protein can, e.g., be isolated from milk and cleaved in vitro using a suitable protease. Alternatively, a second, protease-encoding polynucleotide can be introduced into the animal or into the mammary gland cells, whereby expression of the protease results in the cleavage of the Adipsin polypeptide in vivo, thereby allowing the direct isolation of Adipsin fragments from milk.

IV. Pharmaceutical or Physiologically Acceptable Compositions of the Invention The Adipsin polypeptides of the invention can be administered to non-human animals and/or humans, alone or in pharmaceutical or physiologically acceptable compositions where they are mixed with suitable carriers or excipient(s). The pharmaceutical or physiologically acceptable composition is then provided at a therapeutically effective dose. A therapeutically effective dose refers to that amount of a Adipsin polypeptide sufficient to result in prevention or amelioration of symptoms or physiological status of metabolic-related diseases or disorders as determined by the methods described herein. A therapeutically effective dose can also refer to the amount of a Adipsin polypeptide necessary for a reduction in weight or a prevention of an increase in weight or prevention of an increase in the rate of weight gain in persons desiring this affect for cosmetic reasons. A therapeutically effective dosage of a Adipsin polypeptide of the invention is that dosage that is adequate to promote weight loss or weight gain with continued periodic use or administration. Techniques for formulation and administration of Adipsin polypeptides may be found in "Remington's Pharmaceutical Sciences," Mack Publishing Co., Easton, Pa., latest edition.

Other diseases or disorders that GMP-1 polypeptides of the invention could be used to treat or prevent include, but are not limited to, obesity and obesity-related diseases and disorders such as obesity, insulin resistance, atherosclerosis, atheromatous disease, heart disease, hypertension, stroke, Syndrome X, Noninsulin Dependent Diabetes Mellitus (NIDDM, or Type II diabetes) and insulin Dependent Diabetes Mellitus (IDDM or Type I diabetes). Diabetes-related complications to be treated by the methods of the invention include microangiopathic lesions, ocular lesions, retinopathy, neuropathy, renal lesions. Heart disease includes, but is not limited to, cardiac insufficiency, coronary insufficiency, and high blood pressure. Other obesity-related disorders to be treated by compounds of the invention include hyperlipidemia and hyperuricemia. Yet other obesity-related diseases or disorders of the invention include cachexia, wasting, AIDS-related weight loss, anorexia, and bulimia. The GMP-1 polypeptides may also be used to enhance physical performance during work or exercise or enhance a feeling of general well-being. Physical performance activities include walking, running, jumping, lifting and/or climbing.

The Adipsin polypeptides or antagonists thereof may also be used to treat dyslexia, attention-deficit disorder (ADD), attention-deficit/hyperactivity disorder (ADHD), and psychiatric disorders such as schizophrenia by modulating fatty acid metabolism, more specifically, the production of certain long-chain polyunsaturated fatty acids.

It is expressly considered that the Adipsin polypeptides of the invention may be provided alone or in combination with other pharmaceutically or physiologically acceptable compounds. Other compounds useful for the treatment of obesity and other diseases and disorders are currently well-known in the art.

In a preferred embodiment, the Adipsin polypeptides are useful for, and used in, the treatment of insulin resistance and diabetes using methods described herein and known in the art. More particularly, a preferred embodiments relates to process for the therapeutic modification and regulation of glucose metabolism in an animal or human subject, which comprises administering to a subject in need of treatment (alternatively on a timed daily basis) Adipsin polypeptide (or polynucleotide encoding said polypeptide) in dosage amount and for a period sufficient to reduce plasma glucose levels in said animal or human subject.

Further preferred embodiments relate to methods for the prophylaxis or treatment of diabetes comprising administering to a subject in need of treatment (alternatively on a timed daily basis) a Adipsin polypeptide (or polynucleotide encoding said polypeptide) in dosage amount and for a period sufficient to reduce plasma glucose levels in said animal or human subject.

Routes of Administration.

Suitable routes of administration include oral, nasal, rectal, transmucosal, or intestinal administration, parenteral delivery, including intramuscular, subcutaneous, intramedullary injections, as well as intrathecal, direct intraventricular, intravenous, intraperitoneal, intranasal, intrapulmonary (inhaled) or intraocular injections using methods known in the art. A particularly useful method of administering compounds for promoting weight loss involves surgical implantation, for example into the abdominal cavity of the recipient, of a device for delivering Adipsin polypeptides over an extended period of time. Other particularly preferred routes of administration are aerosol and depot formulation. Sustained release formulations, particularly depot, of the invented medicaments are expressly contemplated.

Composition/Formulation

Pharmaceutical or physiologically acceptable compositions and medicaments for use in accordance with the present invention may be formulated in a conventional manner using one or more physiologically acceptable carriers comprising excipients and auxiliaries. Proper formulation is dependent upon the route of administration chosen.

Certain of the medicaments described herein will include a pharmaceutically or physiologically acceptable acceptable carrier and at least one polypeptide that is a Adipsin polypeptide of the invention. For injection, the agents of the invention may be formulated in aqueous solutions, preferably in physiologically compatible buffers such as Hanks's solution, Ringer's solution, or physiological saline buffer such as a phosphate or bicarbonate buffer. For transmucosal administration, penetrants appropriate to the barrier to be permeated are used in the formulation. Such penetrants are generally known in the art.

Pharmaceutical or physiologically acceptable preparations that can be taken orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable gaseous propellant, e.g., carbon dioxide. In the case of a pressurized aerosol the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in aqueous vehicles, and may contain formulatory agents such as suspending, stabilizing and/or dispersing agents.

Pharmaceutical or physiologically acceptable formulations for parenteral administration include aqueous solutions of the active compounds in water-soluble form. Aqueous suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder or lyophilized form for constitution with a suitable vehicle, such as sterile pyrogen-free water, before use.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Additionally, the compounds may be delivered using a sustained-release system, such as semipermeable matrices of solid hydrophobic polymers containing the therapeutic agent. Various sustained release materials have been established and are well known by those skilled in the art. Sustained-release capsules may, depending on their chemical nature, release the compounds for a few weeks up to over 100 days.

Depending on the chemical nature and the biological stability of the therapeutic reagent, additional strategies for protein stabilization may be employed.

The pharmaceutical or physiologically acceptable compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Effective Dosage.

Pharmaceutical or physiologically acceptable compositions suitable for use in the present invention include compositions wherein the active ingredients are contained in an effective amount to achieve their intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes or encompasses a concentration point or range shown to increase leptin or lipoprotein uptake or binding in an in vitro system. Such information can be used to more accurately determine useful doses in humans.

A therapeutically effective dose refers to that amount of the compound that results in amelioration of symptoms in a patient. Toxicity and therapeutic efficacy of such compounds can be determined by standard pharmaceutical procedures m cell cultures or experimental animals, e.g., for determining the LD50, (the dose lethal to 50% of the test population) and the ED50 (the dose therapeutically effective in 50% of the population). The dose ratio between toxic and therapeutic effects is the therapeutic index and it can be expressed as the ratio between LD5O and ED5O. Compounds that exhibit high therapeutic indices are preferred.

The data obtained from these cell culture assays and animal studies can be used in formulating a range of dosage for use in humans. The dosage of such compounds lies preferably within a range of circulating concentrations that include the ED50, with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, in "The Pharmacological Basis of Therapeutics", Ch. 1).

Dosage amount and interval may be adjusted individually to provide plasma levels of the active compound which are sufficient to maintain or prevent weight loss or gain, depending on the particular situation. Dosages necessary to achieve these effects will depend on individual characteristics and route of administration.

Dosage intervals can also be determined using the value for the minimum effective concentration. Compounds should be administered using a regimen that maintains plasma levels above the minimum effective concentration for 10–90% of the time, preferably between 30–90%; and most preferably between 50–90%. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

A preferred dosage range for the amount of a Adipsin polypeptide of the invention, which can be administered on a daily or regular basis to achieve desired results, including a reduction in levels of circulating plasma triglyceride-rich lipoproteins, range from 0.05–1.0 mg/kg body mass. A more preferred dosage range is from 0.1–5 mg/kg. A more preferred dose is 0.25–2.5 mg/kg. Of course, these daily dosages can be delivered or administered in small amounts periodically during the course of a day. It is noted that these dosage ranges are only preferred ranges and are not meant to be limiting to the invention.

V. Methods of Treatment

The invention is drawn inter alia to methods of preventing or treating metabolic-related diseases and disorders comprising providing an individual in need of such treatment with a Adipsin polypeptide of the invention. Preferably, the Adipsin polypeptide has metabolic-related activity either in vitro or in vivo. Preferably the Adipsin polypeptide is provided to the individual in a pharmaceutical composition that is preferably taken orally. Preferably the individual is a mammal, and most preferably a human. In preferred embodiments, the metabolic-related disease or disorder is selected from the group consisting of atherosclerosis, cardiovascular disease, insulin resistance, hypertension, stroke, Syndrome X, Type I diabetes, Type II diabetes and lipoatrophic diabetes. Diabetes-related complications to be treated by the methods of the invention include microangiopathic lesions, ocular lesions, retinopathy, neuropathy and renal lesions. Heart disease includes, but is not limited to, cardiac insufficiency, coronary insufficiency, and high blood pressure. Other metabolic-related disorders to be treated by compounds of the invention include hyperlipidemia, hypertriglyceridemia, and hyperuricemia. Yet other metabolic-related diseases or disorders of the invention include cachexia, wasting, AIDS-related weight loss, neoplasia-related weight loss, anorexia, and bulimia. In preferred embodiments, Adipsin polypeptides in pharmaceutical compositions are used to modulate body weight in healthy individuals for cosmetic reasons.

The invention also features a method of preventing or treating metabolic-related diseases and disorders comprising providing an individual in need of such treatment with a compound identified by assays of the invention (described in Section VI of the Preferred Embodiments of the Invention and in the Examples). Preferably these compounds antagonize or agonize effects of Adipsin polypeptides in cells in vitro, muscles ex vivo, or in animal models. Alternatively, these compounds agonize or antagonize the effects of Adipsin polypeptides on leptin and/or lipoprotein uptake and/or binding. Optionally, these compounds prevent the interaction, binding, or uptake of Adipsin polypeptides with LSR in vitro or in vivo. Preferably, the compound is provided to the individual in a pharmaceutical composition that is preferably taken orally. Preferably the individual is a mammal, and most preferably a human. In preferred embodiments, the metabolic-related disease or disorder is selected from the group consisting of obesity and metabolic-related diseases and disorders such as atherosclerosis, heart disease, insulin resistance, hypertension, stroke, Syndrome X, Type I diabetes, Type II diabetes, and lipoatrophic diabetes. Diabetes-related complications to be treated by the methods of the invention include microangiopathic lesions, ocular lesions, retinopathy, neuropathy and renal lesions. Heart disease includes, but is not limited to, cardiac insufficiency, coronary insufficiency, and high blood pressure. Other metabolic-related disorders to be treated by compounds of the invention include hyperlipidemia, hypertriglyceridemia, and hyperuricemia.

In further preferred embodiments, the present invention of said pharmaceutical or physiologically acceptable composition can be used as a method to control blood glucose in some individuals, particularly those with Type I diabetes, Type II diabetes, or insulin resistance, in combination with insulin therapy.

In further preferred embodiments, the present invention of said pharmaceutical or physiologically acceptable composition can be used as a method to control body weight in some individuals, particularly those with Type I diabetes, Type II diabetes, or insulin resistance, in combination with insulin therapy.

In further preferred embodiments, the present invention of said pharmaceutical or physiologically acceptable composition can be used as a method to control blood glucose in some individuals, particularly those with Type I diabetes, Type II diabetes, or insulin resistance, alone, without combination of insulin therapy.

In further preferred embodiments, the present invention of said pharmaceutical or physiologically acceptable composition can be used as a method to control body weight in some individuals, particularly those with Type II diabetes or insulin resistance, alone, without combination of insulin therapy. In still a further preferred embodiment, the control of body weight is due in part or in whole to a decrease in mass of 1)subcutaneous adipose tissue and/or 2)viseral (omental) adipose tissue.

In a further preferred embodiment, the present invention may be used in complementary therapy, particularly in some individuals, particularly those with Type I diabetes, Type II diabetes, or insulin resistance, to improve their weight or glucose control in combination with an insulin secretagogue or an insulin sensitising agent. Preferably, the insulin secretagogue is 1,1-dimethyl-2-(2-morpholino phenyl)guanidine fumarate (BTS67582) or a sulphonylurea selected from tolbutamide, tolazamide, chlorpropamide, glibenclamide, glimepiride, glipizide and glidazide. Preferably, the insulin sensitising agent is selected from metformin, ciglitazone, troglitazone and pioglitazone.

The present invention further provides a method of improving the body weight or glucose control of some individuals, particularly those with Type I diabetes, Type II diabetes, or insulin resistance,alone, without an insulin secretagogue or an insulin sensitising agent.

In a further preferred embodiment, the present invention may be administered either concomitantly or concurrently, with the insulin secretagogue or insulin sensitising agent for example in the form of separate dosage units to be used simultaneously, separately or sequentially (either before or after the secretagogue or either before or after the sensitising agent). Accordingly, the present invention further provides for a composition of pharmaceutical or physiologically acceptable composition and an oral insulin secretagogue or insulin sensitising agent as a combined preparation for simultaneous, separate or sequential use for the improvement of body weight or glucose control in some individuals, particularly those with Type I diabetes, Type II diabetes, or insulin resistance.

In further preferred embodiments, the present invention of said pharmaceutical or physiologically acceptable composition further provides a method for the use as an insulin sensitiser.

In further preferred embodiments, the present invention of said pharmaceutical or physiologically acceptable composition can be used as a method to improve insulin sensitivity in some individuals, particularly those with Type I diabetes, Type II diabetes, or insulin resistance, in combination with insulin therapy.

In further preferred embodiments, the present invention of said pharmaceutical or physiologically acceptable composition can be used as a method to improve insulin sensitivity in some individuals, particularly those with Type II diabetes or insulin resistance, without insulin therapy.

VI. Assays for Identifying Modulators of Adipsin Polypeptide Activity

The invention features methods of screening for one or more compounds that modulate the activity of Adipsin in cells, which includes providing potential compounds to be tested to the cells. Exemplary assays that may be used are described in the Examples section. To these assays would be added compounds to be tested for their inhibitory or stimulatory activity as compared to the effects of Adipsin polypeptides alone. Other assays in which an effect is observed based on the addition of Adipsin polypeptides can also be used to screen for modulators of Adipsin polypeptide activity or effects of the presence of Adipsin polypeptides on cells. The essential step is to apply an unknown compound and then to monitor an assay for a change from what is seen when only Adipsin polypeptides are applied to the cell. A change is defined as something that is significantly different in the presence of the compound plus Adipsin polypeptide compared to Adipsin polypeptide alone. In this case, significantly different would be an "increase" or a "decrease" in a measurable effect of at least 25%, 30%, 35%, 40%, 45%, 50%, 55%, 60%, 65%, 70%, or 75%.

The term "modulation" as used herein refers to a measurable change in an activity. Examples include, but are not limited to, lipolysis stimulated receptor (LSR) modulation, leptin modulation, lipoprotein modulation, plasma FFA levels, FFA oxidation, TG levels, glucose levels, and weight. These effects can be in vitro or preferably in vivo. Modulation of an activity can be either an increase or a decrease in the activity. Thus, LSR activity can be increased or decreased, leptin activity can be increased or decreased, and lipoprotein activity can be increased or decreased. Similarly, FFA, TG, glucose levels and weight can be increased or decreased in vivo Free Fatty Acid oxidation can be increased or decreased in vivo or ex vivo.

By "LSR" activity is meant expression of LSR on the surface of the cell, or in a particular conformation, as well as its ability to bind, uptake, and degrade leptin and lipoprotein. By "leptin" activity is meant its binding, uptake and degradation by LSR, as well as its transport across a blood brain barrier, and potentially these occurrences where LSR is not necessarily the mediating factor or the only mediating factor. Similarly, by "lipoprotein" activity is meant its binding, uptake and degradation by LSR, as well as these occurrences where LSR is not necessarily the mediating factor or the only mediating factor. Exemplary assays are provided in the Examples. These assay and other comparable assays can be used to determine/identify compounds that modulate Adipsin polypeptide activity. In some cases it may be important to identify compounds that modulate some but not all of the Adipsin polypeptide activities, although preferably all activities are modified.

The term "increasing" as used herein refers to the ability of a compound to increase the activity of Adipsin polypeptides in some measurable way compared to the effect of Adipsin polypeptides in its absence. As a result of the presence of the compound leptin binding and/or uptake might increase, for example, as compared to controls in the presence of the Adipsin polypeptide alone. Preferably, an increase in activity is at least 25%, 30%, 35%, 40%, 45%, 50%, 55%, 60%, 65%, 70%, or 75% compared to the level of activity in the presence of the Adipsin polypeptide.

Similarly, the term "decreasing" as used herein refers to the ability of a compound to decrease an activity in some measurable way compared to the effect of a Adipsin polypeptide in its absence. For example, the presence of the compound decreases the plasma concentrations of FFA, TG, and glucose in mice. Also as a result of the presence of a compound leptin binding and/or uptake might decrease, for example, as compared to controls in the presence of the Adipsin polypeptide alone. Preferably, a decrease in activity is at least 25%, 30%, 35%, 40%, 45%, 50%, 55%, 60%, 65%, 70%, or 75% as compared to the level of activity in the presence of the Adipsin polypeptide alone.

The invention features a method for identifying a potential compound to decrease body mass in individuals in need of decreasing body mass comprising: a) contacting a cell with a Adipsin polypeptide and a candidate compound; b) detecting a result selected from the group consisting of LSR modulation, leptin modulation, increase in glucose uptake or oxidation, decrease in blood lipid or triglyceride levels, increase in lipoprotein binding, uptake or degradation; FFA oxidation increase; and c) wherein said result identifies said potential compound if said result differs from said result when said cell is contacted with the Adipsin polypeptide alone.

Alternatively, the invention features a method for identifying a potential compound to increase body mass in individuals in need of increasing body mass comprising: a) contacting a cell with a Adipsin polypeptide and a candidate compound; b) detecting a result selected from the group consisting of LSR modulation, leptin modulation, decrease in glucose uptake or oxidation, increase in blood lipid or triglyceride levels, decrease in lipoprotein binding, uptake or degradation; FFA oxidation decrease; and c) wherein said result identifies said potential compound if said result differs from said result when said cell is contacted with the Adipsin polypeptide alone.

In still other preferred embodiments, said potential compound is selected from the group consisting of peptides, peptide libraries, non-peptide libraries, peptoids, fatty acids, lipoproteins, medicaments, antibodies, small molecules, proteases and protease inhibitors.

VIII. Epitopes and Antibody Fusions

A preferred embodiment of the present invention is directed to epitope-bearing polypeptides and epitope-bearing polypeptide fragments. These epitopes may be "antigenic epitopes" or both an "antigenic epitope" and an "immunogenic epitope". An "immunogenic epitope" is defined as a part of a protein that elicits an antibody response in vivo when the polypeptide is the immunogen. On the other hand, a region of polypeptide to which an antibody binds is defined as an "antigenic determinant" or "antigenic epitope." The number of immunogenic epitopes of a protein generally is less than the number of antigenic epitopes. See, e.g., Geysen, et al. (1983) Proc. Natl. Acad. Sci. USA 81:39984002. It is particularly noted that although a particular epitope may not be immunogenic, it is nonetheless useful since antibodies can be made in vitro to any epitope.

An epitope can comprise as few as 3 amino acids in a spatial conformation which is unique to the epitope. Generally an epitope consists of at least 6 such amino acids, and more often at least 8–10 such amino acids. In preferred embodiment, antigenic epitopes comprise a number of amino acids that is any integer between 3 and 50. Fragments which function as epitopes may be produced by any conventional means. See, e.g., Houghten, R. A., Proc. Natl. Acad. Sci. USA 82:5131–5135 (1985), further described in U.S. Pat. No. 4,631,211. Methods for determining the amino acids which make up an immunogenic epitope include x-ray crystallography, 2-dimensional nuclear magnetic resonance, and epitope mapping, e.g., the Pepscan method described by H. Mario Geysen et al. (1984); Proc. Natl. Acad. Sci. U.S.A. 81:3998–4002; PCT Publication No. WO 84/03564; and PCT Publication No. WO 84/03506. Another example is the algorithm of Jameson and Wolf, Comp. Appl. Biosci. 4:181–186 (1988) (said references incorporated by reference in their entireties). The Jameson-Wolf antigenic analysis, for example, may be performed using the computer program PROTEAN, using default parameters (Version 4.0 Windows, DNASTAR, Inc., 1228 South Park Street Madison, Wis.).

The epitope-bearing fragments of the present invention preferably comprises 6 to 50 amino acids (i.e. any integer between 6 and 50, inclusive) of a polypeptide of the present invention. Also, included in the present invention are antigenic fragments between the integers of 6 and the full length sequence of the sequence listing. All combinations of sequences between the integers of 6 and the full-length sequence of a polypeptide of the present invention are included. The epitope-bearing fragments may be specified by either the number of contiguous amino acid residues (as a sub-genus) or by specific N-terminal and C-terminal positions (as species) as described above for the polypeptide fragments of the present invention. Any number of epitope-bearing fragments of the present invention may also be excluded in the same manner.

Antigenic epitopes are useful, for example, to raise antibodies, including monoclonal antibodies that specifically bind the epitope (See, Wilson et al., 1984; and Sutcliffe, J. G. et al., 1983). The antibodies are then used in various techniques such as diagnostic and tissue/cell identification techniques, as described herein, and in purification methods.

Similarly, immunogenic epitopes can be used to induce antibodies according to methods well known in the art (See, Sutcliffe et al., supra; Wilson et al., supra; Chow, M. et al.;(1985) and Bittle, F. J. et al., (1985). A preferred immunogenic epitope includes the polypeptides of the sequence listing. The immunogenic epitopes may be presented together with a carrier protein, such as an albumin, to an animal system (such as rabbit or mouse) if necessary. Immunogenic epitopes comprising as few as 8 to 10 amino acids have been shown to be sufficient to raise antibodies capable of binding to, at the very least, linear epitopes in a denatured polypeptide (e.g., in Western blotting.).

Epitope-bearing polypeptides of the present invention are used to induce antibodies according to methods well known in the art including, but not limited to, in vivo immunization, in vitro immunization, and phage display methods (See, e.g., Sutcliffe, et al., supra; Wilson, et al., supra, and Bittle, et al., 1985). If in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine residues may be coupled to a carrier using a linker such as -maleimidobenzoyl-N-hydroxysuccinimide ester (MBS), while other peptides may be coupled to carriers using a more general linking agent such as glutaraldehyde. Animals such as rabbits, rats and mince are immunized with either free or carrier-coupled peptides, for instance, by intraperitoneal and/or intradermal injection of emulsions containing about 100 µgs of peptide or carrier protein and Freund's adjuvant. Several booster injections may be needed, for instance, at intervals of about two weeks, to provide a useful titer of anti-peptide antibody, which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and discussed above, the polypeptides of the present invention including, but not limited to, polypeptides comprising an immunogenic or antigenic epitope can be fused to heterologous polypeptide sequences. For example, the polypeptides of the present invention may be fused with the constant region comprising portions of immunoglobulins (IgA, IgE, IgG, IgM), or portions of the constant region (CH1, CH2, CH3, any combination thereof including both entire domains and portions thereof) resulting in chimeric polypeptides. These fusion proteins facilitate purification, and show an increased half-life in vivo. This has been shown, e.g., for chimeric proteins consisting of the first two domains of the human CD4-polypeptide and various domains of the constant regions of the heavy or light chains of mammalian immunoglobulins (See, e.g., EPA 0,394,827; and Traunecker et al., 1988). Fusion proteins that have a disulfide-linked dimeric structure due to the IgG portion can also be more efficient in binding and neutralizing other molecules than monomeric polypeptides or fragments thereof alone (See, e.g., Fountoulakis et al., 1995). Nucleic acids encoding the above epitopes can also be recombined with a gene of interest as an epitope tag to aid in detection and purification of the expressed polypeptide.

Additional fusion proteins of the invention may be generated through the techniques of gene-shuffling, motif-shuffling, exon-shuffling, or codon-shuffling (collectively referred to as "DNA shuffling"). DNA shuffling may be employed to modulate the activities of polypeptides of the present invention thereby effectively generating agonists and antagonists of the polypeptides. See, for example, U.S. Pat. Nos. 5,605,793; 5,811,238; 5,834,252; 5,837,458; and Patten, P. A., et al., (1997); Harayama, S., (1998); Hansson, L. O., et al (1999); and Lorenzo, M. M. and Blasco, R., (1998). (Each of these documents are hereby incorporated by reference). In one embodiment, one or more components, motifs, sections, parts, domains, fragments, etc., of coding polynucleotides of the invention, or the polypeptides encoded thereby may be recombined with one or more components, motifs, sections, parts, domains, fragments, etc. of one or more heterologous molecules.

Antibodies

The present invention further relates to antibodies and T-cell antigen receptors (TCR), which specifically bind the polypeptides, and more specifically, the epitopes of the polypeptides of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen binding fragments thereof. In a preferred embodiment the antibodies are human antigen binding antibody fragments of the present invention include, but are not limited to, Fab, Fab' F(ab)2 and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes chimeric, humanized, and human monoclonal and polyclonal antibodies, which specifically bind the polypeptides of the present invention. The present invention further includes antibodies that are anti-idiotypic to the antibodies of the present invention.

The antibodies of the present invention may be monospecific, bispecific, and trispecific or have greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, A. et al. (1991); U.S. Pat. Nos. 5,573,920, 4,474,893, 5,601,819, 4,714,681, 4,925,648; Kostelny, S. A. et al. (1992).

Antibodies of the present invention may be described or specified in terms of the epitope(s) or epitope-bearing portion(s) of a polypeptide of the present invention, which are recognized or specifically bound by the antibody. In the case of proteins of the present invention secreted proteins, the antibodies may specifically bind a full-length protein encoded by a nucleic acid of the present invention, a mature protein (i.e., the protein generated by cleavage of the signal peptide) encoded by a nucleic acid of the present invention, a signal peptide encoded by a nucleic acid of the present invention, or any other polypeptide of the present invention. Therefore, the epitope(s) or epitope bearing polypeptide portion(s) may be specified as described herein, e.g., by N-terminal and C-terminal positions, by size in contiguous amino acid residues, or otherwise described herein. Antibodies which specifically bind any epitope or polypeptide of the present invention may also be excluded as individual species. Therefore, the present invention includes antibodies that specifically bind specified polypeptides of the present invention, and allows for the exclusion of the same.

Antibodies of the present invention may also be described or specified in terms of their cross-reactivity. Antibodies that do not specifically bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein, eg., using FASTDB and the parameters set forth herein) to a polypeptide of the present invention are also included in the present invention. Further included in the present invention are antibodies, which only bind polypeptides encoded by polynucleotides, which hybridize to a polynucleotide of the present invention under stringent hybridization conditions (as described herein). Antibodies of the present invention may also be described or specified in terms of their binding affinity. Preferred binding affinities include those with a dissociation constant or Kd value less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples (See, e.g., Harlow et al., 1988).

The antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. The term "monoclonal antibody" is not limited to antibodies produced through hybridoma technology. The term "antibody" refers to a polypeptide or group of polypeptides which are comprised of at least one binding domain, where a binding domain is formed from the folding of variable domains of an antibody molecule to form three-dimensional binding spaces with an internal surface shape and charge distribution complementary to the features of an antigenic determinant of an antigen, which allows an immunological reaction with the antigen. The term "monoclonal antibody" refers to an antibody that is derived from a single clone, including eukaryotic, prokaryotic, or phage clone, and not the method by which it is produced. Monoclonal antibodies can be prepared using a wide variety of techniques known in the art including the use of hybridoma, recombinant, and phage display technology.

Hybridoma techniques include those known in the art (See, e.g., Harlow et al. 1988); Hammerling, et al, 1981). (Said references incorporated by reference in their entireties). Fab and F(ab')2 fragments may be produced, for example, from hybridoma-produced antibodies by proteolytic cleavage, using enzymes such as papain (to produce Fab fragments) or pepsin (to produce F(ab')2 fragments).

Alternatively, antibodies of the present invention can be produced through the application of recombinant DNA technology or through synthetic chemistry using methods known in the art. For example, the antibodies of the present invention can be prepared using various phage display methods known in the art. In phage display methods, functional antibody domains are displayed on the surface of a phage particle, which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al. (1995); Ames, R. S. et al. (1995); Kettleborough, C. A. et al. (1994); Persic, L. et al. (1997); Burton, D. R. et al. (1994); PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743.

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' F(ab)2 and F(ab')2 fragments can also be employed using methods known in the art such as those disclosed in WO 92/22324; Mullinax, R. L. et al. (1992); and Sawai, H. et al. (1995); and Better, M. et al. (1988).

Examples of techniques which can be used to produce single-chain Fvs and antibodies include those described in U.S. Pat. Nos. 4,946,778 and 5,258,498; Huston et al. (1991); Shu, L. et al. (1993); and Skerra, A. et al. (1988). For some uses, including in vivo use of antibodies in humans and in vitro detection assays, it may be preferable to use chimeric, humanized, or human antibodies. Methods for producing chimeric antibodies are known in the art. See e.g., Morrison, (1985); Oi et al., (1986); Gillies, S. D. et al. (1989); and U.S. Pat. No. 5,807,715. Antibodies can be humanized using a variety of techniques including CDR-grafting (EP 0 239 400; WO 91/09967; U.S. Pat. Nos. 5,530,101; and 5,585,089), veneering or resurfacing, (EP 0 592 106; EP 0 519 596; Padlan E. A., 1991; Studnicka G. M. et al., 1994; Roguska M. A. et al., 1994), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; WO 98/46645; WO 98/50433; WO 98/24893; WO 96/34096; WO 96/33735; and WO 91/10741.

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art (See e.g., Harbor et al. supra; WO 93/21232; EP 0 439 095; Naramura, M. et al. 1994; U.S. Pat. No. 5,474,981; Gillies, S. O. et al., 1992; Fell, H. P. et al., 1991).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half-life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al. (1991); Zheng, X. X. et al. (1995); and Vil, H. et al. (1992).

The invention further relates to antibodies that act as agonists or antagonists of the polypeptides of the present invention. For example, the present invention includes antibodies that disrupt the receptor/ligand interactions with the polypeptides of the invention either partially or fully. Included are both receptor-specific antibodies and ligand-specific antibodies. Included are receptor-specific antibodies, which do not prevent ligand binding but prevent receptor activation. Receptor activation (i.e., signaling) may be determined by techniques described herein or otherwise known in the art. Also include are receptor-specific antibodies which both prevent ligand binding and receptor activation. Likewise, included are neutralizing antibodies that bind the ligand and prevent binding of the ligand to the receptor, as well as antibodies that bind the ligand, thereby preventing receptor activation, but do not prevent the ligand from binding the receptor. Further included are antibodies that activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al. (1998); Chen, Z. et al. (1998); Harrop, J. A. et al. (1998); Zhu, Z. et al. (1998); Yoon, D. Y. et al. (1998); Prat, M. et al. (1998) J.; Pitard, V. et al. (1997); Liautard, J. et al. (1997); Carlson, N. G. et al. (1997) J.; Taryman, R. E. et al. (1995); Muller, Y. A. et al. (1998); Bartunek, P. et al. (1996).

As discussed above, antibodies of the polypeptides of the invention can, in turn, be utilized to generate anti-idiotypic antibodies that "mimic" polypeptides of the invention using techniques well known to those skilled in the art (See, e.g. Greenspan and Bona (1989);and Nissinoff (1991). For example, antibodies which bind to and competitively inhibit polypeptide multimerization or binding of a polypeptide of the invention to ligand can be used to generate anti-idiotypes that "mimic" the polypeptide multimerization or binding domain and, as a consequence, bind to and neutralize polypeptide or its ligand. Such neutralization anti-idiotypic antibodies can be used to bind a polypeptide of the invention or to bind its ligands/receptors, and thereby block its biological activity, The invention also concerns a purified or isolated antibody capable of specifically binding to a mutated full length or mature polypeptide of the present invention or to a fragment or variant thereof comprising an epitope of the mutated polypeptide. In another preferred embodiment, the present invention concerns an antibody capable of binding to a polypeptide comprising at least 10 consecutive amino acids of a polypeptide of the present invention and including at least one of the amino acids which can be encoded by the trait causing mutations.

Non-human animals or mammals, whether wild-type or transgenic, which express a different species of a polypeptide of the present invention than the one to which antibody binding is desired, and animals which do not express a polypeptide of the present invention (i.e. a knock out animal) are particularly useful for preparing antibodies. Gene knock out animals will recognize all or most of the exposed regions of a polypeptide of the present invention as foreign antigens, and therefore produce antibodies with a wider array of epitopes. Moreover, smaller polypeptides with only 10 to 30 amino acids may be useful in obtaining specific binding to any one of the polypeptides of the present invention. In addition, the humoral immune system of animals which produce a species of a polypeptide of the present invention that resembles the antigenic sequence will preferentially recognize the differences between the animal's native polypeptide species and the antigen sequence, and produce antibodies to these unique sites in the antigen sequence. Such a technique will be particularly useful in obtaining antibodies that specifically bind to any one of the polypeptides of the present invention.

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

The antibodies of the invention may be labeled by any one of the radioactive, fluorescent or enzymatic labels known in the art.

Consequently, the invention is also directed to a method for detecting specifically the presence of a polypeptide of the present invention according to the invention in a biological sample, said method comprising the following steps:

a) obtaining a biological sample suspected of containing a polypeptide of the present invention;

b) contacting the biological sample with a polyclonal or monoclonal antibody that specifically binds a polypeptide of the present invention under conditions suitable for antigen-antibody binding; and c) detecting the antigen-antibody complex formed.

The invention also concerns a diagnostic kit for detecting in vitro the presence of a polypeptide of the present invention in a biological sample, wherein said kit comprises:

a) a polyclonal or monoclonal antibody that specifically binds a polypeptide of the present invention, optionally labeled;

b) a reagent allowing the detection of the antigen-antibody complexes formed, said reagent carrying optionally a label, or being able to be recognized itself by a labeled reagent, more particularly in the case when the above-mentioned monoclonal or polyclonal antibody is not labeled by itself.

A. Monoclonal Antibody Production by Hybridoma Fusion

Monoclonal antibody to epitopes of any of the peptides identified and isolated as described can be prepared from murine hybridomas according to the classical method of Kohler, G. and Milstein, C., Nature 256:495 (1975) or derivative methods thereof. Briefly, a mouse is repetitively inoculated with a few micrograms of the selected protein or peptides derived therefrom over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as Elisa, as originally described by Engvall, E., Meth. Enzymol. 70:419 (1980), and derivative methods thereof. Selected positive clones can be expanded and their monoclonal antibody product harvested for use. Detailed procedures for monoclonal antibody production are described in Davis, L. et al. Basic Methods in Molecular Biology Elsevier, New York Section 21-2.

B. Polyclonal Antibody Production by Immunization

Polyclonal antiserum containing antibodies to heterogenous epitopes of a single protein can be prepared by immunizing suitable animals with the expressed protein or peptides derived therefrom described above, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. J. Clin. Endocrinol. Metab. 33:988–991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: Handbook of Experimental Immunology D. Wier (ed) Blackwell (1973). Plateau concentration of antibody is usually in the range of 0.1 to 0.2 mg/ml of serum (about 12 $\square$M). Affinity of the antisera for the antigen is determined by preparing competitive binding curves, as described, for example, by Fisher, D., Chap. 42 in: Manual of Clinical Immunology, 2d Ed. (Rose and Friedman, Eds.) Amer. Soc. For Microbiol., Washington, D.C. (1980).

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

Other characteristics and advantages of the invention are described in the Brief Description of the Figures and the Examples. These are meant to be exemplary only, and not to limit the invention in any way. Throughout this application, various publications, patents and published patent applications are cited. The disclosures of these publications, patents and published patent specifications referenced in this application are hereby incorporated by reference into the present disclosure.

EXAMPLES

The following Examples are provided for illustrative purposes and not as a means of limitation. One of ordinary skill in the art would be able to design equivalent assays and methods based on the disclosure herein all of which form part of the instant invention.

Example 1

Effect of Adipsin Polypeptides on Mice Fed a High-Fat Diet

Experiments are performed using approximately 6 week old C57B1/6 mice (8 per group). All mice are housed individually. The mice are maintained on a high fat diet throughout each experiment. The high fat diet (cafeteria diet; D12331 from Research Diets, Inc.) has the following composition: protein kcal % 16, sucrose kcal % 26, and fat kcal % 58. The fat is primarily composed of coconut oil, hydrogenated.

After the mice are fed a high fat diet for 6 days, microosmotic pumps are inserted using isoflurane anesthesia, and are used to provide a Adipsin polypeptide, saline, and an irrelevant inhibitor to the mice subcutaneously (s.c.) for 18 days. Alternatively, Adipsin polypeptide, saline, or an irrelevant inhibitor is injected daily by IP. Body weight is measured on the first, third and fifth day of the high fat diet, and then daily after the start of treatment. Final blood samples are taken by cardiac puncture and are used to determine triglyceride (TG), total cholesterol (TC), free fatty acids (FFA), glucose, leptin, and insulin levels. The amount of food consumed per day is also determined for each group.

Example 2

Tests of Obesity-related Activity in Humans

Tests of the efficacy of Adipsin polypeptides in humans are performed in accordance with a physician's recommendations and with established guidelines. The parameters tested in mice are also tested in humans (e.g. food intake, weight, TG, TC, FFA, glucose, insulin, and leptin). It is expected that the physiological factors (TG, TC, FFA, glucose, insulin, and leptin) show changes over the short term. Changes in weight gain require a longer period of time. In addition, the diet is carefully monitored. Adipsin polypeptides are given in daily doses of about 6 mg protein per 70 kg person or about 10 mg per day. Other doses are also tested, for instance, 0.1 mg, 1 mg or 5 mg per day up to 20 mg, 50 mg, or 100 mg per day.

Example 3

Tests of Obesity-related Activity in a Murine Lipoatrophic Diabetes Model

Previously, leptin is reported to reverse insulin resistance and diabetes mellitus in mice with congenital lipodystrophy (Shimomura et al. Nature 401: 73–76 (1999); hereby incorporated by reference in its entirety). Leptin is found to be less effective in a different lipodystrophic mouse model of lipoatrophic diabetes (Gavrilova et al. Nature 403: 850 (2000); hereby incorporated by reference in its entirety). Weight reduction also reverses insulin resistance, glucose intolerance, as well as dyslipidemias. The instant invention encompasses the use of PIA inhibitors for reducing the insulin resistance and hyperglycaemia in this model either alone or in combination with leptin, the leptin peptide (U.S. provisional application No. 60/155,506), OBG3 (U.S. patent application Ser. No. 09/758,055) or other compounds. Assays included are described previously in Gavrilova et al. ((2000) Diabetes November;49(11):1910–6; (2000) Nature February 24;403(6772):850, which disclosures are hereby incorporated by reference in their entireties) using A-ZIP/F-1 mice, except that compounds of the invention would be administered using the methods previously described in Example 1. The glucose and insulin levels of the mice are tested, and the food intake and liver weight monitored, as well as other factors, such as leptin, FFA, cholesterol and TG levels, typically measured in our experiments (see Example 5).

Example 4

Effect of Adipsin Polypeptides on Plasma Free Fatty Acid in C57 BL/6 Mice

The effect of Adipsin polypeptides on postprandial lipemia (PPL) in normal C57BL6/J mice is tested. The mice are fasted for 2 hours prior to the experiment after which a baseline blood sample is taken. All blood samples are taken from the tail using EDTA coated capillary tubes (50 µL each time point). At time 0 (8:30 AM), a standard high fat meal (6 g butter, 6 g sunflower oil, 10 g nonfat dry milk, 10 g sucrose, 12 mL distilled water prepared fresh following Nb#6, JF, pg.1) is given by gavage (vol.=1% of body weight) to all animals.

Adipsin polypeptide is injected i.p. in 100 µL saline 1) immediately following the high fat meal; 2) 45 min following meal; 3) and at 1 hr 45 min following the meal, 4) or from 24, 16, 12, 8, 6, 4, 2 or 1 hr, or 45, 30 or 15 min. before the meal (treated group, n=8). Control animals (n=8) are injected with saline (3×100 µL). Untreated and treated animals are handled in an alternating mode.

Blood samples are taken in hourly intervals, and are immediately put on ice. Plasma is prepared by centrifugation following each time point. Plasma is kept at −20° C. and free fatty acids (FFA), triglycerides (TG) and glucose are determined within 24 hours using standard test kits (Sigma and Wako). Due to the limited amount of plasma available, glucose can be determined in duplicate using pooled samples (equal volumes of plasma from all animals per treatment group are pooled). Glucose, TG and FFA are determined for each group.

Example 5

Effect of Adipsin Polypeptides on Plasma Leptin and Insulin in C57 BL/6 Mice

The effect of Adipsin polypeptides on plasma leptin and insulin levels during postprandial lipemia (PPL) in normal C57BL6/J mice is tested. The experimental procedure is the same as that described in Example 4, except that blood is drawn only at 0, 2 and 4 hours to allow for greater blood samples needed for the determination of leptin and insulin by RIA.

Briefly, 16 mice are fasted for 2 hours prior to the experiment after which a baseline blood sample is taken. All blood samples are taken from the tail using EDTA coated capillary tubes (100 μL each time point). At time 0 (9:00 AM), a standard high fat meal (see Example 4) is given by gavage (vol.=1% of body weight) to all animals. Adipsin polypeptide is injected i.p. in 100 μL saline 1) immediately following the high fat meal; 2) 45 min following meal; 3) and at 1 hr 45 min following the meal, 4) or from 24, 16, 12, 8, 6, 4, 2 or 1 hr, or 45, 30 or 15 min. before the meal (treated group, n=8). Control animals (n=8) are injected with saline (3×100 μL). Untreated and treated animals are handled in an alternating mode.

Blood samples are immediately put on ice and plasma is prepared by centrifugation following each time point. Plasma is kept at −20° C. and free fatty acids (FFA) are determined within 24 hours using a standard test kit (Wako). Leptin and Insulin are determined by RIA (ML-82K and SRI-13K, LINCO Research, Inc., St. Charles, Mo.) following the manufacturer's protocol. However, only 20 μL plasma is used. Each determination is done in duplicate. Due to the limited amount of plasma available, leptin and insulin can be determined in 4 pools of 2 animals each in both treatment groups.

Example 6

Effect of Adipsin Polypeptides on Plasma FFA, TG and Glucose in C57 BL/6 Mice The experimental procedure is similar to that described in Example 4. Briefly, 18 mice are fasted for 2 hours prior to the experiment after which a baseline blood sample is taken. All blood samples are taken from the tail using EDTA coated capillary tubes (50 μL each time point). At time 0 (9:00 AM), a standard high fat meal (see Example 4) is given by gavage (vol.=1% of body weight) to all animals. In group 1, Adipsin polypeptide is injected i.p. in 100 μL saline 1) immediately following the high fat meal; 2) 45 min following meal; 3) and at 1 hr 45 min following the meal, 4) or from 24, 16, 12, 8, 6, 4, 2 or 1 hr, or 45, 30 or 15 min. before the meal, (treated group, n=8). A group 2 (n=4) received 3 times the amount of inhibitor in group 1 at the same intervals. Control animals (n=6) are injected with saline (3×100 μL). Untreated and treated animals are handled in an alternating mode.

Blood samples are immediately put on ice. Plasma is prepared by centrifugation following each time point. Plasma is kept at −20° C. and free fatty acids (FFA), triglycerides (TG), cholesterol and glucose are determined within 24 hours using standard test kits (Sigma and Wako).

Example 7

Effect of Adipsin Polypeptides on FFA following Epinephrine Injection

In mice, plasma free fatty acids increase after intragastric administration of a high fat/sucrose test meal. These free fatty acids are mostly produced by the activity of lipolytic enzymes i.e. lipoprotein lipase (LPL) and hepatic lipase (HL). In this species, these enzymes are found in significant amounts both bound to endothelium and freely circulating in plasma. Another source of plasma free fatty acids is hormone sensitive lipase (HSL) that releases free fatty acids from adipose tissue after β-adrenergic stimulation. To test whether Adipsin polypeptides also regulate the metabolism of free fatty acid released by HSL, mice are injected with epinephrine.

Two groups of mice (n=5 each) are given epinephrine (5 μg) by intraperitoneal injection. A treated group is injected with Adipsin polypeptide (IP) one hour before and again together with epinephrine, while control animals receive saline. Plasma is isolated and free fatty acids and glucose are measured as described above (Example 6).

In ex vivo experiments, adipose tissue is removed from normal C57BL/6J mice and incubated in Krebs-Henseleit bicarbonate buffer. Epinephrine is added, with or without Adipsin polypeptide and the concentration of FFA in the medium following a 90 min incubation is determined.

Example 8

Effect of Adipsin Polypeptides on Triglyceride in Muscle & Liver Isolated from Mice To determine whether the effect of Adipsin polypeptides increases FFA delivery into muscle or liver, the hindlimb muscle and liver triglyceride content is measured after Adipsin polypeptide treatment of mice. Hindlimb muscles as well as liver samples are removed from treated and untreated animals and the triglyceride and free fatty acid concentration is determined following a standard lipid extraction method Shimabukuro, et al., "Direct antidiabetic effect of leptin through triglyceride depletion of tissues", Proc Natl Acad Sci USA 94, 4637–4641 (1997), which disclosure is hereby incorporated by reference in its entirety, followed by TG and FFA analysis using standard test kits.

Example 9

Longterm Effect of Adipsin Polypeptides on Weight Gain, Weight Loss and other Physiological Factors.

To test the effect of Adipsin polypeptides on weight gain while consuming a high calorie diet, C57BL/6J 10 week old mice are put on a very high fat/sucrose purified diet for 19 days to promote weight gain (see Example 1), and body weight is measured. The mice are then surgically implanted with an osmotic pump (Alzet, Newark, Del.) delivering either Adipsin polypeptides, or physiological saline. Alternately, mice are IP injected daily. The mice are continued on the high fat diet and their body weight and food intake is recorded daily over the following 10-day period. Comparison of the change in weight, food intake, plasma free fatty acids, glucose, cholesterol, insulin and triglycerides is made between groups.

Mice are then continued on a high fat diet or a standard diet without treatment of inhibitors and food intake, body weight, plasma free fatty acids, glucose, cholesterol, insulin and triglycerides are measured weekly for 4 weeks. Comparison of parameters following discontinuation of treatment is made between control mice (no inhibitor treatment) and treated mice (inhibitor discontinued after 10 days). Weight gain per calorie intake is also compared between the groups.

Example 10

Detection of Apm1 Fragment by Immunoprecipitation of Human Plasma after Treatment with Adipsin Polypeptides The effect of Adipsin polypeptides on the plasma levels of Apm1 and fragments thereof is determined following treatment with a Adipsin polypeptide, blood collection and plasma separation. Immunoprecipitation of human plasma Apm1 followed by Western blotting is used to detect a cleavage product of Apm1, the human homolog of Acrp30, using a globular head specific anti-serum for the immunoprecipitation step as well as for the detection step. Preimmune serum or serum raised against the globular head domain or human non-homologous region (HDQETFTQGPGVLLPLPKGA) are cross-linked to protein A (Sigma Chemical CO, Saint Louis, Mo.) using dimethyl-pimelimidate-dihydrochloride (Sigma Chemical Co, Saint Louis, Mo.). After washing (0.2 M salt) proteins are eluted from protein A, separated by SDS-PAGE, transferred to PROTRAN pure nitrocellulose membrane (Schleicher and Schuell, Keene, N.H.) using standard procedures. Apm1 products are visualized using globular head domain antibodies labeled with biotin; horseradish peroxidase conjugated to Streptavidin and CN/DAB substrate kit (Pierce, Rockford, Ill.) according to manufacturer's instructions.

The apparent molecular weight of one species of truncated form is 27 kDa, corresponding to about 70% of the complete form of Apm1.

Example 11

Effect of Adipsin Polypeptides on FFA Following Intralipid Injection

To determine the affect of Adipsin polypeptides on plasma FFA levels, 6 groups of mice (n=5 each) are intravenously (tail vein) injected with 30 μL bolus of Intralipid-20% (Clintec) to generate a sudden rise in plasma FFAs, thus by-passing intestinal absorption. (Intralipid is an intravenous fat emulsion used in nutritional therapy). Treatment groups are injected IP with a Adipsin polypeptide at 30, 60, or 90 minutes before Intralipid is given, while control animals receive saline at the same time intervals. Plasma is isolated and FFAs are measured as described previously (Example 4). Levels of plasma FFA are compared between control and treated groups.

Example 12

Smooth Muscle Growth Inhibitory Effect of Adipsin Polypeptides in the Absence or Presence of Apm1

Methods

A plastic plate is sown with human arterial smooth muscle cells (Clontech) at a concentration of 1×10^4//cm^2 and allowed to stand overnight in DMEM supplemented with 10% FBS, 100IU/ml penicillin, 10 microg/ml streptomycin, and minus or plus 10 microg/ml of Apm1, then incubated in 5% CO2 and 95% air at 37C.

The DNA synthesis into the human arterial smooth muscle cells is quantitated according to [methyl3H]-thymidine uptake (4 replicates).

The cells sown on the 96 well plate are treated with 10 microg/ml of Adipsin polypeptide and/or, as control, 10 ng/ml of HB-EGF in 2% FBS-DMEM for 24 hours. Then [methyl3H]-thymidine is added, 1 microCi/well, over 5 hours. The cells are then treated with trypsin and, using an automatic cell harvester, taken our onto a glass fiber filter. Then, the amount of [methyl3H]-thymidine uptake is directly measured with a beta-counter.

Results:

Comparing the relative ratio of DNA synthesis to control, addition of Adipsin polypeptide, addition of HB-EGF, and addition of Adipsin polypeptide+HG-EGF on the abscissa indicates that Adipsin polypeptide antagonizes the DNA synthesis of human smooth muscle cells. These results would suggest that Adipsin polypeptide is an effective smooth muscle growth inhibitor.

Example 12

The Inhibitory Effect of Adipsin Polypeptides on the Onset of Atherosclerosis in the Absence or Presence of Apm1

Methods

Human aortic vascular endothelial cells (HAEC, purchased from Clontech) sown on a 96-well plate are cultured (5% $CO_2$, 37 C; minus or plus 10 microg/ml of Apm1)) in the vascular endothelial cell culture medium. Using Becton Dickinson's "Biocoat"™, culture is continued until the growth becomes confluent.

Then, recombinant Adipsin polypeptide is added in varying amounts (1, 5, 10, 25 and 50 microg/ml) and the system is further incubated for 18 hours. Thereafter, human recombinant TNF-alpha (10U/ml) is added and the system is further incubated for 6 hours (the Adipsin polypeptide experimental group).

As a control, the group without addition of the recombinant Adipsin polypeptide (i.e., TNF-alpha stimulation only) is provided.

Using the cell-ELISA method, it is analyzed whether Adipsin polypeptide would suppress the expression of adhesion molecule proteins, namely VCAM-1, ELAM and ICAM-1, on the HAEC surface by the above TNF-alpha stimulation. DAKO's 6.5B5 can be used as the anti-ICAM-1 antibody.

The Adipsin polypeptide-added group is compared with the Adipsin polypeptide-free group and the difference is tested for significance. Inhibition of the expression of the major adhesion molecules by Adipsin polypeptide indicates that Adipsin polypeptide prevents the onset of atherosclerosis.

Example 13

Use of Biacore Technology to Detect Specific Binding of a Test Compound to Adipsin Polypeptide Biacore utilizes a biosensor technology for monitoring interactions between two or more molecules in real time, without the use of labels. The molecular classes than can be studied are diverse, ranging from proteins, peptides, nucleic acids, carbohydrates, and lipids to low molecular weight substances and pharmaceuticals.

The detection principle is based on the optical phenomena of surface plasmon resonance, which detects changes in refractive index close to a biosensor surface. In a typical experiment one of the interacting molecules is immobilized or captured (here, Adipsin polypeptide) to a flexible dextran layer close to the sensor surface. In preferred embodiments, said fragment is selected from amino acids 21–253 or 26–253 of SEQ ID NO: 2 where amino acid 21 of SEQ ID NO: 2 is predicted to be the N-terminal amino acid of the mature Adipsin polypeptide absent the putative signal peptide and amino acid 26 of SEQ ID NO: 2 is predicted to be the N-terminal amino acid of the mature Adipsin polypeptide absent both the putative signal peptide and the putative activation peptide, amino acids 20–253 or 26–253 of SEQ ID NO: 4 where amino acid 20 of SEQ ID NO: 4 is predicted to be the N-terminal amino acid of the mature Adipsin polypeptide absent the putative signal peptide and amino acid 26 of SEQ ID NO: 4 is predicted to be the N-terminal amino acid of the mature Adipsin polypeptide absent both the putative signal peptide and the putative activation peptide, or amino acids 1–228 or 2–228 of SEQ ID NO: 6. The interacting partner (here, test compound) is flowed across that surface. If an interaction occurs between the two molecules, there is a resulting increase in signal due to the increase in mass at the chip surface.

Adipsin polypeptide is attached to the sensor surface via amine coupling chemistry. The dextran is activated using N-hydroxysuccinimide and N-ethyl-N'-(3-dimethylaminopropyl)-carbodiimide hydrochloride for 7 minutes. Said Adipsin polypeptide is diluted in 10 mM Na Acetate pH 5.0 at a concentration of 10 µg/ml and injected over the activated surface for 7 minutes. The surface is then blocked for 7 minutes using ethanolamine to remove any remaining esters. A blank flow cell absent said Adipsin polypeptide is set up in parallel and used as a control surface. The running buffer is HBS-EP (0.01M HEPES pH 7.4, 0.15M NaCl, 3 mM EDTA, 0.005% Surfactant P20) and the instrument temperature is 25° C.

The test compound is filtered through an Ultrafree-0.5 Centrifugal Filter Device and resuspended in HBS-EP running buffer. The test compound is then diluted 1:10 in HBS-EP and injected over the said Adipsin polypeptide surface and the blank control surface for 1 minute at a flow rate of 50 µl/min. The sensorgrams from the receptor surface and the control surface are aligned and overlayed.

To obtain the specific binding, the control surface was subtracted from the active surface comprised of said Adipsin polypeptide.

What is claimed is:

1. A method of reducing body mass in an individual comprising administering to said individual a composition comprising a carrier and an Adipsin polypeptide comprising:
   a) amino acids 21–253 or 26–253 of SEQ ID NO: 2 and
      i) the amino acid at position 26 is Met:
      ii) the amino acid at position 52 is Gly;
      iii) the amino acid at position 59 is Gln; or
      iv) the amino acid at position 150 is Leu; or
   b) amino acids 20–253 or 26–253 of SEQ ID NO: 4 and
      i) the amino acid at position 26 is Met;
      ii) the amino acid at position 52 is Gly;
      iii) the amino acid at position 59 is Gln; or
      iv) the amino acid at position 150 is Leu;
   said composition further optionally comprising Apm1 (Adipose Most Abundant Gene Transcript 1) polypeptide.

2. The method according to claim 1, wherein the polypeptide of said composition consists of amino acids 21–253 of SEQ ID NO: 2.

3. The method according to claim 1, wherein the polypeptide of said composition consists of amino acids 26–253 of SEQ ID NO: 2.

4. The method according to claim 1, wherein the polypeptide of said composition consists of amino acids 20–253 of SEQ ID NO: 4.

5. The method according to claim 1, wherein the polypeptide of said composition consists of 26–253 of SEQ ID NO: 4.

6. The method according to claim 1, wherein said composition further comprises Apm1 polypeptide.

7. The method according to claim 2, wherein said composition further comprises Apm1 polypeptide.

8. The method according to claim 3, wherein said composition further comprises Apm1 polypeptide.

9. The method according to claim 4, wherein said composition further comprises Apm1 polypeptide.

10. The method according to claim 5, wherein said composition further comprises Apm1 polypeptide.

11. A method of reducing body mass in an individual comprising administering to said individual a composition comprising a carrier and an Adipsin polypeptide:
   a) comprising amino acids 1–228 of SEQ ID NO: 6;
   b) consisting of amino acids 2–228 of SEQ ID NO: 6; or
   c) comprising amino acids 2–228 of SEQ ID NO: 6, wherein position 27 is glycine, position 34 is arginine, or position 125 is leucine;
   said composition further optionally comprising Apm1 (Adipose Most Abundant Gene Transcript 1) polypeptide.

12. The method according to claim 11, wherein said polypeptide comprises amino acids 1–228 of SEQ ID NO: 6.

13. The method according to claim 12, wherein said composition further comprises Apm1 polypeptide.

14. The method according to claim 11, wherein said polypeptide comprises amino acids 2–228 of SEQ ID NO: 6 and position 27 is glycine.

15. The method according to claim 11, wherein said polypeptide comprises amino acids 2–228 of SEQ ID NO: 6 and position 34 is arginine.

16. The method according to claim 11, wherein said polypeptide comprises amino acids 2–228 of SEQ ID NO: 6 and position 125 is leucine.

17. The method according to claim 14, wherein said composition further comprises Apm1 polypeptide.

18. The method according to claim 15, wherein said composition further comprises Apm1 polypeptide.

19. The method according to claim 16, wherein said composition further comprises Apm1 polypeptide.

20. The method according to claim 11, wherein said polypeptide consists of amino acids 2–228 of SEQ ID NO: 6.

21. The method according to claim 20, wherein said composition further comprises Apm1 polypeptide.

22. A method of reducing body mass in an individual comprising administering to said individual a composition comprising a carrier, Adipsin polypeptide comprising amino acids 2–228 of SEQ ID NO: 6 and Apm1 (Adipose Most Abundant Gene Transcript 1) polypeptide.

23. The method according to claim 1, wherein said Adipsin polypeptide comprises amino acids 21–253 of SEQ ID NO: 2 and the amino acid at position 26 is Met.

24. The method according to claim 1, wherein said Adipsin polypeptide comprises amino acids 21–253 of SEQ ID NO: 2 and the amino acid at position 52 is Gly.

25. The method according to claim 1, wherein said Adipsin polypeptide comprises amino acids 21–253 of SEQ ID NO: 2 and the amino acid at position 59 is Gln.

26. The method according to claim 1, wherein said Adipsin polypeptide comprises amino acids 21–253 of SEQ ID NO: 2 and the amino acid at position 150 is Leu.

27. The method according to claim 1, wherein said Adipsin polypeptide comprises amino acids 26–253 of SEQ ID NO: 2 and the amino acid at position 26 is Met.

28. The method according to claim 1, wherein said Adipsin polypeptide comprises amino acids 26–253 of SEQ ID NO: 2 and the amino acid at position 52 is Gly.

29. The method according to claim 1, wherein said Adipsin polypeptide comprises amino acids 26–253 of SEQ ID NO: 2 and the amino acid at position 59 is Gln.

30. The method according to claim 1, wherein said Adipsin polypeptide comprises amino acids 26–253 of SEQ ID NO: 2 and the amino acid at position 150 is Leu.

31. The method according to claim 1, wherein said Adipsin polypeptide comprises amino acids 21–253 of SEQ ID NO; 4 and the amino acid at position 26 is Met.

32. The method according to claim 1, wherein said Adipsin polypeptide comprises amino acids 21–253 of SEQ ID NO: 4 and the amino acid at position 52 is Gly.

33. The method according to claim 1, wherein said Adipsin polypeptide comprises amino acids 21–253 of SEQ ID NO: 4 and the amino acid at position 59 is Gln.

34. The method according to claim 1, wherein said Adipsin polypeptide comprises amino acids 21–253 of SEQ ID NO: 4 and the amino acid at position 150 is Leu.

35. The method according to claim 1, wherein said Adipsin polypeptide comprises amino acids 26–253 of SEQ ID NO: 4 and the amino acid at position 26 is Met.

36. The method according to claim 1, wherein said Adipsin polypeptide comprises amino acids 26–253 of SEQ ID NO: 4 and the amino acid at position 52 is Gly.

37. The method according to claim 1, wherein said Adipsin polypeptide comprises amino acids 26–253 of SEQ ID NO: 4 and the amino acid at position 59 is Gln.

38. The method according to claim 1, wherein said Adipsin polypeptide comprises amino acids 26–253 of SEQ ID NO: 4 and the amino acid at position 150 is Leu.

39. The method according to claim 23, wherein said composition further comprises Apm1 polypeptide.

40. The method according to claim 24, wherein said composition further comprises Apm1 polypeptide.

41. The method according to claim 25, wherein said composition further comprises Apm1 polypeptide.

42. The method according to claim 26, wherein said composition further comprises Apm1 polypeptide.

43. The method according to claim 27, wherein said composition further comprises Apm1 polypeptide.

44. The method according to claim 28, wherein said composition further comprises Apm1 polypeptide.

45. The method according to claim 29, wherein said composition further comprises Apm1 polypeptide.

46. The method according to claim 30, wherein said composition further comprises Apm1 polypeptide.

47. The method according to claim 31, wherein said composition further comprises Apm1 polypeptide.

48. The method according to claim 32, wherein said composition further comprises Apm1 polypeptide.

49. The method according to claim 33, wherein said composition further comprises Apm1 polypeptide.

50. The method according to claim 34, wherein said composition further comprises Apm1 polypeptide.

51. The method according to claim 35, wherein said composition further comprises Apm1 polypeptide.

52. The method according to claim 36, wherein said composition further comprises Apm1 polypeptide.

53. The method according to claim 37, wherein said composition further comprises Apm1 polypeptide.

54. The method according to claim 38, wherein said composition further comprises Apm1 polypeptide.

* * * * *

UNITED STATES PATENT AND TRADEMARK OFFICE
CERTIFICATE OF CORRECTION

PATENT NO. : 6,867,189 B2
DATED : March 15, 2005
INVENTOR(S) : Kristen Briggs and John M. Lucas It is certified that error appears in the above-identified patent and that said Letters Patent is hereby corrected as shown below:

Column 15,
Line 18, "decreases m waist" should read -- decreases in waist --.

Column 19,
Line 22, "contiguous fill length" should read -- contiguous full length --.

Column 24,
Line 3, "polypeptide mi which" should read -- polypeptide in which --.

Column 28,
Line 64, "vector constricts" should read -- vector constructs --.

Column 30,
Line 28, "lack of antigerticity" should read -- lack of antigenicity --.

Column 43,
Line 60, "2000; http://see Worldwide" should read -- 2000; see Worldwide --.

Column 47,
Line 7, "(Parmeley and Smith" should read -- (Parmley and Smith --.

Column 48,
Line 33, "26 or SEQ" should read -- 26 of SEQ --.

Column 50,
Line 63, "Brain" should read -- Bram --.

Column 59,
Lines 25-26, "cross-linkage" should read -- cross-linkages --.

Column 70,
Line 39, "procedures m" should read -- procedures in --.

UNITED STATES PATENT AND TRADEMARK OFFICE
CERTIFICATE OF CORRECTION

PATENT NO. : 6,867,189 B2
DATED : March 15, 2005
INVENTOR(S) : Kristen Briggs and John M. Lucas It is certified that error appears in the above-identified patent and that said Letters Patent is hereby corrected as shown below:

Column 76,
Line 12, "mince" should read -- mice --.

Signed and Sealed this

Twenty-third Day of August, 2005

JON W. DUDAS
*Director of the United States Patent and Trademark Office*

SEQUENCE LISTING

<160> NUMBER OF SEQ ID NOS: 6

<210> SEQ ID NO 1
<211> LENGTH: 835
<212> TYPE: DNA
<213> ORGANISM: Homo sapiens
<220> FEATURE:
<221> NAME/KEY: CDS
<222> LOCATION: (11)...(772)

<400> SEQUENCE: 1

```
cgatcccacc atg cac agc tcc gtg tac ttc gca gtt ctg gtc ctc cta         49
            Met His Ser Ser Val Tyr Phe Ala Val Leu Val Leu Leu
              1               5                  10 gga gcg gcc gcc tgc gcc gcg cgg ccc cgt ggt cgg atc ctg ggc ggc         97
Gly Ala Ala Ala Cys Ala Ala Arg Pro Arg Gly Arg Ile Leu Gly Gly
     15                  20                  25 aga gag gcc gag gcg cac gct cgg cct tac atg gcg tcg gtg cag ctg        145
Arg Glu Ala Glu Ala His Ala Arg Pro Tyr Met Ala Ser Val Gln Leu
 30                  35                  40                  45 aac ggc gcg cac ctg tgc gca ggc gtc ctg gtg gcg gag cgg tgg gtg        193
Asn Gly Ala His Leu Cys Ala Gly Val Leu Val Ala Glu Arg Trp Val
                 50                  55                  60 ctg agc gcg gcg cac tgc ctg gag gac gcg gcc gac ggg aag gtg cag        241
Leu Ser Ala Ala His Cys Leu Glu Asp Ala Ala Asp Gly Lys Val Gln
             65                  70                  75 gtt ctc ctg ggc gcg cac tcc ctg tcg cag ccg gag ccc tcc aag cgc        289
Val Leu Leu Gly Ala His Ser Leu Ser Gln Pro Glu Pro Ser Lys Arg
         80                  85                  90 ctg tac gac gtg ctc cgc gca gtg ccc cac ccg gac agc cag ccc gac        337
Leu Tyr Asp Val Leu Arg Ala Val Pro His Pro Asp Ser Gln Pro Asp
     95                 100                 105 acc atc gac cac gac ctc ctg cta cag ctg tcg gag aag gcc aca            385
Thr Ile Asp His Asp Leu Leu Leu Gln Leu Ser Glu Lys Ala Thr
110                 115                 120                 125 ctg ggc cct gct gtg cgc ccc ctg ccc tgg cag cgc gtg gac cgc gac        433
Leu Gly Pro Ala Val Arg Pro Leu Pro Trp Gln Arg Val Asp Arg Asp
                130                 135                 140 gtg gca ccg gga act ctc tgc gac gtg gcc ggc tgg ggc ata gtc aac        481
Val Ala Pro Gly Thr Leu Cys Asp Val Ala Gly Trp Gly Ile Val Asn
            145                 150                 155 cac gcg ggc cgc cgc ccg gac agc ctg cag cac gtg ctc ttg cca gtg        529
His Ala Gly Arg Arg Pro Asp Ser Leu Gln His Val Leu Leu Pro Val
        160                 165                 170
```

```
ctg gac cgc gcc acc tgc aac cgg cgc acg cac cac gac ggc gcc atc    577
Leu Asp Arg Ala Thr Cys Asn Arg Arg Thr His His Asp Gly Ala Ile
    175                 180                 185 acc gag cgc ttg atg tgc gcg gag agc aat cgc cgg gac agc tgc aag    625
Thr Glu Arg Leu Met Cys Ala Glu Ser Asn Arg Arg Asp Ser Cys Lys
190                 195                 200                 205 ggt gac tcc ggg ggc ccg ctg gtg tgc ggg ggc gtg ctc gag ggc gtg    673
Gly Asp Ser Gly Gly Pro Leu Val Cys Gly Gly Val Leu Glu Gly Val
                210                 215                 220 gtc acc tcg ggc tcg cgc gtt tgc ggc aac cgc aag aag ccc ggg atc    721
Val Thr Ser Gly Ser Arg Val Cys Gly Asn Arg Lys Lys Pro Gly Ile
            225                 230                 235 tac acc cgc gtg gcg agc tat gcg gcc tgg atc gac agc gtc ctg gcc    769
Tyr Thr Arg Val Ala Ser Tyr Ala Ala Trp Ile Asp Ser Val Leu Ala
        240                 245                 250 tag ggtgccgggg cctgaaggtc aggtcaccc aagcaacaaa gtcccgagca          822
 * atgacccgaa ttc                                                     835
```

<210> SEQ ID NO 2
<211> LENGTH: 253
<212> TYPE: PRT
<213> ORGANISM: Homo sapiens
<220> FEATURE:
<221> NAME/KEY: VARIANT
<222> LOCATION: 26
<223> OTHER INFORMATION: Polymorphic amino acid Ile or Met
<220> FEATURE:
<221> NAME/KEY: VARIANT
<222> LOCATION: 52
<223> OTHER INFORMATION: Polymorphic amino acid Gly or Ala
<220> FEATURE:
<221> NAME/KEY: VARIANT
<222> LOCATION: 59
<223> OTHER INFORMATION: Polymorphic amino acid Gln or Arg
<220> FEATURE:
<221> NAME/KEY: VARIANT
<222> LOCATION: 150
<223> OTHER INFORMATION: Polymorphic amino acid Val or Leu

<400> SEQUENCE: 2

```
Met His Ser Ser Val Tyr Phe Ala Val Leu Val Leu Leu Gly Ala Ala
 1               5                  10                  15

Ala Cys Ala Ala Arg Pro Arg Gly Arg Ile Leu Gly Gly Arg Glu Ala
             20                  25                  30

Glu Ala His Ala Arg Pro Tyr Met Ala Ser Val Gln Leu Asn Gly Ala
         35                  40                  45

His Leu Cys Gly Gly Val Leu Val Ala Glu Gln Trp Val Leu Ser Ala
     50                  55                  60

Ala His Cys Leu Glu Asp Ala Ala Asp Gly Lys Val Gln Val Leu Leu
65                  70                  75                  80

Gly Ala His Ser Leu Ser Gln Pro Glu Pro Ser Lys Arg Leu Tyr Asp
                 85                  90                  95

Val Leu Arg Ala Val Pro His Pro Asp Ser Gln Pro Asp Thr Ile Asp
            100                 105                 110

His Asp Leu Leu Leu Leu Gln Leu Ser Glu Lys Ala Thr Leu Gly Pro
        115                 120                 125

Ala Val Arg Pro Leu Pro Trp Gln Arg Val Asp Arg Asp Val Ala Pro
    130                 135                 140

Gly Thr Leu Cys Asp Val Ala Gly Trp Gly Ile Val Asn His Ala Gly
145                 150                 155                 160
```

```
Arg Arg Pro Asp Ser Leu Gln His Val Leu Pro Val Leu Asp Arg
            165                 170                 175

Ala Thr Cys Asn Arg Arg Thr His His Asp Gly Ala Ile Thr Glu Arg
        180                 185                 190

Leu Met Cys Ala Glu Ser Asn Arg Arg Asp Ser Cys Lys Gly Asp Ser
    195                 200                 205

Gly Gly Pro Leu Val Cys Gly Val Leu Gly Val Val Thr Ser
210                 215                 220

Gly Ser Arg Val Cys Gly Asn Arg Lys Lys Pro Gly Ile Tyr Thr Arg
225                 230                 235                 240

Val Ala Ser Tyr Ala Ala Trp Ile Asp Ser Val Leu Ala
                245                 250

<210> SEQ ID NO 3
<211> LENGTH: 762
<212> TYPE: DNA
<213> ORGANISM: Homo sapiens
<220> FEATURE:
<221> NAME/KEY: CDS
<222> LOCATION: (1)...(762)

<400> SEQUENCE: 3 atg cac agc tgg gag cgc ctg gca gtt ctg gtc ctc cta gga gcg gcc     48
Met His Ser Trp Glu Arg Leu Ala Val Leu Val Leu Leu Gly Ala Ala
1               5                   10                  15 gcc tgc gcg gcg ccg ccc cgt ggt cgg atc ctg ggc ggc aga gag gcc     96
Ala Cys Ala Ala Pro Pro Arg Gly Arg Ile Leu Gly Gly Arg Glu Ala
            20                  25                  30 gag gcg cac gcg cgg ccc tac atg gcg tcg gtg cag ctg aac ggc gcg    144
Glu Ala His Ala Arg Pro Tyr Met Ala Ser Val Gln Leu Asn Gly Ala
        35                  40                  45 cac ctg tgc ggc ggc gtc ctg gtg gcg gag cag tgg gtg ctg agc gcg    192
His Leu Cys Gly Gly Val Leu Val Ala Glu Gln Trp Val Leu Ser Ala
    50                  55                  60 gcg cac tgc ctg gag gac gcg gcc gac ggg aag gtg cag gtt ctc ctg    240
Ala His Cys Leu Glu Asp Ala Ala Asp Gly Lys Val Gln Val Leu Leu
65                  70                  75                  80 ggc gcg cac tcc ctg tcg cag ccg gag ccc tcc aag cgc ctg tac gac    288
Gly Ala His Ser Leu Ser Gln Pro Glu Pro Ser Lys Arg Leu Tyr Asp
                85                  90                  95 gtg ctc cgc gca gtg ccc cac ccg gac agc cag ccc gac acc atc gac    336
Val Leu Arg Ala Val Pro His Pro Asp Ser Gln Pro Asp Thr Ile Asp
            100                 105                 110 cac gac ctc ctg ctg cta cag ctg tcg gag aag gcc aca ctg ggc cct    384
His Asp Leu Leu Leu Leu Gln Leu Ser Glu Lys Ala Thr Leu Gly Pro
        115                 120                 125 gct gtg cgc ccc ctg ccc tgg cag cgc gtg gac cgc gac gtg gca ccg    432
Ala Val Arg Pro Leu Pro Trp Gln Arg Val Asp Arg Asp Val Ala Pro
    130                 135                 140 gga act ctc tgc gac gtg gcc ggc tgg ggc ata gtc aac cac gcg ggc    480
Gly Thr Leu Cys Asp Val Ala Gly Trp Gly Ile Val Asn His Ala Gly
145                 150                 155                 160 cgc cgc ccg gac agc ctg cag cac gtg ctc ttg cca gtg ctg gac cgc    528
Arg Arg Pro Asp Ser Leu Gln His Val Leu Leu Pro Val Leu Asp Arg
                165                 170                 175 gcc acc tgc aac cgg cgc acg cac cac gac ggc gcc atc acc gag cgc    576
Ala Thr Cys Asn Arg Arg Thr His His Asp Gly Ala Ile Thr Glu Arg
            180                 185                 190
```

```
ttg atg tgc gcg gag agc aat cgc cgg gac agc tgc aag ggt gac tcc    624
Leu Met Cys Ala Glu Ser Asn Arg Arg Asp Ser Cys Lys Gly Asp Ser
        195                 200                 205 ggg ggc ccg ctg gtg tgc ggg ggc gtg ctc gag ggc gtg gtc acc tcg    672
Gly Gly Pro Leu Val Cys Gly Gly Val Leu Glu Gly Val Val Thr Ser
210                 215                 220 ggc tcg cgc gtt tgc ggc aac cgc aag aag ccc ggg atc tac acc cgc    720
Gly Ser Arg Val Cys Gly Asn Arg Lys Lys Pro Gly Ile Tyr Thr Arg
225                 230                 235                 240 gtg gcg agc tat gcg gcc tgg atc gac agc gtc ctg gcc tag            762
Val Ala Ser Tyr Ala Ala Trp Ile Asp Ser Val Leu Ala *
                245                 250

<210> SEQ ID NO 4
<211> LENGTH: 253
<212> TYPE: PRT
<213> ORGANISM: Homo sapiens
<220> FEATURE:
<221> NAME/KEY: VARIANT
<222> LOCATION: 26
<223> OTHER INFORMATION: Polymorphic amino acid Ile or Met
<220> FEATURE:
<221> NAME/KEY: VARIANT
<222> LOCATION: 52
<223> OTHER INFORMATION: Polymorphic amino acid Gly or Ala
<220> FEATURE:
<221> NAME/KEY: VARIANT
<222> LOCATION: 59
<223> OTHER INFORMATION: Polymorphic amino acid Gln or Arg
<220> FEATURE:
<221> NAME/KEY: VARIANT
<222> LOCATION: 150
<223> OTHER INFORMATION: Polymorphic amino acid Val or Leu

<400> SEQUENCE: 4

Met His Ser Trp Glu Arg Leu Ala Val Leu Val Leu Leu Gly Ala Ala
1               5                   10                  15

Ala Cys Ala Ala Pro Pro Arg Gly Arg Ile Leu Gly Gly Arg Glu Ala
            20                  25                  30

Glu Ala His Ala Arg Pro Tyr Met Ala Ser Val Gln Leu Asn Gly Ala
        35                  40                  45

His Leu Cys Gly Gly Val Leu Val Ala Glu Gln Trp Val Leu Ser Ala
    50                  55                  60

Ala His Cys Leu Glu Asp Ala Ala Asp Gly Lys Val Gln Val Leu Leu
65                  70                  75                  80

Gly Ala His Ser Leu Ser Gln Pro Glu Pro Ser Lys Arg Leu Tyr Asp
                85                  90                  95

Val Leu Arg Ala Val Pro His Pro Asp Ser Gln Pro Asp Thr Ile Asp
            100                 105                 110

His Asp Leu Leu Leu Leu Gln Leu Ser Glu Lys Ala Thr Leu Gly Pro
        115                 120                 125

Ala Val Arg Pro Leu Pro Trp Gln Arg Val Asp Arg Asp Val Ala Pro
    130                 135                 140

Gly Thr Leu Cys Asp Val Ala Gly Trp Gly Ile Val Asn His Ala Gly
145                 150                 155                 160

Arg Arg Pro Asp Ser Leu Gln His Val Leu Leu Pro Val Leu Asp Arg
                165                 170                 175

Ala Thr Cys Asn Arg Arg Thr His His Asp Gly Ala Ile Thr Glu Arg
            180                 185                 190

Leu Met Cys Ala Glu Ser Asn Arg Arg Asp Ser Cys Lys Gly Asp Ser
        195                 200                 205
```

-continued

```
Gly Gly Pro Leu Val Cys Gly Val Leu Glu Gly Val Thr Ser
    210             215             220
Gly Ser Arg Val Cys Gly Asn Arg Lys Lys Pro Gly Ile Tyr Thr Arg
225             230             235             240
Val Ala Ser Tyr Ala Ala Trp Ile Asp Ser Val Leu Ala
            245             250

<210> SEQ ID NO 5
<211> LENGTH: 1071
<212> TYPE: DNA
<213> ORGANISM: Homo sapiens
<220> FEATURE:
<221> NAME/KEY: CDS
<222> LOCATION: (55)...(741)

<400> SEQUENCE: 5
gcagttctgg tcctcctagg agcggccgcc tgcgcggcgc ggccccgtgg tcgg atg           57
                                                            Met
                                                            1 ctg ggc ggc aga gag gcc gag gcg cac gcg cgg ccc tac atg gcg tcg         105
Leu Gly Gly Arg Glu Ala Glu Ala His Ala Arg Pro Tyr Met Ala Ser
        5                   10                  15 gtg cag ctg aac ggc gcg cac ctg tgc gca ggc gtc ctg gtg gcg gag         153
Val Gln Leu Asn Gly Ala His Leu Cys Ala Gly Val Leu Val Ala Glu
            20                  25                  30 cgg tgg gtg ctg agc gcg gcg cac tgc ctg gag gac gcg gcc gac ggg         201
Arg Trp Val Leu Ser Ala Ala His Cys Leu Glu Asp Ala Ala Asp Gly
        35                  40                  45 aag gtg cag gtt ctc ctg ggc gcg cac tcc ctg tcg cag ccg gag ccc         249
Lys Val Gln Val Leu Leu Gly Ala His Ser Leu Ser Gln Pro Glu Pro
 50                  55                  60                  65 tcc aag cgc ctg tac gac gtg ctc cgc gca gtg ccc cac ccg gac agc         297
Ser Lys Arg Leu Tyr Asp Val Leu Arg Ala Val Pro His Pro Asp Ser
                 70                  75                  80 cag ccc gac acc atc gac cac gac ctc ctg ctg cta cag ctg tcg gag         345
Gln Pro Asp Thr Ile Asp His Asp Leu Leu Leu Leu Gln Leu Ser Glu
             85                  90                  95 aag gcc aca ctg ggc cct gct gtg cgc ccc ctg ccc tgg cag cgc gtg         393
Lys Ala Thr Leu Gly Pro Ala Val Arg Pro Leu Pro Trp Gln Arg Val
            100                 105                 110 gac cgc gac gtg gca ccg gga act ctc tgc gac gtg gcc ggc tgg ggc         441
Asp Arg Asp Val Ala Pro Gly Thr Leu Cys Asp Val Ala Gly Trp Gly
        115                 120                 125 ata gtc aac cac gcg ggc cgc cgc ccg gac agc ctg cag cac gtg ctc         489
Ile Val Asn His Ala Gly Arg Arg Pro Asp Ser Leu Gln His Val Leu
130                 135                 140                 145 ttg cca gtg ctg gac cgc gcc acc tgc aac cgg gcg acg cac cac gac         537
Leu Pro Val Leu Asp Arg Ala Thr Cys Asn Arg Ala Thr His His Asp
                150                 155                 160 ggc gcc atc acc gag cgc ttg atg tgc gcg gag agc aat cgc cgg gac         585
Gly Ala Ile Thr Glu Arg Leu Met Cys Ala Glu Ser Asn Arg Arg Asp
            165                 170                 175 agc tgc aag ggt gac tcc ggg ggc ccg ctg gtg tgc ggg ggc gtg ctc         633
Ser Cys Lys Gly Asp Ser Gly Gly Pro Leu Val Cys Gly Gly Val Leu
        180                 185                 190 gag ggc gtg gtc acc tcg ggc tcg cgc gtt tgc ggc aac cgc aag aag         681
Glu Gly Val Val Thr Ser Gly Ser Arg Val Cys Gly Asn Arg Lys Lys
    195                 200                 205 ccc ggg atc tac acc cgc gtg gcg agc tat gcg gcc tgg atc gac agc         729
Pro Gly Ile Tyr Thr Arg Val Ala Ser Tyr Ala Ala Trp Ile Asp Ser
210                 215                 220                 225
```

```
gtc ctg gcc tag ggtgccgggg cctgaaggtc agggtcaccc aagcaacaaa    781
Val Leu Ala * gtcccgagca atgaagtcat ccactcctgc atctggttgg tctttattga gcacctacta  841
tatgcagaag gggaggccga ggtgggagga tcattggatc tcaggagttg gagatcagca  901
tgggccacgt agcgcgactc catctctaca aataaataaa aattagctgg gcaattggcg  961
ggcatggagg tgggtgcttg tagttccagc tactcaggag gctgaggtgg gaggatgact 1021 tgaacgcagg aggctgaggc tgcagtgagt tgtgattgca ccactgccct            1071
```

<210> SEQ ID NO 6
<211> LENGTH: 228
<212> TYPE: PRT
<213> ORGANISM: Homo sapiens
<220> FEATURE:
<221> NAME/KEY: VARIANT
<222> LOCATION: 27
<223> OTHER INFORMATION: Polymorphic amino acid Ala or Gly
<220> FEATURE:
<221> NAME/KEY: VARIANT
<222> LOCATION: 34
<223> OTHER INFORMATION: Polymorphic amino acid Arg or Gln
<220> FEATURE:
<221> NAME/KEY: VARIANT
<222> LOCATION: 125
<223> OTHER INFORMATION: Polymorphic amino acid Val or Leu

<400> SEQUENCE: 6

```
Met Leu Gly Gly Arg Glu Ala Glu Ala His Ala Arg Pro Tyr Met Ala
 1               5                  10                  15

Ser Val Gln Leu Asn Gly Ala His Leu Cys Ala Gly Val Leu Val Ala
                20                  25                  30

Glu Arg Trp Val Leu Ser Ala Ala His Cys Leu Glu Asp Ala Ala Asp
            35                  40                  45

Gly Lys Val Gln Val Leu Leu Gly Ala His Ser Leu Ser Gln Pro Glu
        50                  55                  60

Pro Ser Lys Arg Leu Tyr Asp Val Leu Arg Ala Val Pro His Pro Asp
65                  70                  75                  80

Ser Gln Pro Asp Thr Ile Asp His Asp Leu Leu Leu Leu Gln Leu Ser
                85                  90                  95

Glu Lys Ala Thr Leu Gly Pro Ala Val Arg Pro Leu Pro Trp Gln Arg
            100                 105                 110

Val Asp Arg Asp Val Ala Pro Gly Thr Leu Cys Asp Val Ala Gly Trp
        115                 120                 125

Gly Ile Val Asn His Ala Gly Arg Arg Pro Asp Ser Leu Gln His Val
    130                 135                 140

Leu Leu Pro Val Leu Asp Arg Ala Thr Cys Asn Arg Arg Thr His His
145                 150                 155                 160

Asp Gly Ala Ile Thr Glu Arg Leu Met Cys Ala Glu Ser Asn Arg Arg
                165                 170                 175

Asp Ser Cys Lys Gly Asp Ser Gly Gly Pro Leu Val Cys Gly Gly Val
            180                 185                 190

Leu Glu Gly Val Val Thr Ser Gly Ser Arg Val Cys Gly Asn Arg Lys
        195                 200                 205

Lys Pro Gly Ile Tyr Thr Arg Val Ala Ser Tyr Ala Ala Trp Ile Asp
    210                 215                 220

Ser Val Leu Ala
225
```